(12) United States Patent
Sampson et al.

(10) Patent No.: US 6,218,118 B1
(45) Date of Patent: Apr. 17, 2001

(54) METHOD AND MIXTURE REAGENTS FOR ANALYZING THE NUCLEOTIDE SEQUENCE OF NUCLEIC ACIDS BY MASS SPECTROMETRY

(75) Inventors: Jeffrey R. Sampson, Burlingame; Zohar H. Yakhini, Palo Alto; Peter G. Webb, Menlo Park; Nicholas M. Sampas, San Jose, all of CA (US); Anna M. Tsalenko, Chicago, IL (US); Joel Myerson, Berkeley, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 0 days.

(21) Appl. No.: 09/112,437

(22) Filed: Jul. 9, 1998

(51) Int. Cl.[7] .............................. C12Q 1/68; C12P 19/34; C12N 13/00; C07H 21/02; C07H 21/04
(52) U.S. Cl. .......................... 435/6; 435/91.2; 435/91.5; 435/173.1; 536/23.1; 536/24.31; 536/24.33; 536/25.32
(58) Field of Search .............................. 435/6, 91.2, 91.5; 436/173.1; 536/23.1, 25.32, 24.33, 24.31

(56) References Cited

U.S. PATENT DOCUMENTS

| | | |
|---|---|---|
| 4,883,750 | 11/1989 | Whiteley et al. . |
| 4,988,617 | 1/1991 | Landegren, et al. . |
| 5,202,231 | 4/1993 | Drmanac et al. . |
| 5,242,794 | 9/1993 | Whiteley et al. . |
| 5,288,644 | 2/1994 | Beavis et al. . |
| 5,403,709 | 4/1995 | Agrawal et al. . |
| 5,492,806 | 2/1996 | Drmanac et al. . |
| 5,494,810 | 2/1996 | Barany et al. . |
| 5,521,065 | 5/1996 | Whiteley et al. . |
| 5,547,835 | 8/1996 | Koster . |
| 5,605,798 | 2/1997 | Koster . |
| 5,622,824 | 4/1997 | Koster . |
| 5,695,940 | 12/1997 | Drmanac et al. . |
| 5,869,242 | * 2/1999 | Kamb ........................ 435/6 |
| 5,885,775 | * 3/1999 | Haff et al. ................. 435/6 |
| 5,942,391 | * 8/1999 | Zhang et al. .............. 435/6 |

FOREIGN PATENT DOCUMENTS

| | | |
|---|---|---|
| 59-131909 | 7/1984 | (JP) . |
| WO 92/15712 | 9/1992 | (WO) . |
| WO 95/04160 | 2/1995 | (WO) . |
| WO 96/27681 | 9/1996 | (WO) . |
| WO 97/35033 | 9/1997 | (WO) . |
| WO97/37041 | 10/1997 | (WO) . |
| WO 98/03684 | 1/1998 | (WO) . |
| WO98/14616 | 4/1998 | (WO) . |
| WO98/20166 | 5/1998 | (WO) . |

OTHER PUBLICATIONS

Koster et al Nature Biotechnology vol. 14, pp. 1123–1128, 1996.

Maxam and Gilbert, *Proc. Natl. Acad. Sci. USA*, 74:560(1977); "A New Method for Sequencing DNA"

Sanger, et al., *Proc. Natl. Acad. Sci.USA*, 74;5463(1977), "DNA Sequencing with Chain–terminating Inhibitors"

Kozal, M., et al., *Nature Med.*, 7:753–759(Jul. 1996); "Extensive Polymorphisms Observed in HIV–1 Clade B Protease Gene Using High–density Oligonucleotide Arrays"

Lockhart, D., et al., *Nat. Biotech.*, 14:1675–1680(1996), "Expression Monitoring by Hybridization to High–density Oligonucleotide Arrays"

Fields, G.B., *Clinical Chemistry*, 43:1108(1997); "Mass–Spectrometric Approaches for DNA–Based Genetic Screening"

Fu, et al., *Nat. Biotechnol*, 16:381(1998), "Sequencing Exons 5 to 8 of the p53 Gene by MALDI–TOF Mass Spectrometry"

Schneider and Chait, *Nucleic Acids Res*, 23:1570(1995); "Increased Stability of Nucleic Acids Containing 7–deaza–guanosine and 7–deaza–adenosine May Enable Rapid DNA Sequencing by Matrix–assisted Laser Desorption Mass Spectrometry"

Tang, et al., *J. Am Soc Mass Spectrom.*, 8:218–224(1997); "Positive Ion Formation in the Ultraviolet Matrix–Assisted Laser Desorption/Ionization Analysis of Oligonucleotides by Using 2,5–Dihydroxybenzoic Acid"

Pevzner, P.A., *J. Biomolecular Structure Dynamics*, 7:63(1989); "1–Tuple DNA Sequencing: Computer Analysis"

Pevzner, P.A., *J. Biomolecular Structure Dynamics*, 9:399(1991); Improved Chips for Sequencing by Hybridization Ukkonen, E., *Theoretical Computer Science*, 92:191(1992); "Approximate String–matching with q–grams and Maximal Matches"

\* cited by examiner

*Primary Examiner*—Kenneth R. Horlick
*Assistant Examiner*—Jeffrey Siew

(57) ABSTRACT

Methods and reagents are disclosed which satisfy the need for more sensitive, more accurate and higher through-put analyses of target nucleic acid sequences. The methods and reagents may be generically applied to generally any target nucleic acid sequence and do not require a priori information about the presence, location or identity of mutations in the target nucleic acid sequence. The reagents of the invention are mixtures of natural and mass-modified oligonucleotide precursors having a high level of coverage and mass number complexity. A method is also disclosed for analyzing a target nucleic acid sequence employing the mixtures of natural and mass-modified oligonucleotide precursors and chemical or enzymatic assays to alter the mass of the oligonucleotide precursors prior to mass spectral analysis, generally via MALDI-TOF. The enzymatic assay may be a polymerase extension assay or a ligase assay. The kits for carrying out the methods of the invention are also disclosed.

70 Claims, 22 Drawing Sheets

Nested set of overlapping X-mers

Nested set of semi-overlapping X-mers

Set of Non-overlapping X-mers

FIG. 11

62 Nucleotide Fragment of the Wild-Type P53 Gene and 6 Known Mutations:

p53_wt
AtgtgtaacagttcctgcatgggcGGCatgaacCGGAGGcccatcctcaccatcatcacactg (SEQ ID NO:1)

p53_2451-6
AtgtgtaacagttcctgcatgggcCGCatgaacCGGAGGcccatcctcaccatcatcacactg (SEQ ID NO:2)

p53_2481-1
AtgtgtaacagttcctgcatgggcGGCatgaacTGGAGGcccatcctcaccatcatcacactg (SEQ ID NO:3)

p53_2481-2
AtgtgtaacagttcctgcatgggcGGCatgaacGGGAGGcccatcctcaccatcatcacactg (SEQ ID NO:4)

p53_2481-5
AtgtgtaacagttcctgcatgggcGGCatgaacAGGAGGcccatcctcaccatcatcacactg (SEQ ID NO:5)

p53_2482-3
AtgtgtaacagttcctgcatgggcGGCatgaacCAGAGGcccatcctcaccatcatcacactg (SEQ ID NO:6)

p53_2482-5
AtgtgtaacagttcctgcatgggcGGCatgaacCTGAGGcccatcctcaccatcatcacactg (SEQ ID NO:7)

p53_2482-6
AtgtgtaacagttcctgcatgggcGGCatgaacCCGAGGcccatcctcaccatcatcacactg (SEQ ID NO:8)

378 Nucleotide Fragment of the Wild-Type P53 Gene

CagtcacagcacatgacggaggttgtgaggCGCgoccccaccatgagcgctgctcagatagcgatggtctggcccc
tcctcagcatcttatccgagtggaaggaaatttgcgtgtggagtatttggatgacagaaacactttttcgacatagtgtggtggt
gccctatgagccgcctgaggttggctctgactgtaccaccatccactacaactacatgtgtaacagttcctgcatgggcGG
CatgaacCGGAGGcccatcctcaccatcatcacactggaagactccagtggtaatctactgggacggaacagctttg
aggtgCGTgtttgtgcctgtcctgggagagacCGGcgcacagaggaagagaatctccgc (SEQ ID NO: 9)

740 Nucleotide Fragment of the Wild-Type P53 Gene cagggcagctacggtttccgtctgggcttcttgcattctgggacagccaagtctgtgacttgcacgtactcccctgccctcaa
caagatgttttgccaactggccaagacctgccctgtgcagctgtgggttgattccacaccccgcccggcacccgcgtccg
cgccatggccatctacaagcagtcacagcacatgacggaggttgtgaggCGCtgcccccaccatgagcgctgctcag
atagcgatggtctggcccctcctcagcatcttatccgagtggaaggaaatttgcgtgtggagtatttggatgacagaaacac
ttttcgacatagtgtggtggtgccctatgagccgcctgaggttggctctgactgtaccaccatccactacaactacatgtgtaa
cagttcctgcatgggcGGCatgaacCGGAGGcccatcctcaccatcatcacactggaagactccagtggtaatcta
ctgggacggaacagctttgaggtgCGTgtttgtgcctgtcctgggagagacCGGcgcacagaggaagagaatctcc
gcaagaaggggagcctcaccacgagctgccccagggagcactaagcgagcactgcccaacaacaccagctcctc
tccccagccaaagaagaaaccactggatggagaatatttcaccttcagatccgtgggcgtgagcgcttcgagatgttcc
gagagctgaatgaggccttggaact (SEQ ID NO: 10)

FIG. 12

TACACATTGTCAAGGACGTACCCGCcGTACTTGGCCTCCGGGTAGGAGTGGTAGTAGTGTGAC (SEQ ID NO: 11)
ATGTGTA
 TGTGTAA
  GTGTAAC
   TGTAACA
    GTAACAG
     TAACAGT
      AACAGTT
       ACAGTTC
        CAGTTCC
         AGTTCCT
          GTTCCTG
           TTCCTGC
            TCCTGCA
             CCTGCAT
              CTGCATG
               TGCATGG
                GCATGGG
                 CATGGGC
                  ATGGGCG
                   TGGGCGG
                    GGGCGGC
                     GGCGGCA
                      GCGGCAT
                       CGGCATG
                        GGCATGA
                         GCATGAA
                          CATGAAC
                           ATGAACC
                            TGAACCG
                             GAACCGG
                              AACCGGA
                               ACCGGAG
                                CCGGAGG
                                 CGGAGGC
                                  GGAGGCC
                                   GAGGCCC
                                    AGGCCCA
                                     GGCCCAT
                                      GCCCATC
                                        CCCATCC
                                         CCATCCT
                                           CATCCTC
                                             ATCCTCA
                                              TCCTCAC
                                                CCTCACC
                                                 CTCACCA
                                                   TCACCAT
                                                    CACCATC
                                                      ACCATCA
                                                        CCATCAT
                                                          CATCATC
                                                            ATCATCA
                                                              TCATCAC
                                                                CATCACA
                                                                  ATCACAC
                                                                    TCACACT
                                                                     CACACTG

FIG. 17
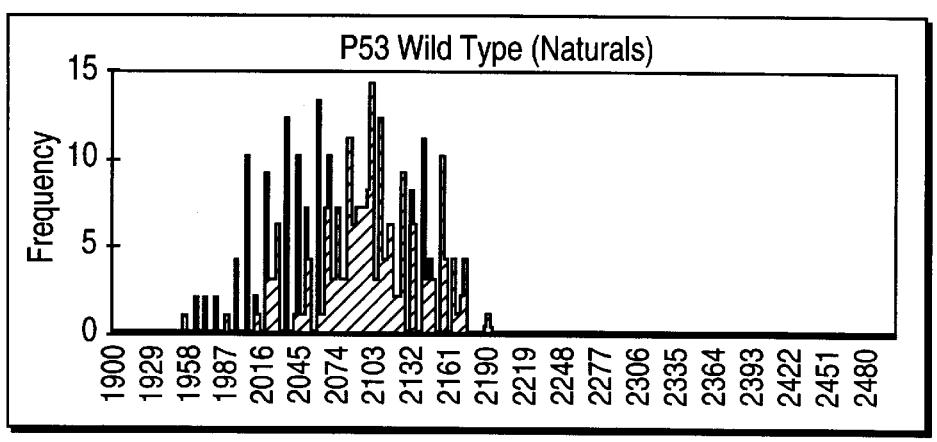
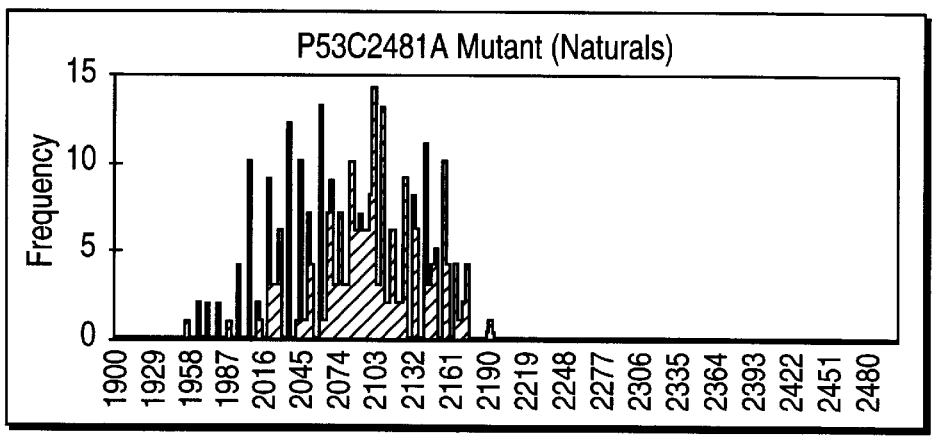
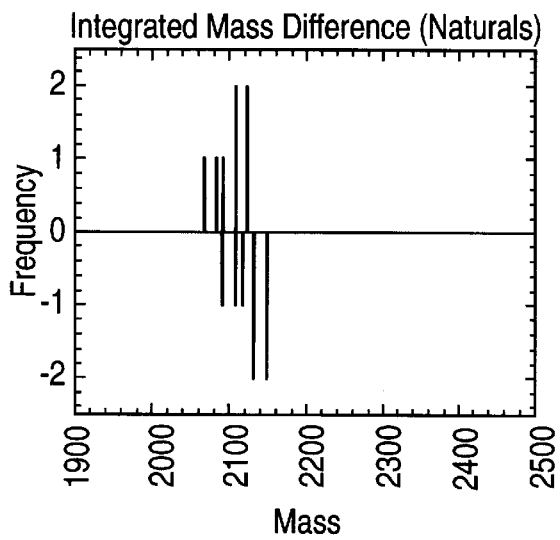
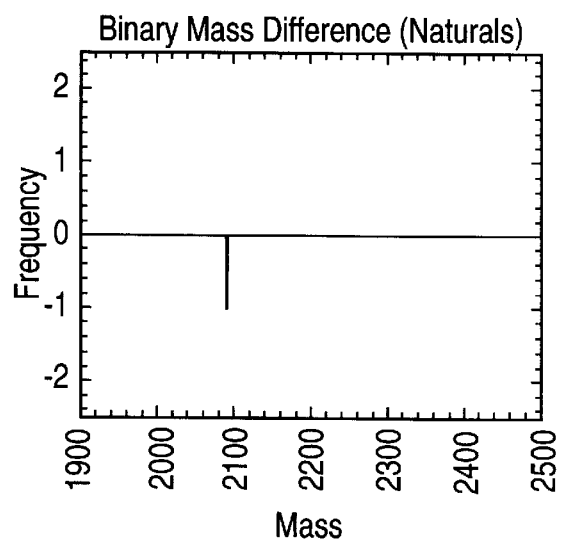

FIG. 18
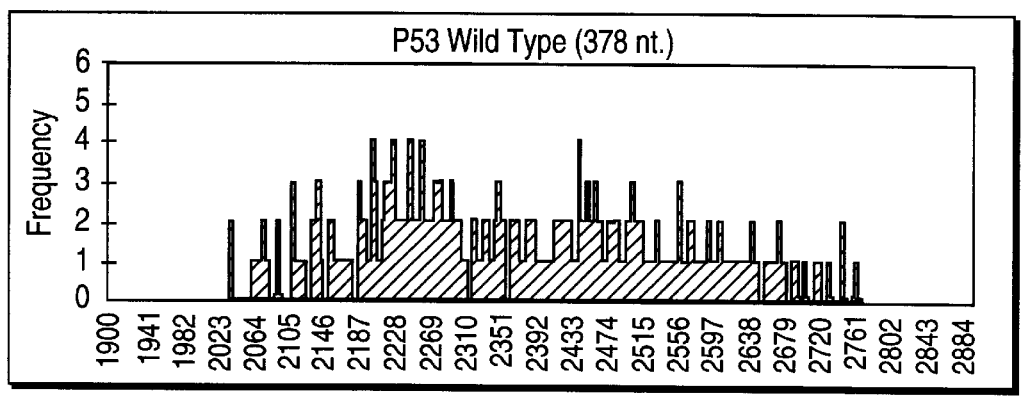
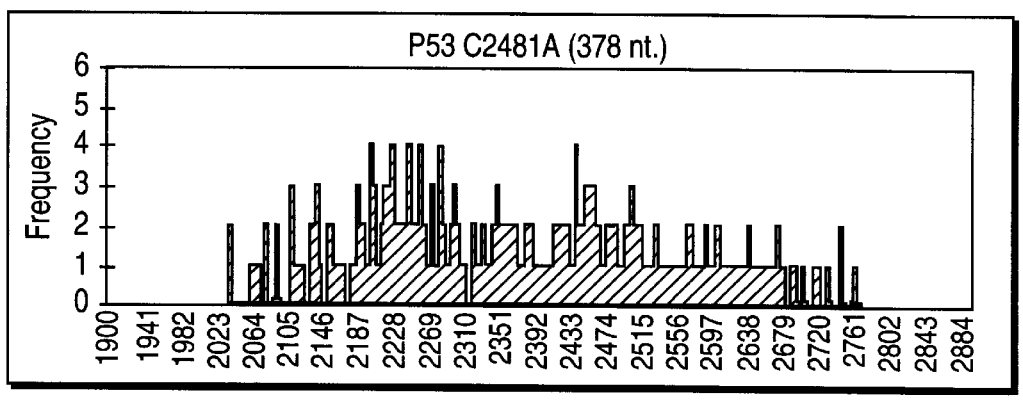
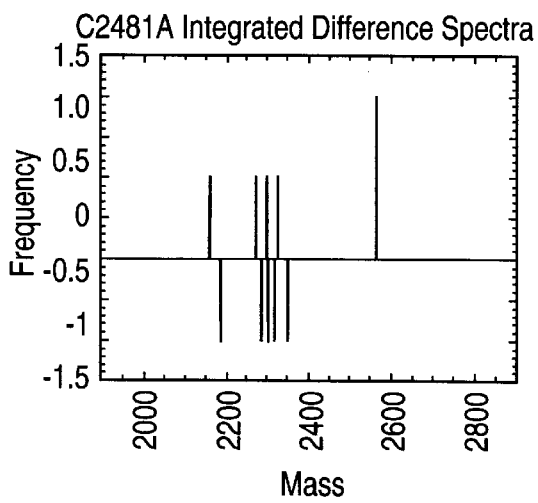
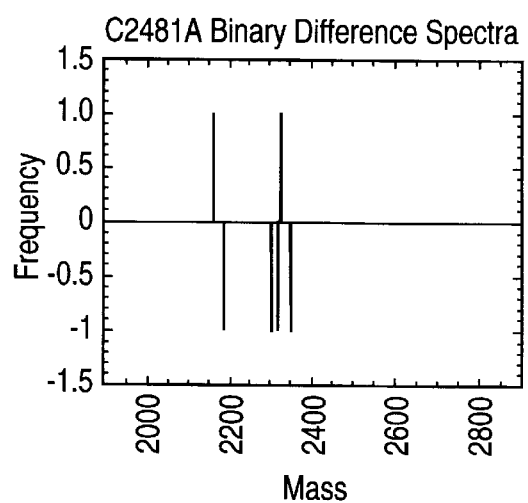

FIG. 19

TACACATTGTCAAGGACGTACCCGCCGTACTTGGCCTCCGGGTAGGAGTGGTAGTAGTGTGAC (SEQ ID NO: 11)

```
A
 TGTGTA
      A
       CA
         GTTCCTGCA
                  TGGGCGGCA
                           TGA
                              A
                               CCGGA
                                    GGCCCA
ATG                                       TCCTCA
   TG                                           CCA
    TAACAG                                         TCA
          TTCCTG                                      TCA
                CATG                                    CA
                    G                                     CTG
                     G
                      CG
                        G
                         CATG
                             AACCG
                                  G
                                   AG
ATGTGTAAC                            G
        AGTTC                         CCCATCCTCACCATCATCACACTG (SEQ ID NO: 12)
             C
              TGC
                 ATGGGC
                       GGC
                          ATGAAC
                                C
                                 GGAGGC
                                       C
                                        C
                                         ATC
                                            C
                                             TC
                                               AC
                                                 C
                                                  ATC
                                                     ATC
  AT                                                    AC
   GT                                                     AC
    GT                                                      TG
     AACAGT
           T
            CCT
               GCAT
                   GGGCGGCAT
                            GAACCGGAGGCCCAT (SEQ ID NO: 13)
                                         CCT
                                            CACCAT
                                                  CAT
                                                     CACACT
                                                           G
```

FIG. 20
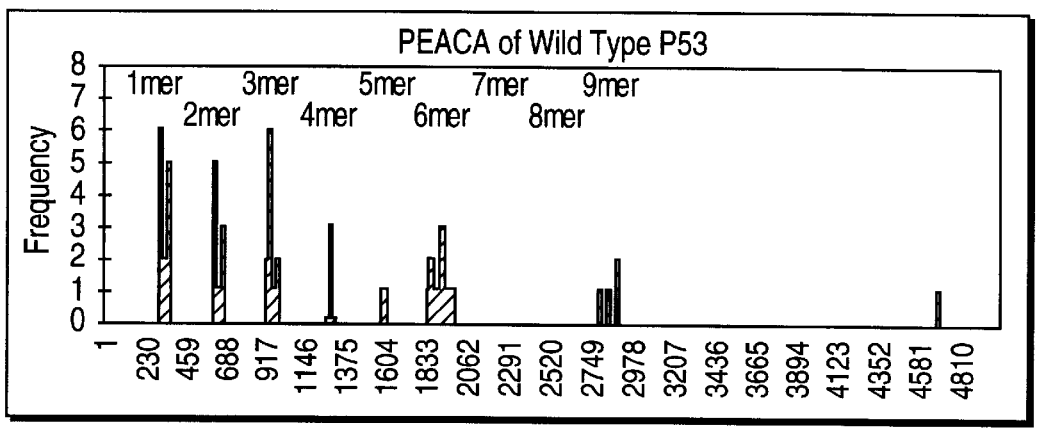
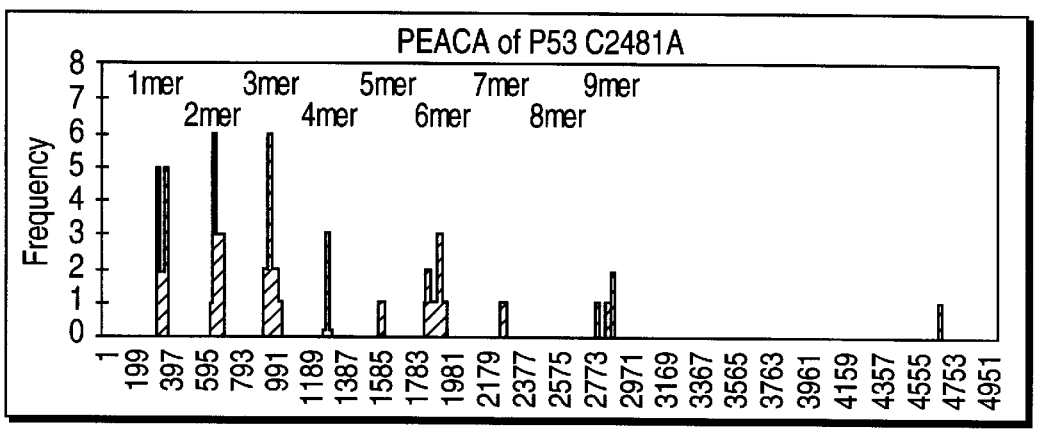
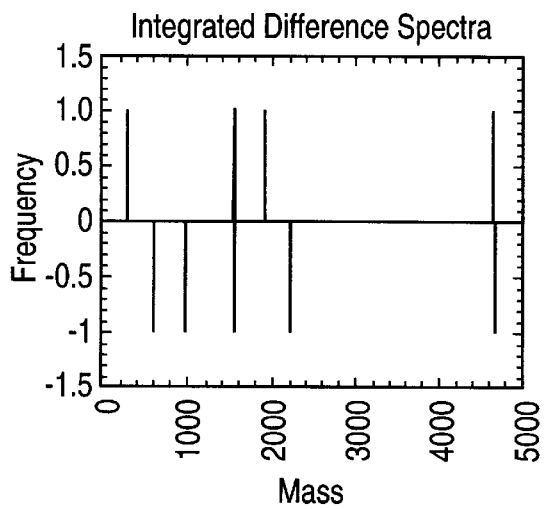
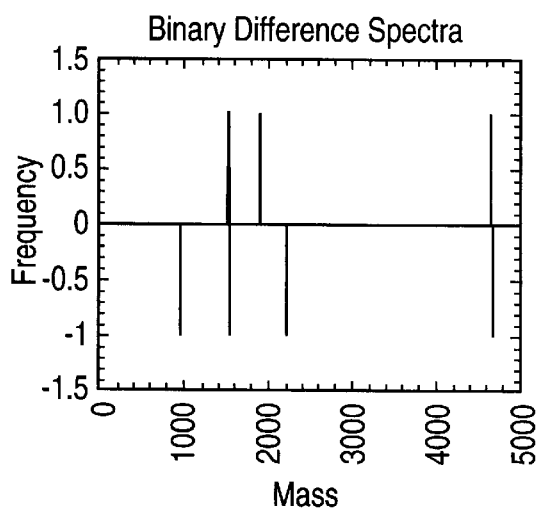

FIG. 21
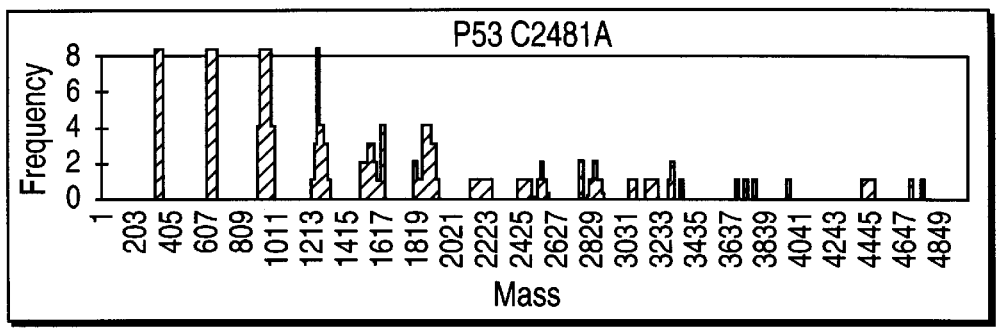
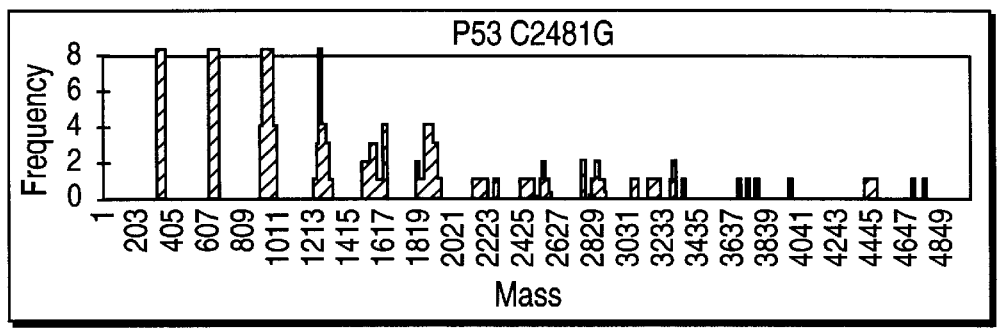
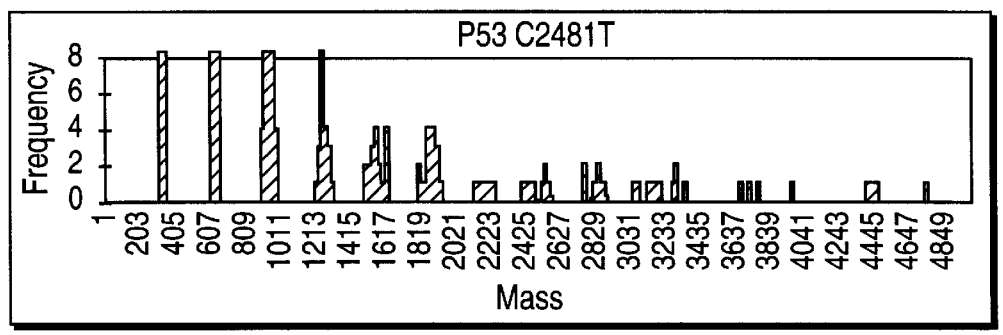
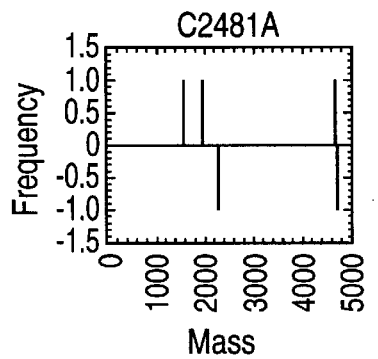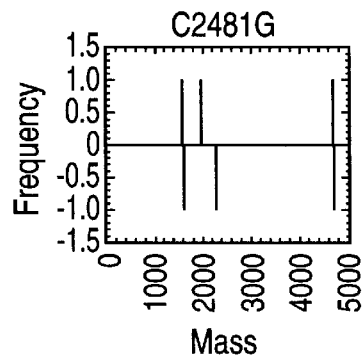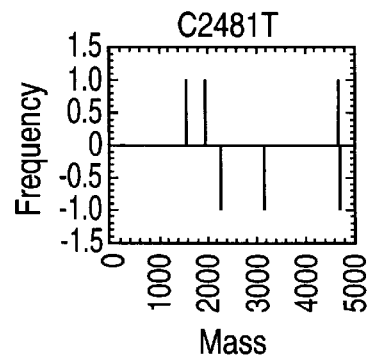

FIG. 22
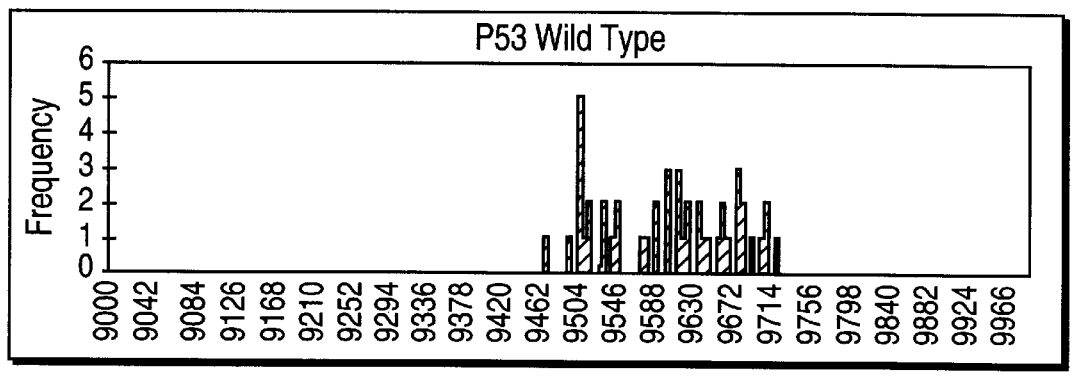
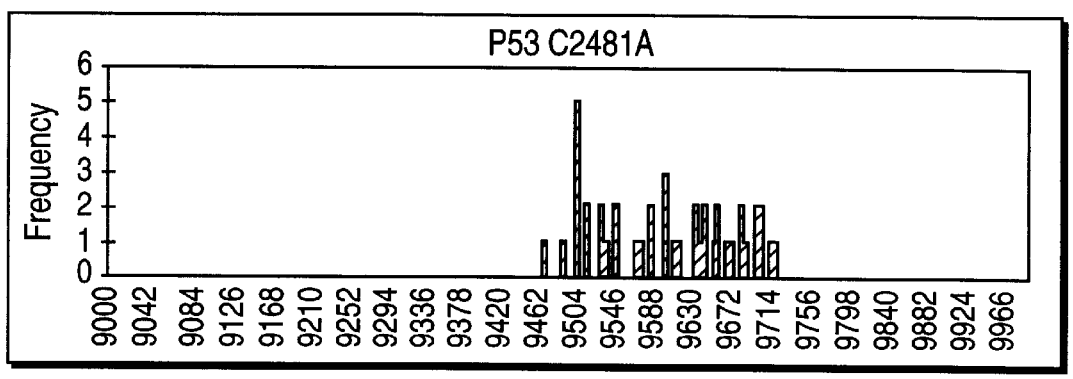
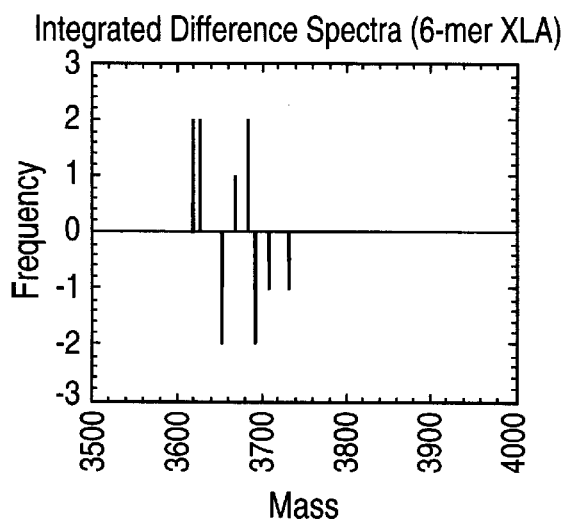
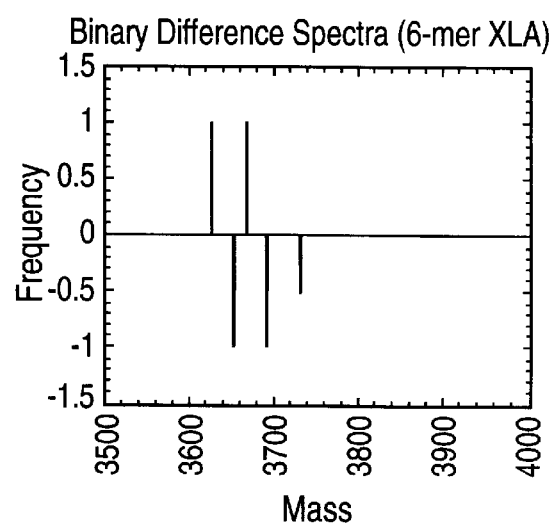

FIG. 23
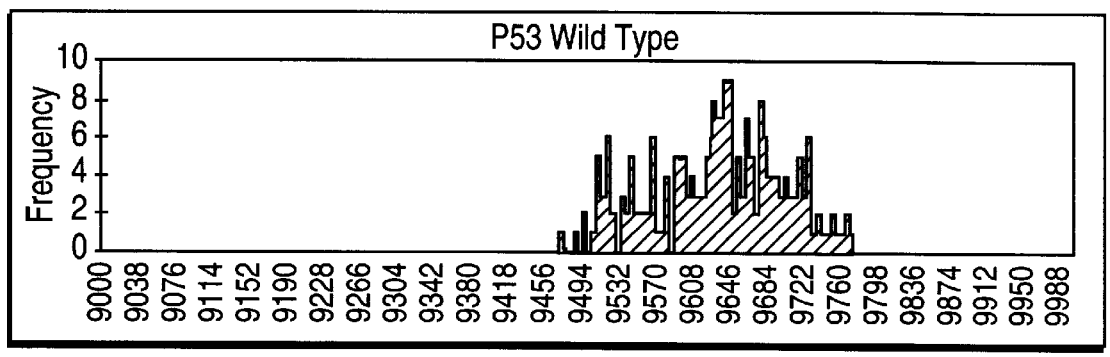
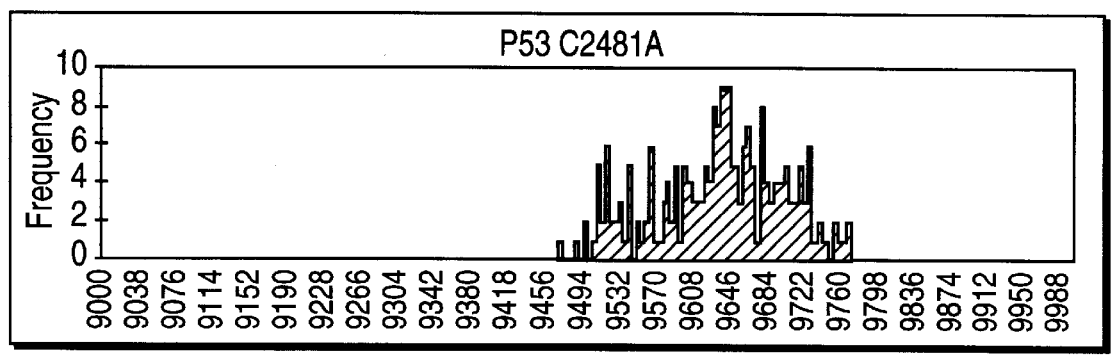
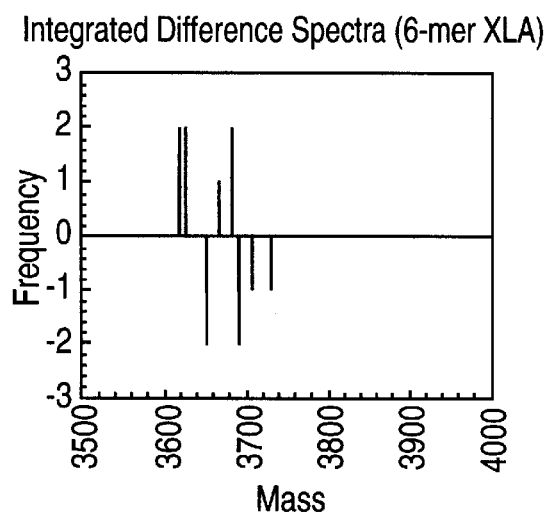
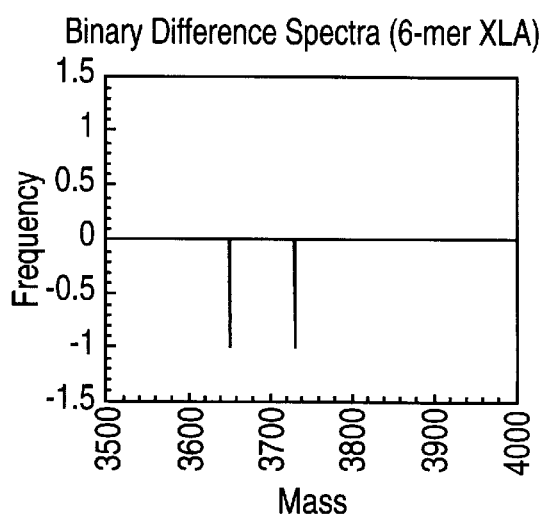

METHOD AND MIXTURE REAGENTS FOR ANALYZING THE NUCLEOTIDE SEQUENCE OF NUCLEIC ACIDS BY MASS SPECTROMETRY

FIELD OF THE INVENTION

This invention relates to methods and reagents for analyzing nucleotide sequences of nucleic acids via mass spectrometry and, more particularly, to methods for analyzing nucleotide sequences employing reagents that are mixtures of oligonucleotide precursors having a high level of mass number complexity and sequence- coverage complexity.

BACKGROUND OF THE INVENTION

Determining the nucleotide sequence of nucleic acids (DNA and RNA) is critical to understanding the function and control of genes and their relationship, for example, to disease discovery and disease management. Analysis of genetic information plays a crucial role in the biological experimentation. This has become especially true with regard to studies directed at understanding the fundamental genetic and environmental factors associated with disease and the effects of potential therapeutic agents on the cell. This paradigm shift has lead to an increasing need within the life science industries for more sensitive, more accurate and higher-throughput technologies for performing analysis on genetic material obtained from a variety of biological sources.

Because sequencing the enormously large number of nucleic acids in each human cell is necessarily a time-consuming process, there is always a pressing need for faster and higher through-put analyses that do not sacrifice sensitivity and accuracy. A number of techniques have been developed, including, inter alia, electrophoresis, enzymatic and chemical analysis, array technology and mass spectrometry, to determine the nucleotide sequence of nucleic acids.

Electrophoretic Techniques

Slab or capillary polyacrylamide gel electrophoresis technologies, such as those employed in automated DNA sequencers, provide highly accurate de novo sequence information for relatively long (500–700 residues or bases) segments of DNA. Although electrophoresis-based techniques provide a great amount of information per sample, they require long sample preparation and set-up times and thereby limit throughput.

Enzymatic and Chemical Analysis

A number of enzymatic and chemical techniques exist to determine the de novo nucleotide sequence of nucleic acids. However, each technique has inherent limitations. For example, Maxam and Gilbert [Proc. Natl. Acad. Sci. USA 74:5460 (1977)] disclose a chemical degradation approach and Sanger et al. [Proc. Natl. Acad. Sci. USA 74:5463 (1977)] disclose a chain termination method using complementary strand primer extension. Each of these techniques utilizes four separate reaction mixtures to create a nested set of fragments differing by a single nucleotide in length, thus representing a complete nucleotide sequence. A resolution of the fragments based on their size and terminating nucleotide is carried out to determine the order of the fragments and hence the nucleotide sequence.

Single-stranded conformation polymorphism (SSCP) analysis a useful technique for detecting relatively small differences among similar sequences. The technique is simple to implement and, when combined with multiple-dye detection or mass-tag methodologies, may be multiplexed and thereby improve throughput. However, like techniques that rely on detecting heteroduplexes, such as denaturing gradient gel electrophoresis (DGGE), chemical cleavage (CCM), enzymatic cleavage (using cleavase) of mismatches, and denaturing high performance liquid chromatography (DHPLC), the technique is only qualitative, i.e., the technique only reveals whether a mutation is present within the target nucleic acid but gives minimal information about the identity and location of the mutation.

Other techniques employing ligase and polymerase extension assays are useful for determining whether a mutation is present at a defined location in an otherwise known target nucleic acid sequence. U.S. Pat. No. 4,988,617, for example, discloses a method for determining whether a mutation is present at a defined location in an otherwise known target nucleic acid sequence by assaying for the ligation of two natural oligonucleotides that are designed to hybridize adjacent to one another along the target sequence. U.S. Pat. No. 5,494,810 discloses a method that utilizes a thermostable ligase and the ligase chain reaction (LCR) to detect specific nucleotide substitutions, deletions, insertions and translocations within an otherwise known target nucleic acid sequence using only natural nucleic acids. U.S. Pat. No. 5,403,709 discloses a method for determining the nucleotide sequence by using another oligonucleotide as an extension and a third, bridging oligonucleotide to hold the first two together for ligation, and WO 97/35033 discloses methods for determining the identity of a nucleotide 3' to a defined primer using a polymerase extension assay. Although the assays may be performed with a relatively high throughput, they are sequence specific and, thus require a different set of reagents for each target to be analyzed.

U.S. Pat. Nos. 5,521,065, 4,883,750 and 5,242,794 (Whiteley, et al.) disclose methods of testing for the presence or absence of a target sequence in a mixture of single-stranded nucleic acid fragments. The method involves reacting a mixture of single-stranded nucleic acid fragments with a first probe that is complementary to a first region of the target sequence and with a second probe that is complementary to a second region of the target sequence. The first and second target regions are contiguous with one another. Hybridization conditions are used in which the two probes become stably hybridized to their associated target regions. Following hybridization, any of the first and second probes hybridized to contiguous first and second target regions are ligated, and the sample is subsequently tested for the presence of expected probe ligation product.

Array Technology

Techniques employing hybridization to surface-bound DNA probe arrays are useful for analyzing the nucleotide sequence of target nucleic acids. These techniques rely upon the inherent ability of nucleic acids to form duplexes via hydrogen bonding according to Watson-Crick base-pairing rules. In theory, and to some extent in practice, hybridization to surface-bound DNA probe arrays can provide a relatively large amount of information in a single experiment. For example, array technology has identified single nucleotide polymorphisms within relatively long (1,000 residues or bases) sequences (Kozal, M., et al., *Nature Med.* 7:753–759, July 1996). In addition, array technology is useful for some types of gene expression analysis, relying upon a comparative analysis of complex mixtures of MRNA target sequences (Lockart, D., et al., (1996) *Nat. Biotech.* 14, 1675–1680). Although array technologies offer the advantages of being reasonably sensitive and accurate when developed for specific applications and for specific sets of target sequences, they lack a generic implementation that can simultaneously be applied to multiple and/or different applications and targets. This is in large part due to the need for relatively long probe sequences, which are required to form and subsequently detect the probe/target duplexes. Moreover, this use of relatively long probes makes it difficult to interrogate single nucleotide differences due to the inherently small thermodynamic difference between the perfect complement and the single mismatch within the probe/target duplex. In addition, detection depends upon solution diffusion properties and hydrogen bonding between complementary target and probe sequences.

Mass Spectrometry Techniques

Mass spectrometry (MS) is a powerful tool for analyzing complex mixtures of compounds, including nucleic acids. In addition to accurately determining an intact mass, primary structure information can be obtained by several different MS strategies. The use of MS for DNA analysis has potential application to the detection of DNA modifications, DNA fragment mass determination, and DNA sequencing (see for example; Fields, G. B., *Clinical Chemistry* 43, 1108 (1997)). Both fast atom bombardment (FAB) and electrospray ionization (ESI) collision-induced dissociation/tandem MS have been applied for identification of DNA modification sites.

Although MS is a powerful tool for analyzing complex mixtures of related compounds, including nucleic acids, its utility for analyzing the sequence of nucleic acids is limited by available ionization and detection methods. For example, ESI spectrometry produces a distribution of highly charged ions having a mass-to-charge ratio in the range of commercially available quadrupole mass analyzers. While ESI is sensitive, requiring only femtomole quantities of sample, it relies on multiple charges to achieve efficient ionization and produces complex and difficult-to-interpret multiply-charged spectra for even simple nucleic acids.

Matrix-assisted laser desorption ionization (MALDI) used in conjunction with a time-of-flight (TOF) mass analyzer holds great potential for sequencing nucleic acids because of its relatively broad mass range, high resolution (m/$\Delta$m$\leq$1.0 at mass 5,000) and sampling rate (up to 1 sample/second). In one aspect MALDI offers a potential advantage over ESI and FAB in that biomolecules of large mass can be ionized and analyzed readily. Furthermore, in contrast to ESI, MALDI produces predominantly singly charged species.

However, in general, MALDI analysis of DNA may suffer from lack of resolution of high molecular weight DNA fragments, DNA instability, and interference from sample preparation reagents. Longer oligonucleotides can give broader, less-intense signals, because MALDI imparts greater kinetic energies to ions of higher molecular weights. Although it may be used to analyze high molecular-weight nucleic acids, MALDI-TOF induces cleavage of the nucleic acid backbone, which further complicates the resulting spectrum. As a result, the lengths of nucleic acid sequences that may currently be analyzed via MALDI-TOF is limited to about 100 bases or residues. Wang et al. (WO 98/03684) have taken advantage of "in source fragmentation" and coupled it with delayed pulsed ion extraction methods for determining the sequence of nucleic acid analytes.

A number of methods have been disclosed that take advantage of standard sequencing methods for generating target fragments for analysis by mass spectroscopy. For example, U.S. Pat. No. 5,288,644 (Beavis, et al.); U.S. Pat. No. 5,547,835 (Koster) and U.S. Pat. No. 5,622,824 (Koster) disclose methods for determining the sequence of a target nucleic acid using MALDI-TOF of ladders of the target produced either by exonuclease digestion or by standard Sanger sequencing methods. Beavis discusses a method for DNA sequencing utilizing different base-specific reactions to use different sets of DNA fragments to form a piece of DNA of unknown sequence. Each of the different sets of DNA fragments has a common origin and terminates at a particular base along the unknown sequence. The molecular weights of the DNA fragments in each of the different sets are determined by a MALDI mass spectrometer which is then used to deduce the nucleotide sequence of the DNA.

Koster utilizes the Sanger sequencing strategy and assembles the sequence information by analysis of the nested fragments obtained by base-specific chain termination via their different molecular masses using mass spectrometry such as MALDI or ESI mass spectrometry. This method has been coupled with a solid-phase sequencing approach in which the template is labeled with biotin and bound to streptavidin-coated magnetic beads. Using this method, it was possible to sequence exons 5 and 8 of p53 gene using 21 defined primers (Fu et al., *Nat. Biotechnol* 16, 381 (1998)). Throughput can be increased by introducing mass modifications in the oligonucleotide primer, chain-terminating nucleoside triphosphates and/or in the chain-elongating nucleoside triphosphates, as well as using integrated tag sequences that allow multiplexing by hybridization of tag specific probes with mass differentiated molecular weights (U.S. Pat. No. 5,547,835). It is important to note, however, that all of these sequencing methods require either some prior knowledge of the target sequence or introduction of a known sequence to serve as the primer-binding site.

Efforts have been made to use mass spectrometry with enzymatic assays to determine the presence, location and identity of mutations in otherwise known sequences wherein at least some information is known a priori about the presence, location and/or identity of the mutation. U.S. Pat. No. 5,605,798, for example, discloses a method wherein a DNA primer that is complementary to a known target molecule in a region adjacent to the known region of interest is extended with a DNA polymerase in the presence of mass-tagged dideoxynucleotides. The identity of the mutation is then determined by analyzing the mass of the dideoxy-extended DNA primer. The multiplexing method is disclosed to be useful for simultaneously detecting all possible mutants/variants at a defined site by extending with a dideoxynucleotide and determining which specific dideoxynucleotide was incorporated.

Efforts have been made to address some of the aforementioned deficiencies with mass spectroscopic analyses of nucleic acids. For example, Gut (WO 96/27681) discloses methods for altering the charge properties of the phosphodiester backbone of nucleic acids in ways that make them more suitable for MS analyses. Methods for introducing modified nucleotides that stabilize the nucleic acid against fragmentation have also been described (Schneider and Chait, *Nucleic Acids Res*, 23, 1570 (1995), Tang et al., *J Am Soc Mass Spectrom*, 8, 218–224, 1997).

The use of non-cleavable mass tags has also been exploited to address some of the aforementioned deficiencies. For example, Japanese Patent No. 59-131909 discloses a mass spectrometer design that detects nucleic acid fragments separated by electrophoresis, liquid chromatography or high speed gel filtration, wherein atoms have been incorporated into the nucleic acids. The atoms, which normally do not occur in DNA, are sulfur, bromine, iodine, silver, gold, platinum, and mercury.

Cleavable mass tags have been exploited to circumvent some of the problems associated with MS analysis of nucleic acids. For example, PCT Application WO 95/04160 (Southern, et al.) discloses an indirect method for analyzing the sequence of target nucleic acids using target-mediated ligation between a surface-bound DNA probe and cleavable mass-tagged oligonucleotides containing reporter groups using mass spectrometric techniques. The sequence to be determined is first hybridized to an oligonucleotide attached to a solid support. The solid support carrying the hybrids from above is incubated with a solution of coded oligonucleotide reagents that form a library comprising all sequences of a given length. Ligase is introduced so that the oligonucleotide on the support is ligated to the member of the library that is hybridized to the target adjacent the oligonucleotide. Non-ligated reagents are removed by washing. A linker that is part of the member of the library ligated to the oligonucleotide is broken to detach a tag, which is recovered and analyzed by mass spectrometry.

A common focus of the above technologies is to provide methods for increasing the number of target sites (either intra- or inter-target) that can be interrogated in a single determination where some portion of the target sequence is known. This multiplexing theme is either directly stated or implied in the teachings of the above patent applications. The use of more than one oligonucleotide as either a hybridization probe or primer for extension or ligation is defined by the sequence surrounding the site of interest and, therefore, the specific application. Thus, with the exception of the mass-tag technology disclosed by Southern, the oligonucleotide reagents described above are not generic in terms of target sequence, but must be generated for each defined application. As such, the number of distinct oligonucleotides used in a multiplexed interrogation is generally only a small subset of the theoretical sequence-complete set. This ratio of actual sequence coverage provided by a particular oligonucleotide mixture to the theoretical coverage provided by the sequence-complete set is defined as the mixture coverage complexity (see discussion below). For example, in many of the methods described (i.e., U.S. Pat. No. 5,605,798, WO 92/15712, and WO 97/35033), the probe lengths vary from about 8 to 20 nucleotides depending upon the specific application and method of detection. The number of probes in a sequence-complete set can be described by the equation $4^L$ where L equals the length of the probes. Thus for 8-mer probes, the sequence-complete set has to $4^8$ or 65,536 members. If the number of interrogation sites in the multiplexed determination is about 500, which is a reasonable upper boundary for the number of oligonucleotide probes in a single determination for the types of technologies described above, then the mixture coverage complexity (see discussion below) of the interrogating 8-mer probe mixture would be equal to 500/65,536 or approximately 1/130. In most cases, however, the probes are 15–20 nucleotides in length. While this increased length ensures specificity of the probe for a defined target sequence, it makes the mixture coverage complexity of the probe mixture significantly smaller. Thus, it is clear that for the types of multiplexing methods and applications described above, the interrogating oligonucleotide mixtures are not designed to be sequence complete with regard to target sequence coverage and could not therefore be considered generic reagents.

The object of many array-based sequencing techniques is to determine the "short word" content, i.e., all of the oligonucleotide subsequences present, in the target nucleic acid sequence. For example, in techniques employing hybridization to surface-bound DNA probe arrays, a set of oligonucleotides of a particular length are arranged in spatially distinct locations on a substrate to form an array, and the target sequence is permitted to hybridize to the array (see for example, U.S. Pat. No. 5,202,231, U.S. Pat. No. 5,492,806, and U.S. Pat. No. 5,695,940). The target sequence will bind at locations that contain a short word complementary to one of the short words in its sequence. Others have disclosed methods for probing surface-bound targets with a sequential set of oligonucleotide probes (see for example, U.S. Pat. No. 5,202,231, U.S. Pat. No. 5,492,806, and U.S. Pat. No. 5,695,940). By identifying the hybridization locations, or knowing the identity of the probing oligonucleotide via a fluorescence measurement or the like, the precise short word content of the target nucleic acid sequence may theoretically be determined. This information can then be used to reconstruct the sequence of the target nucleic acid (see for example; Pevzner, P. A., *J Biomolecular Structure Dynamics* 7, 63 (1989), Pevzner P. A., et al., *J Biomolecular StructureDynamics* 9, 399 (1991), Ukkonen, E., *Theoretical Computer Science* 92, 191 (1992)). It is important to emphasize, however, that relatively sequence-complete sets of oligonucleotide probes are required in order to generically determine the short word content an unknown target.

Techniques that identify the short-word content of the target nucleic acid sequence are useful for applications such as de novo sequencing, re-sequencing, mutation detection and mutational change detection. As the length of the target sequence increases, the success rate or success rate with which the analysis may be carried out decreases. Because some of the applications, e.g., mutation detection, require only qualitative information, the success rate may typically be higher than the success rate for an application requiring quantitative information, e.g., de novo sequencing. For example, the presence of a few short word repeats would severely reduce the success rate for de novo sequencing but would have a lesser of an effect on the success rate for mutation detection. In other applications, substantial prior information is available to assist in the interpretation of the short-word content, thus increasing the success rate of the results.

The purpose of the present invention is to determine the short word content of a target nucleic acid sequence using mass spectroscopy. However, the success rate of such an analysis is expected to be relatively low because the presence of a particular mass in the mass spectrum only reveals that one of many possible nucleic acid sequences is present. For example, using only natural nucleotides, the sequence of GGCTTTA is indistinguishable by mass from the sequence of GCTTTAG, and the presence of a mass peak at 2,142 atomic mass units merely reveals that at least one nucleic acid sequence with 3 T's, 2 G's and 1 A and 1 C is present in the mixture. The ambiguity is further confounded by mass coincidences. For example, the mass peak at 2,193 may contain contributions from nucleic acid sequences containing 6 A's and 1 T or 1 A, 2 C's, 3 G's and 1 T. The purpose of the present invention is to reduce these types of ambiguities within the short-word content of a target nucleic acid sequence.

SUMMARY OF THE INVENTION

The invention is directed to reagents and methods for recapitulating a target nucleic acid in the short-word form that can be analyzed by high-resolution mass spectrometry techniques. The methods and reagents utilize generic oligonucleotide precursor mixtures (X-mer precursor mixtures) and enzymatic processes to alter the length, and concomitantly the mass, of only those X-mer precursors within a defined mixture that are complementary to the target nucleic acid.

One aspect of the present invention is a mixture for direct mass spectral analysis of nucleic acids. The mixture comprises natural and mass-modified X-mer precursors having a minimum length of 3 nucleotides. The minimum mixture coverage complexity ($CC_M$) is 56 divided by the number of distinct X-mers in the mixture. The length of the X-mer precursors can be selected independently for each X-mer precursor. The mass number complexity (MNC) of the mixture is greater than the mass number complexity of any natural equivalent of the mixture. Each of the X-mer precursors in the mixture is represented by a single chemical species.

Another aspect of the present invention is a method of analyzing a target nucleic acid sequence. A mixture of X-mer precursors is hybridized to the target nucleic acid sequences. The mixture comprises natural and mass-modified X-mer precursors having a minimum length of 3 nucleotides and a minimum mixture coverage complexity of 56 divided by the number of distinct X-mers in the mixture. The length of the X-mer precursors can be selected independently for each X-mer precursor. Each of the X-mer precursors in the mixture is represented by a single chemical species. The hybrids are processed to alter the mass of the X-mer precursor portions of the hybrids in a target sequence-mediated reaction. The products of the previous step are analyzed via mass spectrometry.

Another aspect of the present invention is directed to a method of analyzing a target nucleic acid sequence having a 3'-end and a 5'-end. The target nucleic acid sequence is hybridized to a multiplicity of nucleic acid probes in an array, which comprises a surface and a multiplicity of nucleic acid sequence probes. Each of the probes comprises a cleavable linker attached to the surface and a nucleic acid sequence having a 3'-end and a terminal 5'-phosphate wherein the 3'-end of the nucleic acid sequence is attached to the cleavable linker. A mixture of X-mer precursors is hybridized to the target nucleic acid sequence. The mixture comprises natural and mass-modified X-mer precursors having a minimum length of 3 nucleotides and a minimum mixture coverage complexity of 56 divided by the number of distinct X-mers in the mixture. The length of the X-mer precursors can be selected independently for each X-mer precursor. Each of the X-mer precursors in the mixture is represented by a single chemical species. The hybridized X-mer precursors located adjacent to the terminal 5'-phosphate are ligated with the surface-bound probe to form a hybridized precursor/probe complex with the target nucleic acid sequence attached thereto. The complex is cleaved at the cleavable linker and analyzed via mass spectrometry.

Another embodiment of the present invention is a kit for carrying out the above method. The kit comprises a mixture as described above, an enzyme having DNA polymerase activity, and a multiplicity of nucleotides selected from the group consisting of natural chain-terminating triphosphates.

Another embodiment of the present invention is a kit for carrying out the above method. The kit comprises a mixture as described above, an enzyme having DNA polymerase activity, and a multiplicity of nucleotides selected from the group consisting of mass-modified chain-terminating triphosphates.

Another embodiment of the present invention is a kit for carrying out the above method. The kit comprises a mixture as described above, an enzyme having DNA polymerase activity, a multiplicity of nucleotides selected from the group consisting of natural chain-terminating triphosphates and a multiplicity of extension nucleotide triphosphates.

Another embodiment of the present invention is a kit for carrying out the above method. The kit comprises a mixture as described above, an enzyme having DNA polymerase activity, a multiplicity of nucleotides selected from the group consisting of mass-modified chain-terminating triphosphates and a multiplicity of extension nucleotide triphosphates.

Another embodiment of the present invention is a kit for carrying out the above method. The kit comprises a mixture as described above, an enzyme having DNA polymerase activity, a multiplicity of nucleotides selected from the group consisting of mass-modified chain-terminating triphosphates, a multiplicity of extension nucleotide triphosphates and a nuclease.

Another embodiment of the present invention is a kit for carrying out a method as described above. The kit comprises a mixture as described above, a DNA polymerase, a multiplicity of nucleotides selected from the group consisting of natural and thiophosphate extension nucleotide triphosphates and mass-modified chain-terminating triphosphates.

Another embodiment of the present invention is a kit for carrying out a method as described above. The kit comprises a mixture as described above, a DNA polymerase, a multiplicity of nucleotides selected from the group consisting of natural and thiophosphate extension nucleotide triphosphates, mass-modified chain-terminating triphosphates and a 5'-exonuclease.

Another embodiment of the present invention is a kit for carrying out a method as described above. The kit comprises a mixture as described above and a DNA ligase.

Another embodiment of the present invention is a kit for carrying out a method as described above. The kit comprises a mixture as described above and a condensing agent.

Another embodiment of the present invention is a kit for carrying out a method as described above. The kit comprises a mixture as described above, a DNA ligase and an array comprising a surface and a multiplicity of nucleic acid sequence probes comprising a cleavable linker attached to the surface and a nucleic acid sequence having a 3'-end and a terminal 5'-phosphate wherein the 3'-end of the nucleic acid sequence is attached to the cleavable linker.

Another embodiment of the present invention is a kit for carrying out a method as described above. The kit comprises a mixture as described above, a condensing agent, an array comprising a surface and a multiplicity of nucleic acid sequence probes comprising a cleavable linker attached to the surface and a nucleic acid sequence having a 3'-end and a terminal 5'-phosphate wherein the 3'-end of the nucleic acid sequence is attached to the cleavable linker.

BRIEF DESCRIPTION OF THE DRAWINGS

FIG. 11 is a sequence of a region of the human p53 gene having known mutation sites.

FIG. 12 depicts a nested set of overlapping 7-mer PEA products corresponding to the 62 nucleotide fragment of the wild type p53 sequence.

FIG. 17 depicts a mass spectra for a PEA analysis of the wild type and G2451C p53 mutant within the 378 nucleotide fragment using natural 6-mer precursors.

FIG. 18 depicts a mass spectra for a PEA analysis of the wild type and G2451C p53 mutant within the 378 nucleotide fragment using the optimized mass-modified 6-mer precursors.

FIG. 19 depicts a set of semi-overlapping 7-me r PEACA products corresponding to the 62 nucleotide fragment of the wild type p53 sequence.

FIG. 20 depicts a mass spectra for a PEACA analysis of the wild type and C2481A p53 mutant within the 62 nucleotide fragment using natural 6-mer precursors.

FIG. 21 depicts a mass spectra for a PEACA analysis of three p53 mutations in the 378 nucleotide fragment.

FIG. 22 depicts a mass spectra for a XLA analysis of the wild type and C2481A p53 mutant within the 62 nucleotide fragment using natural 6-mer precursors.

FIG. 23 depicts a mass spectra for a XLA analysis of the wild type and C2481A p53 mutant within the 378 nucleotide fragment using natural 6-mer precursors.

DETAILED DESCRIPTION OF THE INVENTION

Definitions

Figure 1A:
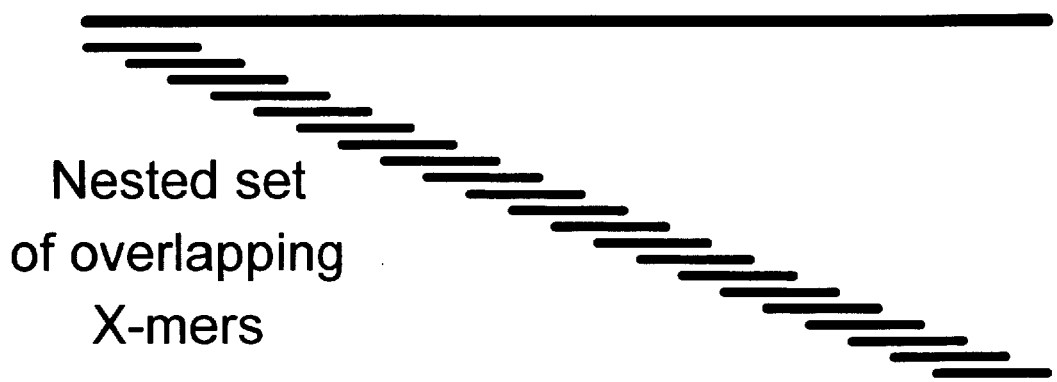
FIGS. 1a–1c is a recapitulation of target sequence by different types of sets of short X-mers.

In this specification and in the claims that follow, reference will be made to a number of terms that shall be defined to have the following meaning:

The term "polynucleotide" or "nucleic acid" refers to a compound or composition that is a polymeric nucleotide or nucleic acid polymer. The polynucleotide may be a natural compound or a synthetic compound. The polynucleotide can have from about 20 to 5,000,000 or more nucleotides. The larger polynucleotides are generally found in the natural state. In an isolated state the polynucleotide can have about 30 to 50,000 or more nucleotides, usually about 100 to 20,000 nucleotides, more frequently 500 to 10,000 nucleotides. It is thus obvious that isolation of a polynucleotide from the natural state often results in fragmentation. It may be useful to fragment longer target nucleic acid sequences, particularly RNA, prior to hybridization to reduce competing intramolecular structures.

The polynucleotides include nucleic acids, and fragments thereof, from any source in purified or unpurified form including DNA (dsDNA and ssDNA) and RNA, including tRNA, mRNA, rRNA, mitochondrial DNA and RNA, chloroplast DNA and RNA, DNA/RNA hybrids, or mixtures thereof, genes, chromosomes, plasmids, cosmids, the genomes of biological material such as microorganisms, e.g., bacteria, yeasts, phage, chromosomes, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site-specific chemical cleavage method.

For purposes of this invention, the polynucleotide, or a cleaved fragment obtained from the polynucleotide, will usually be at least partially denatured or single stranded or treated to render it denatured or single stranded. Such treatments are well known in the art and include, for instance, heat or alkali treatment, or enzymatic digestion of one strand. For example, dsDNA can be heated at 90 to 100° C. for a period of about 1 to 10 minutes to produce denatured material.

The nucleic acids may be generated by in vitro replication and/or amplification methods such as the Polymerase Chain Reaction (PCR), asymmetric PCR, the Ligase Chain Reaction (LCR) and so forth. The nucleic acids may be either single-stranded or double-stranded. Single-stranded nucleic acids are preferred because they lack complementary strands that compete for the oligonucleotide precursors during the hybridization step of the method of the invention.

The phrase "target nucleic acid sequence" refers to a sequence of nucleotides to be identified, detected or otherwise analyzed, usually existing within a portion or all of a polynucleotide. In the present invention the identity of the target nucleotide sequence may or may not be known. The identity of the target nucleotide sequence may be known to an extent sufficient to allow preparation of various sequences hybridizable with the target nucleotide sequence and of oligonucleotides, such as probes and primers, and other molecules necessary for conducting methods in accordance with the present invention and so forth.

The target sequence usually contains from about 30 to 5,000 or more nucleotides, preferably 50 to 1,000 nucleotides. The target nucleotide sequence is generally a fraction of a larger molecule or it may be substantially the entire molecule such as a polynucleotide as described above. The minimum number of nucleotides in the target nucleotide sequence is selected to assure that the presence of a target polynucleotide in a sample is a specific indicator of the presence of polynucleotide in a sample. The maximum number of nucleotides in the target nucleotide sequence is normally governed by several factors: the length of the polynucleotide from which it is derived, the tendency of such polynucleotide to be broken by shearing or other processes during isolation, the efficiency of any procedures required to prepare the sample for analysis (e.g. transcription of a DNA template into RNA) and the efficiency of identification, detection, amplification, and/or other analysis of the target nucleotide sequence, where appropriate.

The term "oligonucleotide" refers to a polynucleotide, usually single stranded, usually a synthetic polynucleotide but may be a naturally occurring polynucleotide. The length of an oligonucleotide is generally governed by the particular role thereof, such as, for example, probe, primer, X-mer, and the like. Various techniques can be employed for preparing an oligonucleotide. Such oligonucleotides can be obtained by biological synthesis or by chemical synthesis. For short oligonucleotides (up to about 100 nucleotides), chemical synthesis will frequently be more economical as compared to the biological synthesis. In addition to economy, chemical synthesis provides a convenient way of incorporating low molecular weight compounds and/or modified bases during specific synthesis steps. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. Methods of oligonucleotide synthesis include phosphotriester and phosphodiester methods (Narang, et al. (1979) Meth. Enzymol 68:90) and synthesis on a support (Beaucage, et al. (1981) Tetrahedron Letters 22:1859–1862) as well as phosphoramidite techniques (Caruthers, M. H., et al., "Methods in Enzymology," Vol. 154, pp. 287–314 (1988)) and others described in "Synthesis and Applications of DNA and RNA," S. A. Narang, editor, Academic Press, New York, 1987, and the references contained therein. The chemical synthesis via a photolithographic method of spatially addressable arrays of oligonucleotides bound to glass surfaces is described by A. C. Pease, et al., Proc. Nat. Acad. Sci. USA (1994) 91:5022–5026.

The term "X-mer" refers to an oligonucleotide that has a defined length, which is usually a sequence of at least 3 nucleotides, preferably, 4 to 14 nucleotides, and usually 5 to 7 nucleotides in length.

The phrase "X-mer precursors", sometimes referred to as "oligonucleotide precursors" refers to a nucleic acid sequence that is complementary to a portion of the target nucleic acid sequence. The oligonucleotide precursors are sequences of nucleoside monomers joined by phosphorus linkages (e.g., phosphodiester, alkyl and aryl-phosphate, phosphorothioate, phosphotriester), or non-phosphorus linkages (e.g., peptide, sulfamate and others). They may be natural or synthetic molecules of single-stranded DNA and single-stranded RNA with circular, branched or linear shapes and optionally including domains capable of forming stable secondary structures (e.g., stem-and-loop and loop-stem-loop structures). The oligonucleotide precursors contain a 3'-end and a 5'-end. The phrase will be denoted by ω.

The term "mixture" refers to a physical mixture of two or more substances. The term will be denoted by Ω.

The phrase "oligonucleotide probe" refers to an oligonucleotide employed to bind to a portion of a polynucleotide such as another oligonucleotide or a target nucleotide sequence. The design and preparation of the oligonucleotide probes are generally dependent upon the sequence to which they bind.

The phrase "oligonucleotide primer(s)" refers to an oligonucleotide that is usually employed in a chain extension on a polynucleotide template such as in, for example, an amplification of a nucleic acid. The oligonucleotide primer is usually a synthetic nucleotide that is single stranded, containing a sequence at its 3'-end that is capable of hybridizing with a defined sequence of the target polynucleotide. Normally, an oligonucleotide primer has at least 80%, preferably 90%, more preferably 95%, most preferably 100%, complementarity to a defined sequence or primer binding site. The number of nucleotides in the hybridizable sequence of an oligonucleotide primer should be such that stringency conditions used to hybridize the oligonucleotide primer will prevent excessive random non-specific hybridization. Usually, the number of nucleotides in the oligonucleotide primer will be at least as great as the defined sequence of the target polynucleotide, namely, at least ten nucleotides, preferably at least 15 nucleotides, and generally from about 10 to 200, preferably 20 to 50, nucleotides.

The phrase "nucleoside triphosphates" refers to nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine (A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common deoxyribonucleoside triphosphates dATP, dCTP, dGTP and dTTP and ribonucleoside triphosphates such as the four common triphosphates rATP, rCTP, rGTP and rUTP. The term "nucleoside triphosphates" also includes derivatives and analogs thereof, which are exemplified by those derivatives that are recognized and polymerized in a similar manner to the underivatized nucleoside triphosphates.

The term "nucleotide" or "nucleotide base" or "base" refers to a base-sugar-phosphate combination that is the monomeric unit of nucleic acid polymers, i.e., DNA and RNA. The term as used herein includes modified nucleotides as defined below. In general, the term refers to any compound containing a cyclic furanoside-type sugar (β-D-ribose in RNA and β-D-2'-deoxyribose in DNA), which is phosphorylated at the 5' position and has either a purine or pyrimidine-type base attached at the C-1' sugar position via a β-glycosol C1'-N linkage. These terms are interchangeable and will be denoted by a b. The nucleotide may be natural or synthetic, including a nucleotide that has been mass-modified including, inter alia, nucleotides having modified nucleosides with modified bases (e.g, 5-methyl cytosine) and modified sugar groups (e.g., 2'-O-methyl ribosyl, 2'-O-methoxyethyl ribosyl, 2'-fluoro ribosyl, 2'-amino ribosyl, and the like).

The term "DNA" refers to deoxyribonucleic acid.

The term "RNA" refers to ribonucleic acid.

The term "natural nucleotide" refers to those nucleotides that form the fundamental building blocks of cellular DNA, which are defined to include deoxycytidylic acid (pdC), deoxyadenylic acid (pdA), deoxyguanylic acid (pdG) and deoxythymidylic acid (pdT) and the fundamental building blocks of cellular RNA which are defined to include deoxycytidylic acid (pdC), deoxyadenylic acid (pdA), deoxyguanylic acid (pdG) and deoxyuridylic acid (pdU). pdU is considered to be a natural equivalent of pdT.

The term "natural nucleotide base" refers to purine- and pyrimidine-type bases found in cellular DNA and include cytosine (C), adenine (A), guanine (G) and thymine (T) and in cellular RNA and include cytosine (C), adenine (A), guanine (G) and uracil (U). U is considered a natural equivalent of T.

The phrase "modified nucleotide" refers to a unit in a nucleic acid polymer that contains a modified base, sugar or phosphate group. The modified nucleotide can be produced by a chemical modification of the nucleotide either as part of the nucleic acid polymer or prior to the incorporation of the modified nucleotide into the nucleic acid polymer. For example, the methods mentioned above for the synthesis of an oligonucleotide may be employed. In another approach a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophor-labeled, and the like and also include phosphorothioate, phosphite, ring atom modified derivatives, and so forth.

The phrase "Watson-Crick base pairing" refers to the hydrogen bonding between two bases, with specific patterns of hydrogen bond donors and acceptors having the standard geometries defined in "Principles of Nucleic Acid Structure"; Wolfram Saenger, Springer-Verlag, Berlin (1984).

The phrase "base-pairing specificity" of a nucleotide base b refers to the number of natural nucleotide bases with which the base will form Watson-Crick base pairs. The term will be denoted by $S_{bp}(b)$. For example, the $S_{bp}(b)$ for the four natural nucleotides are as follows; $S_{bp}(A)=1$, $S_{bp}(G)=1$, $S_{bp}(C)=1$, and $S_{bp}(T)=1$.

The phrase "natural complement of a nucleotide" refers to the natural nucleotide with which a nucleotide most favorably forms a base pair according to the Watson-Crick base pairing rules. If the nucleotide can base pair with equal affinity with more than one natural nucleotide, or most favorably pairs with different natural nucleotides in different environments, then the nucleotide is considered to have multiple natural nucleotide complements.

The phrase "natural equivalent of a nucleotide" refers to the natural complement of the natural complement of the nucleotide. In cases where a nucleotide has multiple natural complements, then it is considered to have multiple natural equivalents.

The phrase "natural equivalent of an oligonucleotide precursor" refers to an oligonucleotide precursor in which each nucleotide has been replaced with its natural nucleotide equivalent. In cases where one or more of the original nucleotides has multiple natural equivalents, then the oligonucleotide precursors will be considered to have multiple natural equivalents, with the equivalents being chosen from all of the possible combinations of replacements. The phrase is denoted by $NE(\omega)$.

The term "nucleoside" refers to a base-sugar combination or a nucleotide lacking a phosphate moiety.

"Chain-terminating nucleoside triphosphate" is a nucleoside triphosphate that is capable of being added to an oligonucleotide primer in a chain extension reaction but is incapable of under going chain extension. Examples by way of illustration and not limitation include the four standard dideoxynucleotide triphosphates, mass-modified dideoxynucleotide triphosphate analogues, thio analogs of natural and mass-modified dideoxynucleotide triphosphates, arabanose, 3'-amino, 3'-azido, 3'-fluoro derivatives and the like.

The phrase "dideoxynucleoside triphosphate" refers to and includes the four natural dideoxynucleoside triphosphates (ddATP, ddGTP, ddCTP and ddTTP for DNA and ddATP, ddGTP, ddCTP and ddUTP for RNA) and mass-modified dideoxynucleoside triphosphates. The term may be denoted by ddNTP.

The phrase "extension nucleoside triphosphates" refers to and includes natural deoxynucleoside triphosphates, modified deoxynucleotide triphosphates, mass-modified deoxynucleoside triphosphates, 5'(α)-phosphothioate, and 5'-N (α-phosphoramidate) analogs of natural and mass-modified deoxy and ribonucleoside triphosphates and the like, such as those disclosed in U.S. Pat. No. 5,171,534 and U.S. Pat. No. 5,547,835, the relevant portions of which are incorporated herein by reference.

The phrase "nucleotide polymerase" refers to a catalyst, usually an enzyme, for forming an extension of a polynucleotide along a DNA or RNA template where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, *E. coli* DNA polymerase (Klenow fragment, 3'–5' exo-), reverse transcriptase, Vent DNA polymerase, Pfu DNA polymerase, Taq DNA polymerase, Bst DNA polymerase, and the like, or RNA polymerases, such as T3 and T7 RNA polymerases. Polymerase enzymes may be derived from any source such as cells, bacteria such as *E. coli*, plants, animals, virus, thermophilic bacteria, and so forth.

"Amplification" of nucleic acids or polynucleotides is any method that results in the formation of one or more copies of a nucleic acid or polynucleotide molecule (exponential amplification) or in the formation of one or more copies of only the complement of a nucleic acid or polynucleotide molecule (linear amplification). Methods of amplification include the polymerase chain reaction (PCR) based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers. The reagents for conducting such an amplification include oligonucleotide primers, a nucleotide polymerase and nucleoside triphosphates such as, e.g., deoxyadenosine triphosphate (dATP), deoxyguanosine triphosphate (dGTP), deoxycytidine triphosphate (dCTP) and deoxythymidine triphosphate (dTTP). Other methods for amplification include amplification of a single stranded polynucleotide using a single oligonucleotide primer, the ligase chain reaction (LCR), the nucleic acid sequence based amplification (NASBA), the Q-beta-replicase method, and 3SR.

The terms "hybridization (hybridizing)" and "binding" in the context of nucleotide sequences are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like.

The term "complementary," "complement," or "complementary nucleic acid sequence" refers to the nucleic acid strand that is related to the base sequence in another nucleic acid strand by the Watson-Crick base-pairing rules. In general, two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G/U or U/G basepairs.

The term "hybrid" refers to a double-stranded nucleic acid molecule formed by hydrogen bonding between complementary nucleotides. The term "hybridize" refers to the process by which single strands of nucleic acid sequences form double-helical segments through hydrogen bonding between complementary nucleotides.

The term "mass-modified" refers to a nucleic acid sequence whose mass has been changed either by an internal change, i.e., by addition, deletion, or substitution of a chemical moiety, to its chemical structure or by an external change, i.e., by the addition of a chemical moiety (atom or molecule) attached covalently, to its chemical structure. The chemical moiety is therefore referred to as a mass-modifying moiety.

The phrase "mass number of an atom" refers to the nucleon number of the most common isotope of the element of interest.

The reported mass for all nucleic acids (i.e. nucleotides, nucleotide precursors, oligonucleotides, X-mer and X-mer products) is calculated using the mass numbers for the most abundant isotopes of the constituent atoms (i.e. C12, N14, H1, O16, P31, I127) and a protonation state which is stable in aqueous solution at pH 7.

The phrase "mass number of an oligonucleotide precursor" refers to the sum of the mass numbers of the constituent atoms of the oligonucleotide precursors. The phrase will be denoted by $z(\omega)$. The phrase "mass number histogram of a mixture of oligonucleotide precursors" $\Omega$ refers to function h from the natural numbers to the natural numbers defined by $h(z)$, where $h(z)$ is the number of oligonucleotide precursors in the mixture $\Omega$ for which $z(\omega)=z$.

The phrase "average ambiguity of a mixture of oligonucleotide precursors" ($A(\Omega)$) refers to the sum of the squares of the values of the mass number histogram of the mixture of oligonucleotide precursors divided by the number of oligonucleotide precursors in the mixture and may be mathematically expressed as:

$$A(\Omega) = 1/N \sum_z h(z)^2$$

The phrase "mass number complexity" (MNC) refers to the number of oligonucleotide precursors in the mixture divided by the average ambiguity of the mixture of oligonucleotide precursors and may be mathematically defined as $$MNC(\Omega)=N/A(\Omega)$$

The phrase "oligonucleotide coverage complexity" $CC_O(\omega)$ may be expressed mathematically as:

$$CC_o(\omega) = 1/4 \sum_{i=1}^{L} S_{bp}(b_i)$$

where L is the number of nucleotide bases in the oligonucleotide precursor and $b_i$ represents the i'th unit of the oligonucleotide precursor.

The phrase "mixture coverage complexity" ($CC_M(\Omega)$) refers to the sum of the coverage complexities of each of the oligonucleotide precursors in the mixture and may be mathematically expressed as:

$$CC_M(\Omega) = \sum_{\omega \in \Omega} CC_o(\omega)$$

The term "binning" refers to the division of a mixture into defined subset mixtures wherein each individual oligonucleotide of the mixture appears in at least one subset mixture.

The term "composite mixture coverage complexity" refers to the coverage complexity of a set of mixtures that is produced by binning and is equal to the mixture coverage complexity of the original unbinned mixture.

The term "composite mass number complexity" refers to the mass number complexity of a set of mixtures that is produced by binning and is equal to the sum of the mass number complexities of the subset mixtures.

The phrase "direct mass spectral analysis" refers to a method of mass spectral analysis that analyzes either the target nucleic acid sequence itself or the complement of the target nucleic acid sequence. The target nucleic acid sequence itself or its complement may be mass modified, contain additional nucleotide bases or be otherwise modified, provided that the target nucleic acid sequence or its complement is actually mass analyzed. However, the phrase does not include mass spectral analysis wherein a mass tag moiety which is indicative of the presence of target nucleic acid sequence is analyzed, such as those indirect methods described in PCT Application WO 95/04160.

The terms "genericity" or "generic" when applied to a method, refers to a method of mass spectral analysis, which may be applied without reference to certain information. The phrase "positional genericity" refers to methods of mass spectral analysis, which do not require a priori information about the presence, location or identity of mutations in the target nucleic acid sequence. The phrase "target genericity" refers to methods of mass spectral analysis that do not require a priori information about the target nucleic acid.

The term "support" or "surface" refers to a porous or non-porous water insoluble material. The surface can have any one of a number of shapes, such as strip, plate, disk, rod, particle, including bead, and the like. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. Binding of oligonucleotides to a support or surface may be accomplished by well-known techniques, commonly available in the literature. See, for example, A. C. Pease, et al., *Proc. Nat. Acad. Sci. USA*, 91:5022–5026 (1994).

The term "mutation" refers to variation in nucleotides between two polynucleotides such as in single nucleotide polymorphisms. In general, the variations occur from individual to individual. The mutation may be a change in the sequence of nucleotides of normally conserved nucleic acid sequence resulting in the formation of a mutant as differentiated from the normal (unaltered) or wild-type sequence. Mutations can generally be divided into two general classes, namely, base-pair substitutions and frameshift mutations. The latter entail the insertion or deletion of one to several nucleotide pairs. A difference of a single nucleotide can be significant so to change the phenotype from normality to abnormality as in the case of, for example, sickle cell anemia.

General Comments

The present invention provides methods and reagents to satisfy the need for more sensitive, more accurate and higher throughput analyses of target nucleic acid sequences. The methods and reagents may be generically applied to generally any target nucleic acid sequence and do not require a priori information about the presence, location or identity of mutations in the target nucleic acid sequence.

The reagents of the invention, which are useful for direct mass spectral analysis of nucleic acids, are mixtures comprising natural and mass-modified X-mer precursors having a minimum length of 3 nucleotides. The minimum mixture coverage complexity ($CC_M$) of the mixtures is 56 divided by the number of distinct X-mers in the mixture. The length of the X-mer precursors can be selected independently for each X-mer precursor. Each of the X-mer precursors in a mixture is represented by a single chemical species.

The methods and reagents of the present invention reduce the ambiguities present in the mass spectral analysis of a target nucleic acid sequence and, thus, increase the power in all applications utilizing mass spectrometry to analyze the sequence of the target nucleic acid. This reduction is accomplished by employing a mixture of natural and mass-modified oligonucleotide precursors having a high level of mass and coverage complexity. This reduction may be further improved by "binning", i.e., employing subsets of the mixtures in at least two reaction mixtures. The results of the separate interrogation with the subset mixtures could then be combined. In this way, the extent of mass overlap among X-mer products is reduced in a given mass analysis while maintaining a high degree of overall coverage complexity of the target.

The mixtures of the invention are generic or universal in the sense that they may be utilized in any application whose goal is to determine sequence information of a target nucleic acid. Furthermore, the mixtures may be designed without reference to any a priori information about the target nucleic acid sequence, including the presence, location or identity of a mutation, for example. However, this is not meant to imply that the mixtures would not be useful in analyzing target nucleic acid sequences wherein some information was known a priori about the sequence. Nor does it imply that prior information about the target cannot be usefully employed in analysis of the resulting mass spectra.

REAGENTS OF THE INVENTION

Oligonucleotide (X-mer) Precursors

The oligonucleotide precursor (X-mer precursor) reagents of the invention are mixtures of natural and mass-modified X-mer precursors having a minimum length of 3 nucleotides and a mixture coverage complexity of about ⅞ when said mixture contains at least 56 distinct X-mer precursors. As the average length of the X-mer precursor increases, the number of distinct X-mers in the mixtures of this invention also increases and the mixture coverage complexity may decrease. The lower limit of the mixture coverage complexity is equal to 56 divided by the number of X-mers in the mixture. The length of the X-mer precursors can be selected independently for each X-mer precursor.

The particular composition of the mixture is determined on a case by case basis and will depend upon the demands of the given application. The composition of a mixture is defined by the equations set forth herein. The mixture coverage complexity is defined as:

$$CC_M(\Omega) = \sum_{\omega \in \Omega} CC_o(\omega)$$

where $CC_O$ is the oligonucleotide coverage complexity of each of the oligonucleotide precursors in the mixture and is defined as:

$$CC_o(\omega) = 1/4L \sum_{i=1}^{L} S_{bp}(b_i)$$

where L is the number of nucleotide bases in the oligonucleotide precursor, $S_{bp}$ is base-pairing specificity and $b_i$ represents the i'th unit of the oligonucleotide precursor.

Examples of mixtures having the specifications described above, by way of illustration and not limitation, include; (1) a mixture $\Omega_1$ consisting of 56 of the possible 64 3-mers ($CC_M(\Omega_1)=7/8$), (2) a mixture $\Omega_2$, consisting of 128 of the possible 256 4-mers ($CC_M(\Omega_2)=1/2$); (3) a mixture $\Omega_3$ consisting of 256 of the possible 1,024 5-mers ($CC_M(\Omega_3)=1/4$); (4) a mixture $\Omega_4$ consisting of 512 of the possible 4,096 6-mers ($CC_M(\Omega_4)=1/8$); (5) a mixture $\Omega_5$ consisting of 1,024 of the possible 4,096 6-mers ($CC_M(\Omega_5)=1/4$); (6) a mixture $\Omega_6$ consisting of 48 5-mers and 512 6-mers ($CC_M(\Omega_6)=11/64$); (7) a mixture $\Omega_7$ consisting of 128 5-mers, 512 6-mers and 128–7mers ($CC_M(\Omega_7)=33/128$); (8) a mixture $\Omega_8$ consisting of 256 5-mers, 1,000 6-mers and 96 7-mers ($CC_M(\Omega_8)=1/2$).

Examples of mixtures that do not conform to the above specifications, by way of illustration and not limitation include; (1) a mixture $\Omega_9$ consisting of 64 of the possible 256 4-mers (($CC_M(\Omega_9)=1/4<56/64$), (2) a mixture $\Omega_{10}$ consisting of 128 of the possible 1,024 5-mers (($CC_M(\Omega_{10})$ $1/8<56/128$), (3) a mixture $\Omega_{11}$, consisting of 384 6-mers and 128-7mers (($CC_M(\Omega_{11})=13/128<56/512$), (4) a mixture $\Omega_{12}$ consisting of 64 5-mers, 256 6-mers and 64 7-mers (($CC_M$ $(\Omega_{12})=33/256<56/384$).

In addition, the reagents of the invention are mixtures of natural and mass-modified X-mer precursors wherein the mass number complexity (MNC) of the mixture is greater than the mass number complexity of any natural equivalent of the mixture. Mass number complexity refers to the number of X-mer precursors in the mixture divided by the average ambiguity of the mixture of X-mer precursors and may be mathematically defined as:

MNC($\Omega$)=N/A($\Omega$)

The average ambiguity of the mixture of X-mer precursors (A($\Omega$)) refers to the sum of the squares of the values of the mass number histogram of the mixture of X-mer precursors divided by the number of X-mer precursors in the mixture and may be mathematically expressed as:

$$A(\Omega) = 1/N \sum_{z} h(z)^2$$

The mass number histogram of a mixture of X-mer precursors (h(z)) refers to function h from the natural numbers to the natural numbers defined by h(z), where h(z) is the number of X-mer precursors in the mixture $\Omega$ for which z($\omega$)=z.

Usually, the MNC of the mixture is at least about 2 times greater, more usually, at least about 10 times greater, and, most preferably, at least about 50 times greater than the mass number complexity of any natural equivalent of the mixture. For example, the mixture of all natural 4,096 6-mers has a MNC of 53 (see discussion below and Table 1). A mixture containing all 4,096 6-mers that are synthesized in a combinatorial manner can have an MNC of 348 which is about 6.5 times that of the natural equivalent. Another mixture in which each X-mer is synthesized individually can have an MNC of 559, which is about 10 times that of the natural equivalent. A mixture where each of the 4,096 6-mers possesses a unique mass would have an MNC of 4,096 which is about 77 times that of the natural equivalent.

The X-mer precursors useful in the method of the invention have a length of at least 3 nucleotide units. Preferably, the X-mer precursors have a length of at least 4 nucleotide units, more preferably, at least 5 nucleotide units and most preferably at least 6 nucleotide units. The length of the X-mer precursor may be selected independently for each X-mer precursor in the mixture. Thus, it is possible to have a single mixture of X-mer precursors having lengths of 5, 6 and 7 nucleotides. As can be seen from the above discussion, the value, and thus the requirements, for mixture coverage complexity decreases as the length of the X-mer precursor increases. In cases where a single mixture possesses more than one length, the mixture's coverage complexity is obtained by summing the coverage indices of the individual oligonucleotides. Thus, in this case, each oligonucleotide's contribution to the coverage complexity of the mixture would depend on its length: shorter oligonucleotides contribute more. It should be noted that using long oligonucleotides can result in loss in genericity. Lower values of mixture coverage complexity may be used only where loss in genericity can be tolerated. Furthermore, the reagents may comprise a set of mixtures of oligonucleotide precursors. In this case, the mixture coverage complexity of any one member of the set may be lower than that described above, so long as the overall complexity of the mixture conforms to the above description.

The X-mer precursors useful in the method of the invention may each be represented by a single chemical species as opposed to being represented by a number of variants of similar chemical species, such as the ladder of reporter products used to represent the nucleotide sequence in the oligonucleotide described in PCT Application WO 95/04160 (Southern). Thus, each X-mer precursor in the mixture of the invention possess a single mass whereas each oligonucleotide in the mixture of WO 95/04160 is associated with a spectra of masses which represent the nucleotide sequence of interest as discussed above. It is important to recognize that the mass-tag approach disclosed by Southern utilizes cleavable mass tags in which only the tagged portion of the tagged oligonucleotides is analyzed in the mass spectrometer. As can be seen from the disclosure herein, this stands in contrast to the present invention, which relies on generating a mass spectra of the oligonucleotide products themselves resulting from a target mediated enzymatic process. Moreover, the mixture of mass-modified X-mers in the present invention is designed such that any given oligonucleotide sequence possesses only a single mass, that is, represents a single chemical species. This in not the case in the mass-tag approach disclosed by Southern. Due to the "ladder tag" design of the Southern approach, each discrete oligonucleotide sequence within the mixture is associated with a "spectrum" of mass entities.

To be useful in the methods of the present invention, it is desirable and often necessary to know which X-mer precursors are present in the mixture. However, it is not absolutely necessary to know the level of each X-mer precursor. With this said however, it is advantageous to be able to control the concentration of each X-mer in the mixture to compensate for differences in duplex thermostabilities (see discussion below).

In one preferred embodiment, the precursor X-mer mixtures are composed of both natural and mass-modified nucleotides. The identity and location of mass-modified nucleotides within the X-mer precursors will depend upon a number of factors. These include: the desired overall mass complexity of X-mer precursor mixture, the desired thermodynamic properties of the X-mer precursor, the ability of an enzyme or set of enzymes (i.e. polymerases and ligases) to accommodate mass-modified nucleotides within the X-mer precursor, and the constraints imposed by the particular synthesis method of the X-mer precursor mixture.

The X-mer precursors may be mass modified either by an internal change, i.e., by addition, deletion, or substitution of a chemical moiety, to its chemical structure or by an external change, i.e., by the addition of a chemical moiety (atom or molecule) attached covalently, to its chemical structure. An X-mer precursor may have both an internal change and an external change, more than one internal change, more than one external change or some combination thereof.

Suitable internal mass modifications include at least one chemical modification to the internucleoside linkage, sugar backbone or nucleoside base of the X-mer precursor. Examples of suitable internally mass-modified X-mer precursors, by way of illustration and not limitation, are those that include 2'-deoxy-5-methylcytidine, 2'-deoxy-5-fluorocytidine, 2'-deoxy-5-iodocytidine, 2'-deoxy-5-fluorouridine, 2'-deoxy-5-iodo-uridine, 2'-O-methyl-5-fluorouridine, 2'-deoxy-5-iodouridine, 2'-deoxy-5(1-propynyl)uridine, 2'-O-methyl-5(1-propynyl)uridine, 2-thiothymidine, 4-thiothymidine, 2'-deoxy-5(1-propynyl)cytidine, 2'-O-methyl-5(1-propynyl)cytidine, 2'-O-methyladenosine, 2'-deoxy-2,6-diaminopurine, 2'-O-methyl-2,6-diaminopurine, 2'-deoxy-7-deazadenosine, 2'-deoxy-6methyladenosine, 2'-deoxy-8-oxoadenosine, 2'-O-methylguanosine, 2'-deoxy-7-deazaguanosine, 2'-deoxy-8-oxoguanosine, 2'-deoxyinosine or the like.

Suitable external mass modifications include mass tagging the X-mer precursors or dideoxy terminators. External mass-modifying moieties may be attached to the 5'-end of the X-mer, to the nucleotide base (or bases), to the phosphate backbone, to the 2'-position of the nucleoside (nucleosides), to the terminal 3'-position and the like. Suitable external mass-modifying moieties include, for example, a halogen, an azido, nitro, alkyl, aryl, sulfur, silver, gold, platinum, mercury, mass moieties of the type, W-R, wherein W is a linking group and R is a mass-modifying moiety and the like.

The linking group W is involved in the covalent linkage between the nucleotide or nucleoside and R and will vary depending upon the nature of the molecules. Functional groups that are normally present or are introduced on the molecules are employed for linking. The linking groups may vary from a bond to a chain of from 1 to 100 atoms, usually from about 1 to 60 atoms, preferably 1 to 40 atoms more preferably 1 to 20 atoms, each independently selected from the group normally consisting of carbon, hydrogen, oxygen, sulfur, nitrogen, halogen and phosphorous. The atoms in the chain may be substituted with atoms other than hydrogen. As a general rule, the length of a particular linking group can be selected arbitrarily to provide for convenience of synthesis and the incorporation of any desired group. The linking groups may be aliphatic or aromatic, although with diazo groups, aromatic groups will usually be involved. The mass modifying R group can consist of the linking group itself, or a separate mass modifying moity can be attached by methods known to those skilled in the art. Common functionalities present in the linking groups forming a covalent bond between the mass modifying moity R and the molecule to be conjugated include alkylamine, amidine, thioamide, ether, carbamate, urea, thiourea, guanidine, azo, thioether, and carboxylate, sulfonate, and phosphate esters, amides and thioesters. For example, where an amine and carboxylic acid or its nitrogen derivative or phosphoric acid are linked, amides, amidines and phosphoramides will be formed. Where mercaptan and activated olefin are linked, thioethers will be formed Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed.

Other suitable mass modifications would be obvious to those skilled in the art, including those disclosed in *Oligonucleotides and Analogues, A Practical Approach*, F. Eckstein (editor), IRL Press, Oxford, (1991); U.S. Pat. No. 5,605,798; and Japanese Patent No. 59-131909, which are incorporated herein by reference.

A primary goal of the invention is to generate either complete mixtures or sets of mixtures that utilize the available mass range of the mass spectrometer with the concomitant goal of decreasing mass overlap among oligonucleotides having different base-pairing patterns (sequences). As should be apparent from the discussion herein, the amount and type of information that is sought in a given analysis dictates the type of X-mer mixture required.

There will next be described three methods for synthesizing X-mer precursor mixtures. This is by way of illustration and not limitation. Each of the methods described herein has certain advantages depending upon the degree of synthetic control over the individual oligonucleotides that is required. All three methods utilize standard phosphoramidite chemistries or enzymatic reactions that are known in the art. It is contemplated that different types of mass-modified nucleotide precursor mixtures may be synthesized for defined types of applications. For example, a defined mixture that is easy and inexpensive to manufacture can be used for extremely high throughput, low resolution type assays. More complex mixtures, which may be more expensive to manufacture, can be reserved for higher resolution type applications.

The X-mer precursors may be synthesized by conventional techniques, including methods employing phosphoramidite chemistry, including both 5'-to-3' and 3'-to-5' synthesis routes. For example, to synthesize all 6-mers requires 4,096 separate synthesis. Using an automated robotic workstation facilitates this process. This method allows for complete synthetic control of each individual X-mer precursor with regard to composition and length. This is necessary for creating X-mer mixtures having the greatest MNC possible. Individual synthesis also allows for QC analysis of each X-mer, which aids in final product manufacturing. Having individual samples of each X-mer also allows defined subset mixtures to be generated to increase the composite resolution. Moreover, it allows each X-mer to be present in the mixture at a specified concentration. This potentially may be helpful in compensating for different thermostabilities that are expected for each X-mer/target duplex.

The X-mer precursors may be synthesized in parallel or in a single synthesis using standard solid-support phosphoramidite chemistry and a defined series of 25% mixtures of each type of A, C, G and T phosphoramidite. For example, synthesis may be performed stepwise starting from a 25% mixture of each 3'-CPG-linked 5'DMT-protected A, G, C, and T nucleoside. For the synthesis of a mixture of all 4,096 6-mers, five bottles containing a 25% mixture of each A, G, C, and T type of phosphoramidite are prepared for use in each of the five condensation reactions. For example, the bottle for the first condensation step contains a 25% molar equivalent of the phosphoramidites corresponding to; 2'-O-methyl-2,6-diaminopurine, 2'-O-methylguanosine, 2'-deoxy-5-iodocytidine and thymidine. The bottle for the second condensation reaction contains a 25% molar equivalent of the phosphoramidites corresponding to; 2'-deoxyadenosine, 2'-deoxy-7-deazaguanosine, 2'-O-methyl-5(1-propynyl)cytidine and 2'-deoxy-5-fluorouridine. Similar 25% mixture of other types of modified A, G, C and T phosphoramidites are created for the three remaining condensation steps.

Although this is a relatively simple approach from a synthetic standpoint, it does impose some mass interdependencies upon the resulting final X-mer mixture. In the example above, all 1,024 6-mer sequences that require an A-type nucleotide at the second position have a 2'-O-methyl-2,6-diaminopurine at that position. All sequences that require a G at the third position have a 7-deazaguanosine and so forth. Thus, although this synthetic scheme does decrease the overall ambiguity relative to the use of natural bases, the resulting positional interdependencies within the mixture limits the resolving power of the final assay. This is apparent from the calculated MNC values for PEA given in Table I. The MNC for the combinatorial 6-mer mixture is significantly greater than that for the natural 6-mer mixture. It is, however, about two-fold lower than that obtained for the individually optimized set which, by definition, must be synthesized individually. It is important to note, however, that multiple combinatorial synthesis may be carried out such that defined subsets of the X-mers are generated in each separate synthesis. The products from the separate syntheses are then mixed together to give a complete mixture. Although there would still exist a defined positional interdependency within a given synthesis mixture, the overall combined mixture may have a greater mass complexity than that of any single combinatorial mixture described above.

In another approach the mass-modified oligonucleotides can be synthesized individually as described in the first method followed by a chemical modification of their 5'-termini with some type of mass tag moiety. Only a small number of discrete mass tags are necessary in order to disperse the masses of resulting natural oligonucleotide mixture throughout the usable mass spectrometer mass range. This method is similar to that disclosed in U.S. Pat. No. 5,605,798, the relevant disclosure of which is incorporated herein by reference. It should be noted that, although the aforementioned patent describes a similar synthesis, it does not describe or suggest the use of mass-tagged oligonucleotides for the type of mass signature analysis described in the present invention.

Effects of X-mer Modifications on Mass Spectroscopic, Thermodynamic, and Enzymatic Properties The composition of the X-mer precursors directly influences the overall specificity and sensitivity of the assay. Moreover, having control over both their design and mode of synthesis allows for the incorporation of modifications that aid in their use in the methods of the invention. For example, the internucleoside linkage on the phosphodiester backbone of the X-mer precursors may be modified. In one embodiment, it is preferred that such chemical modification render the phosphodiester linkage resistant to nuclease digestion. Suitable modifications include incorporating non-bridging thiophosphate backbones, 5'-N-phosphoamidite intemucleotide linkages and the like.

The mass modification may increase the thermodynamic stability of the hybrids formed between the X-mer precursor and target nucleic acid sequence analyte to normalize the thermodynamic stability of the hybrids within the mixture. For example, 2,6-diaminopurine forms more stable base-pairs with thymidine than does adenosine. In addition, incorporating 2'-fluoro-thymidine increase the stability of A-T base pairs whereas incorporating 5-bromo and 5-methyl cytidine increases the stability of G-C base pairs.

The mass modification may decrease the thermodynamic stability of the hybrids formed between the X-mer precursor and target nucleic acid sequence analyte to normalize the thermodynamic stability of the hybrids within the mixture. A-T base pairs can be destabilized by incorporating 2'-amino-nucleosides. Inosine can also be used in place to guanosine to destabilized G-C base pairs. Incorporating N-4-ethyl-2'-deoxycytidine has been shown to decrease the stability of G-C base pairs. Incorporating the latter can normalize the stability of any given duplex sequence to an extent where its stability is made independent of A-T and G-C content (Nguyen et al., *Nucleic Acids Res.* 25, 3095 (1997)).

Modifications that reduce fragmentation of the oligonucleotide due to the ionization processes in mass spectrometry can also be introduced. For example, one approach is a 7-deaza modification of purines to stabilize the N-glycosidic bond and hence reduce fragmentation of oligonucleotides during the ionization process (see, for example, Schneider and Chait, *Nucleic Acids Res* v23, 1570 (1995)). Modification of the 2' position of the ribose ring with an electron withdrawing group such as hydroxyl or fluoro may be employed to reduce fragmentation by stabilizing the N-glycosidic bond (see, for example, Tang, et al., *J Am Soc Mass Spectrom*, 8, 218–224, 1997).

Mass-tagged Chain-Terminating Nucleotides

The use of chain-terminating nucleoside triphosphates such as dideoxynucleoside triphosphates in the present invention for the method of PEA is fundamentally different from that known in the art. The present PEA method utilizes chain-terminating nucleotides as a means of "scoring" hybridization events between the target nucleic acid and a multitude of mass-modified X-mers by shifting the mass of the resulting extension products out of the mass range of the mass-modified X-mer precursors. This specific function dictates that the absolute mass of the chain-terminating nucleotides be greater than the mass range defined by the lightest and heaviest mass-modified X-mer precursor in the mixture. For example, the mass range for an X-mer precursor mixture composed all 6-mers generated from the four natural deoxynucleotides will range from 1,667 atomic mass units (amu) for ($C_6$) to 1,907 amu for ($G_6$). This gives a mass range difference of 240 amu. The masses of the individual natural dideoxynucleotides (the monophosphate form minus the mass of a water molecule) are 296, 312, 272, and 287 amu for pddA, pddG, pddC, pddT respectively. Thus because the absolute mass of each dideoxynucleotide is greater than the mass range for the natural 6-mer mixture, they are sufficient for partitioning the masses of the X-mer precursors and X+1-mer extension products. When, however, the mass range of the X-mer precursors is increased, for example, by the introduction of mass-modifications or by employing X-mers of mixed lengths, then it is desirable to mass-tag the chain-terminating nucleotide so that the masses of all extension products are greater than that of all X-mer precursors.

In one embodiment of the present invention the mass-tagged dideoxynucleoside triphosphates may also possess an additional chemical component that increases the ionization efficiency of the desired extended X-mer relative to the unextended X-mer precursors or any other undesirable components present in the sample mixture. Usually the ionization efficiency is increased by at least a factor of 2, more usually by a factor of 4 and preferably by a factor of 10. Thus, for example, where 6-mers are used for X-mer precursors, the above additional component assists in facilitating the analysis of the 6-mer precursors and 7-mer extension products. Exemplary of such additional chemical components are primary amines, which can act as protonation sites and thus support single positive ion species for MALDI analysis (Tang et al., 1997, supra). It is also possible to incorporate quaternary amines, which possess a fixed positive charge. This class of chemical groups may be incorporated into non-cleavable mass tags using NHS ester chemistry similar to that disclosed by Gut, et aL, in WO 96/27681 Briefly, the succinimide ester of a quaternary ammonium charged species, such as trimethylammonium hexyryl-N-hydroxysuccinimidyl ester is reacted with a nucleoside derivative having a primary aliphatic amino group. A suitable nucleoside is, for example, a known terminator such as the 3'-amino derivatives of the 2'-deoxynucleosides. Other suitable nucleosides would be the 5-[3-amino-1-propynyl]-pyrimidine and 7-deaza-[3-amino-1-propynyl]-purines derivatives similar to those used to generate the fluorescently labeled ddNTPs described by Prober, et al., (*Science*, 238, 336 (1987)).

METHODS OF THE INVENTION

Generating Short Word Content Representations of Target Nucleic Acids

Figure 1B:
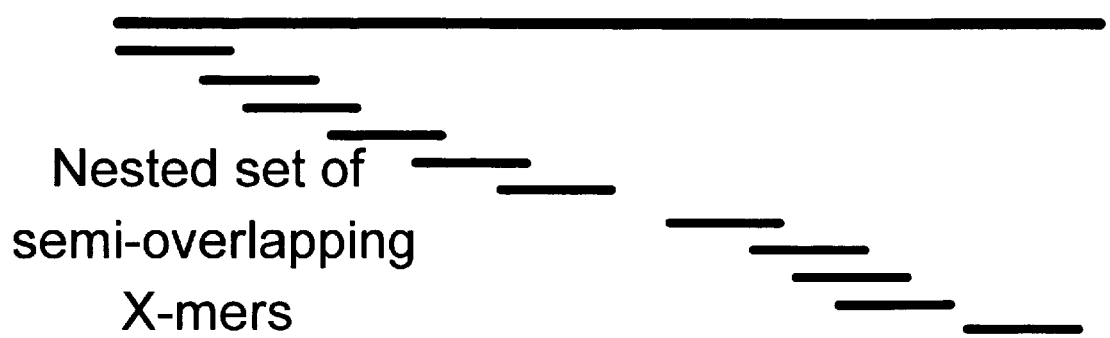
Figure 1C:
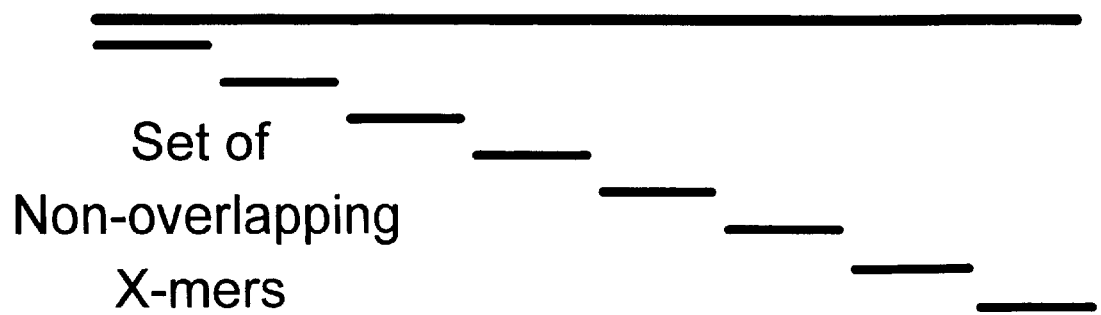

The invention is directed to methods and reagents for recapitulating a target nucleic acid in the form of a set of oligonucleotides (X-mers) that are complementary to the target sequence, and analyzing the set by mass spectroscopy. The set of oligonucleotides represents the "short word" content of the target, which gives defined sequence information about the target. The set of oligonucleotides that represent a target can be of three general types (FIG. 1). The nested set of overlapping X-mers (FIG. 1a) is characterized by having extensive overlap among the X-mers in the set. The nested set of semi-overlapping X-mers (FIG. 1b) has less overlap among the X-mers whereas the non-overlapping set of X-mers (FIG. 1c) has no overlap. For all three types of sets, the X-mer length within a given set need not be constant. In general, the X-mers in the nested set of overlapping X-mers have a length of about 3 to about 18, usually about 5 to about 14, nucleotides. For this set, the overlap is all but one nucleotide along the entire length of the target nucleic acid sequence. In general, the X-mers in the nested set of semi-overlapping X-mers have a length of about 3 to about 18, usually about 5 to about 14, nucleotides. In general, the X-mers in the nested set of non-overlapping X-mers have a length of about 3 to about 18, usually about 4 to about 14, nucleotides. For all three approaches the X-mers sample the entire length of the target nucleotide sequence. The actual number of X-mers generated is generally determined by the length of the target nucleotide sequence and the desired result. The number of X-mers should be sufficient to achieve the goals of the defined application. For example, if the goal is to perform mutation detection, then a sufficient number of X-mers are needed in order to distinguish the X-mer or set of X-mers that encompass the mutation.

General Description of the Methods

One aspect of the present invention is a method of analyzing a target nucleic acid sequence. A mixture of X-mer precursors is hybridized to the target nucleic acid sequences. The mixture comprises natural and mass-modified X-mer precursors having a minimum length of 3 nucleotides. The mixture has a mixture coverage complexity about ⅞ when said mixture contains at least 56 distinct X-mer precursors. As the average length of the X-mer precursor increases, the number of distinct X-mers in the mixtures of this invention also increases and the mixture coverage complexity may decrease. The lower limit of mixture coverage complexity is equal to 56 divided by the number of X-mers in the mixture. The length of the X-mer precursors can be selected independently for each X-mer precursor. The mass number complexity (MNC) of the mixture may be greater than that of any natural equivalent mixture. The hybrids are processed to alter the mass of the X-mer precursor portions of the hybrids in a target sequence-mediated reaction and the product is analyzed by mass spectrometry. The first two steps of the method may be carried out in solution or with surface-bound nucleic acids such as in an array. Solution-based systems may be preferred because they are governed by standard solution mass-action and diffusion processes.

Preparation of the X-mer Mixture

The first step of the method of the invention is preparing a mixture of natural and mass-modified X-mer precursors having an appropriate mass number and coverage complexity for the given application. The X-mer precursor mixture may also possess the attributes described herein regarding ionization and thermodynamic properties. The design and preparation of the X-mer precursor mixture may be carried out as described herein.

Processing Step

The second step of the method of the invention is processing the hybrids to alter the mass of the X-mer precursor portions of the hybrids as described herein. This alteration may be accomplished either by an enzymatic or chemical reaction. Suitable enzymatic techniques include a polymerase extension assay, a ligase assay and the like. Suitable chemical techniques include condensation of activated X-mer precursors using carbodiimides and cyanogen bromide derivatives and the like. The following discussion is a brief description of some of the various processes; a more detailed discussion is set forth below.

Polymerase Extension Assay

Figure 2:
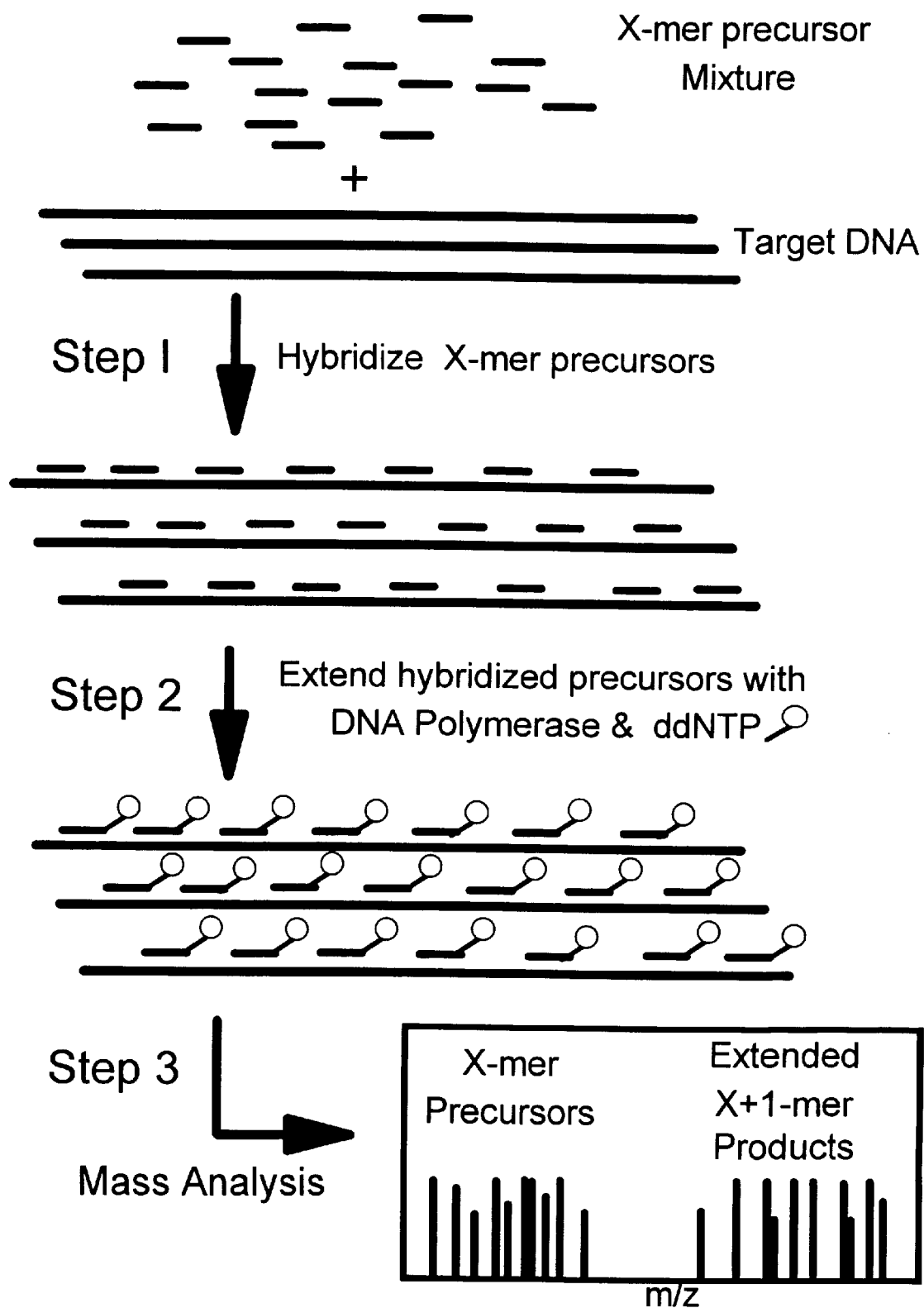
FIG. 2 is a diagram outlining the steps of the Polymerase Extension Assay (PEA).

For the Polymerase Extension Assay (PEA), the hybridized X-mer precursors are extended by polymerizing a single nucleotide at the 3'-end of the hybridized X-mer precursors using a nucleotide polymerase (see FIG. 2). For the Polymerase Extension And Cleavage Assay (PEACA), a form of PEA, the hybridized X-mer precursors are first extended by polymerizing one or more nucleotides at the 3'-end of the hybridized X-mer precursors using a nucleotide polymerase, and then shortened again by digesting the product with a 5' to 3' exonuclease, endonuclease or chemical reagent depending upon the specifics of the method performed (see FIGS. 3 and 4).

Ligase Assay

Figure 5:
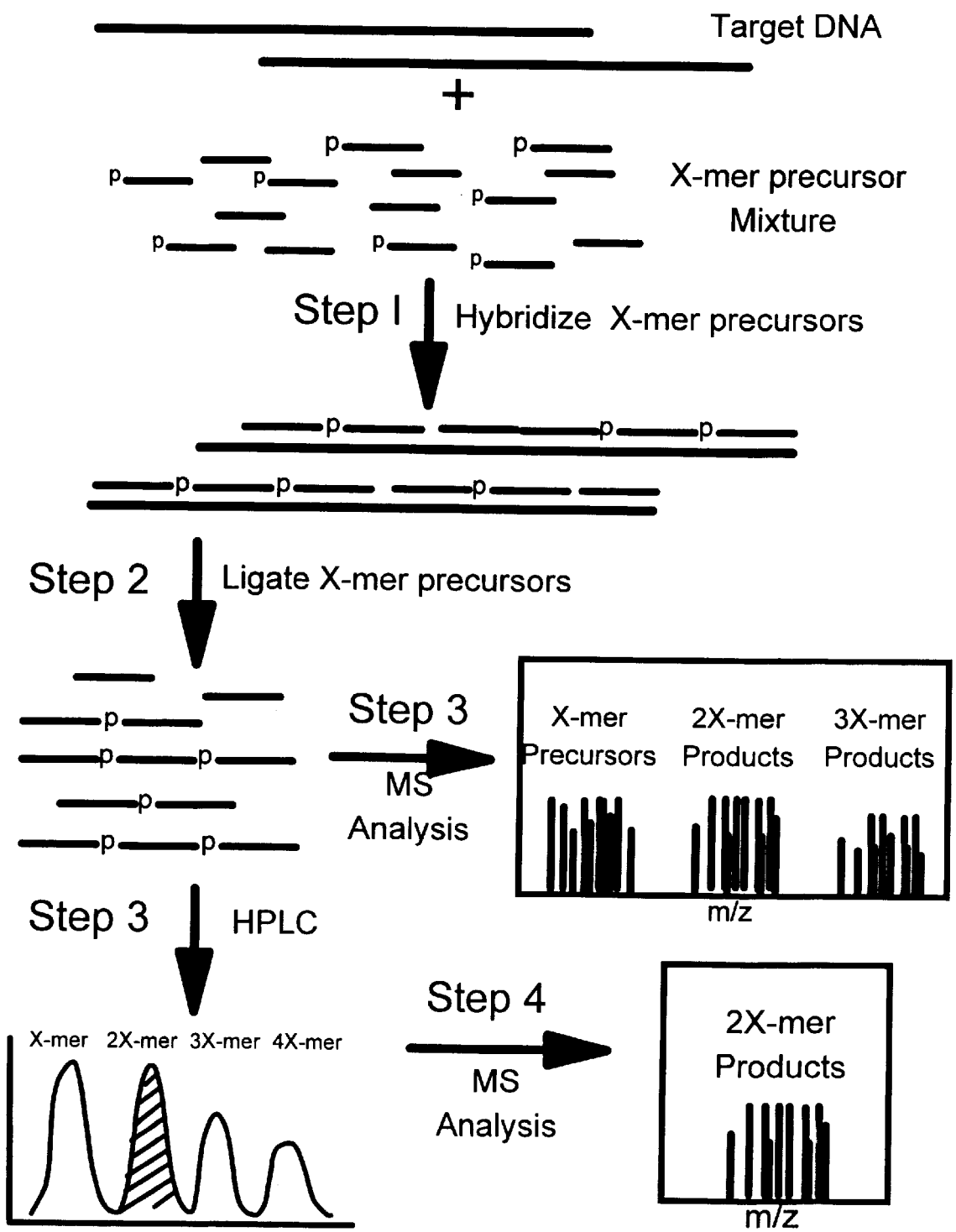
FIG. 5 is a diagram outlining the steps of the X-mer Ligation Assay (XLA).

For the X-mer Ligation Assay (XLA), adjacent hybridized X-mer precursors are ligated together prior to analysis using a ligase (see FIG. 5). It is preferred that the X-mer precursors be of a length sufficient to serve as good substrates for ligation by the ligase yet not too long to serve as templates for ligation of complementary X-mer precursors within the reaction mixture. It should be noted that, although it is preferable that all of the adjacent hybridized X-mer precursors are ligated, it is not a requirement.

Figure 6:
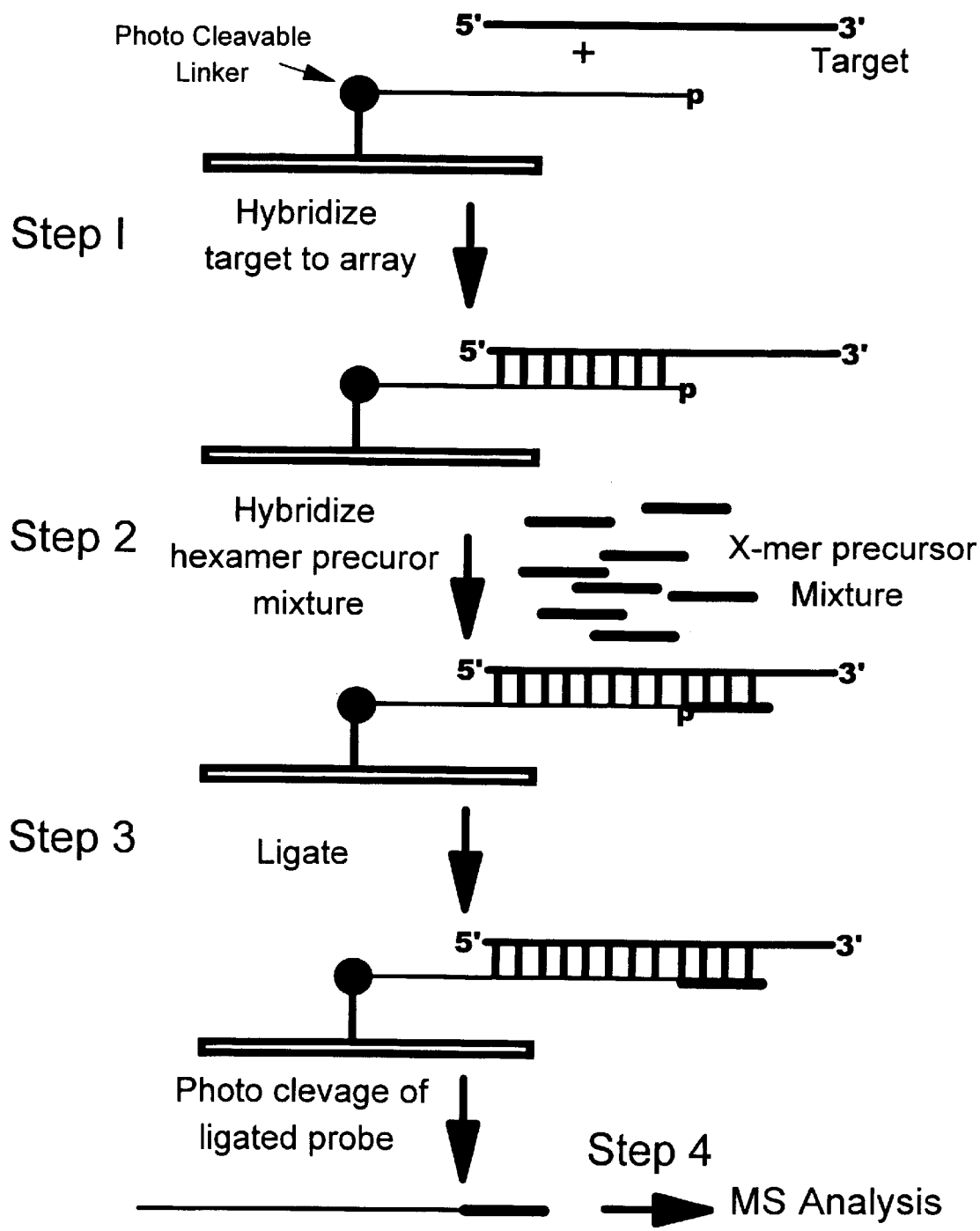
FIG. 6 is a diagram outlining the steps of the Array-based X-mer Ligation Assay (AXLA).

The ligation assay may be conducted with surface-bound arrays (see FIG. 6). The arrays have a surface and a multiplicity oligonucleotide probes attached thereto. The probes contain:

(a) a cleavable linker attached to the surface; and
(b) a nucleic acid sequence having a 3'-end and a terminal 5'-phosphate wherein the 3'-end of said nucleic acid sequence is attached to the cleavable linker. The method includes the following steps:

(1) hybridizing the target nucleic acid sequence to the probes;
(2) adding the mixture of X-mer precursors to the target nucleic acid sequence;
(3) ligating the hybridized X-mer precursors located adjacent to the terminal 5'-phosphate with the surface-bound probe to form a hybridized precursor/probe complex with the target nucleic acid sequence attached thereto;
(4) cleaving the complex at the cleavable linker; and
(5) analyzing the complex in each probe feature or set of features via mass spectrometry.

DETAILED DESCRIPTION OF THE METHODS

The following description is directed to three general methods for generating oligonucleotide sets that represent the short-word content of the target. Each method can generate one or more types of oligonucleotide sets depending upon the reagents used. This description is by way of illustration and not limitation. As mentioned above, the first method is termed "Polymerase Extension Assay" (PEA), the second is termed the Polymerase Extension And Cleavage Assay (PEACA) and the third is termed the "X-mer Ligation Assay" (XLA).

Fundamental to all methods are oligonucleotide (X-mer) mixtures composed of natural and/or mass-modified nucleotides. It should be understood that different sets of mixtures can be designed to generate the different types of sets and thus provide various amounts of target sequence information. By analysis of the mass peaks present in the mass spectra generated in the above methods, and correlation of these peaks with information about the X-mer precursors in the mixture responsible for each mass spectrum, and possibly a priori information about the target sequence, the information sought from the target is determined.

PEA is a generic method for generating nested sets of overlapping and semi-overlapping X-mers. There are three basic steps for this method (FIG. 2). In Step 1, a mixture (or set of mixtures) of X-mers representing either all possible X-mer sequences or subsets thereof are allowed to hybridize at random positions along the target nucleic acid sequence according to Watson-Crick base-pairing rules. In Step 2, the hybridized X-mers are extended by a single nucleotide using a nucleotide polymerase such as a DNA- or RNA-dependent DNA polymerase and a mixture of one or more chain-terminating nucleoside triphosphates such as dideoxynucleotide-triphosphates (MT-ddNTP's). In Step 3, the resulting extended X-mers, i.e., X+1-mer extension products, are analyzed by mass spectroscopy.

The extent of overlap among the X+1-mer products depends upon the sequence completeness of the interrogating X-mer mixture. For example, if all 4,096 6-mers and all four ddNTP's are present in the interrogating mixture, then the maximal overlap among the resulting 7-mer products is possible. Providing a subset of the 4,096 possible 6-mers and/or a subset of the four ddNTP's results in less overlap among the 7-mer products and potential gaps in the sequence coverage.

It is also important that the chain-terminating nucleotides have sufficient mass to effectively partition the X-mer precursor mixture and X+1-mer extension products. It should be noted that, while it is preferable that all of the hybridized X-mer precursors are extended, it is not a requirement. In the present invention the greater the number of hybridized X-mer precursors extended, the more accurate the determination.

The combination of reagents is subjected to conditions under which the X-mers hybridize to the target nucleic acid and are extended by one nucleotide in the presence of a chain-terminating nucleoside triphosphate that is complementary to nucleotide of the target adjacent to the hybridized X-mer. Generally, an aqueous medium is employed. Other polar cosolvents may also be employed, usually oxygenated organic solvents of from 1–6, more usually from 1–4, carbon atoms, including alcohols, ethers and the like. Usually these cosolvents, if used, are present in less than about 70 weight percent, more usually in less than about 30 weight percent.

The pH for the medium is usually in the range of about 4.5 to 9.5, more usually in the range of about 5.5 to 8.5, and preferably in the range of about 6 to 8. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

The reaction is conducted for a time sufficient to produce the extended X+1-mers, which contain a chain terminating nucleoside triphosphate. Generally, the time period for conducting the entire method will be from about 10 to 200 minutes. It is usually desirable to minimize the time period.

The concentration of the nucleotide polymerase is usually determined empirically. Preferably, a concentration is used that is sufficient to extend most if not all of the precursor X-mers that specifically hybridize to the target nucleic acid (see below). The primary limiting factors are generally reaction time and cost of the reagent.

The number of the target nucleic acid molecules can be as low as $10^6$ in a sample but generally may vary from about $10^6$ to $10^{13}$, more usually from about $10^8$ to $10^{12}$ molecules in a sample, preferably at least $10^{-13}$M in the sample and may be $10^{-13}$ to $10^{-6}$M, more usually $10^{-11}$ to $10^{-7}$M. In general, the reagents for the reaction are provided in amounts to achieve extension of the hybridized X-mers. The number of each X-mer precursor molecules is generally $10^{10}$ and is usually about $10^{10}$ to about $10^{13}$, preferably, about $10^{11}$ to about $10^{12}$ for a sample size that is about 10 microliters. The concentration of each X-mer precursor may be adjusted according to its thermostability as discussed above. The absolute ratio of target to X-mer precursor is to be determined empirically. The concentration of the chain-terminating nucleoside triphosphates in the medium can vary depending upon the affinity of the nucleoside triphosphates for the polymerase. Preferably, these reagents are present in an excess amount. The nucleoside triphosphates are usually present in about $10^{-7}$ to about $10^{-4}$ M, preferably, about $10^{-6}$ to about $10^{-5}$ M.

The reaction temperature can be in the range of from about 0° C. to about 95° C. depending upon the type of polymerase used, the concentrations of target and X-mers and the thermodynamic properties of the X-mers in the mixture. For example, at 40 nM target nucleic acid sequence, 40 nM 6-mer, and 7 nM Bst Polymerase, between 20% and 50% of the 6-mer can be extended at 5° C. in 2 hours depending upon the sequence of the 6-mer. Similar extension efficiencies are obtained at 20° C. indicating that the extension efficiency is not solely dependent upon the thermodynamics of the X-mer/target interaction. Importantly, it may be beneficial to cycle the incubation temperature. Cycling could help to expose structured region of the target for X-mer binding and subsequent extension as well as facilitate turnover of the extension products. Thus, the overall sensitivity of PEA could be markedly increased by allowing a given target molecule to act as a template for multiple X-mer binding and subsequent extension reactions. In accordance with this aspect of the invention, one cycle may be carried out at a temperature of about 75° C. to about 95° C. for about 0.1 to 5 minutes, more usually about 0.5 to 2 minutes and another cycle may be carried out at a temperature of about 5° C. to about 45° C. for about 1 to 20 minutes, more usually about 5 to 15 minutes. The number of cycles may be from about 2 to about 20 or more. In general, the cycle temperatures and duration are selected to provide optimization of the extension of the hybridized X-mer of given length.

The order of combining of the various reagents to form the combination may vary. Usually, the sample containing the target polynucleotide is combined with a pre-prepared combination of chain-terminating nucleoside triphosphates and nucleotide polymerase. The X-mers may be included in the prepared combination or may be added subsequently. However, simultaneous addition of all of the above, as well as other step-wise or sequential orders of addition, may be employed provided that all of the reagents described above are combined prior to the start of the reactions.

Figure 3:
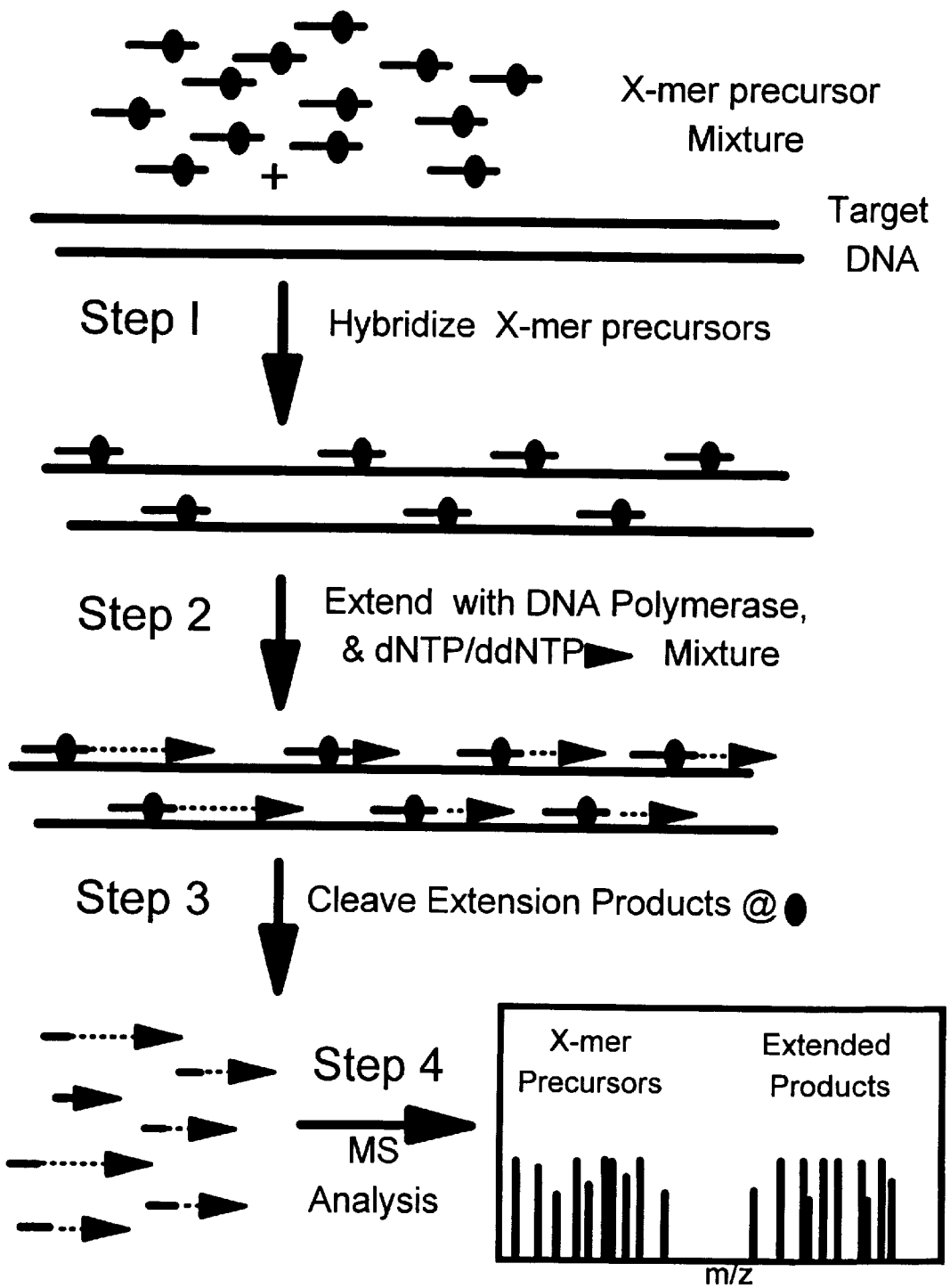
FIG. 3 is a diagram outlining the steps of the Polymerase Extension And Cleavage Assay (PEACA).
Figure 4:
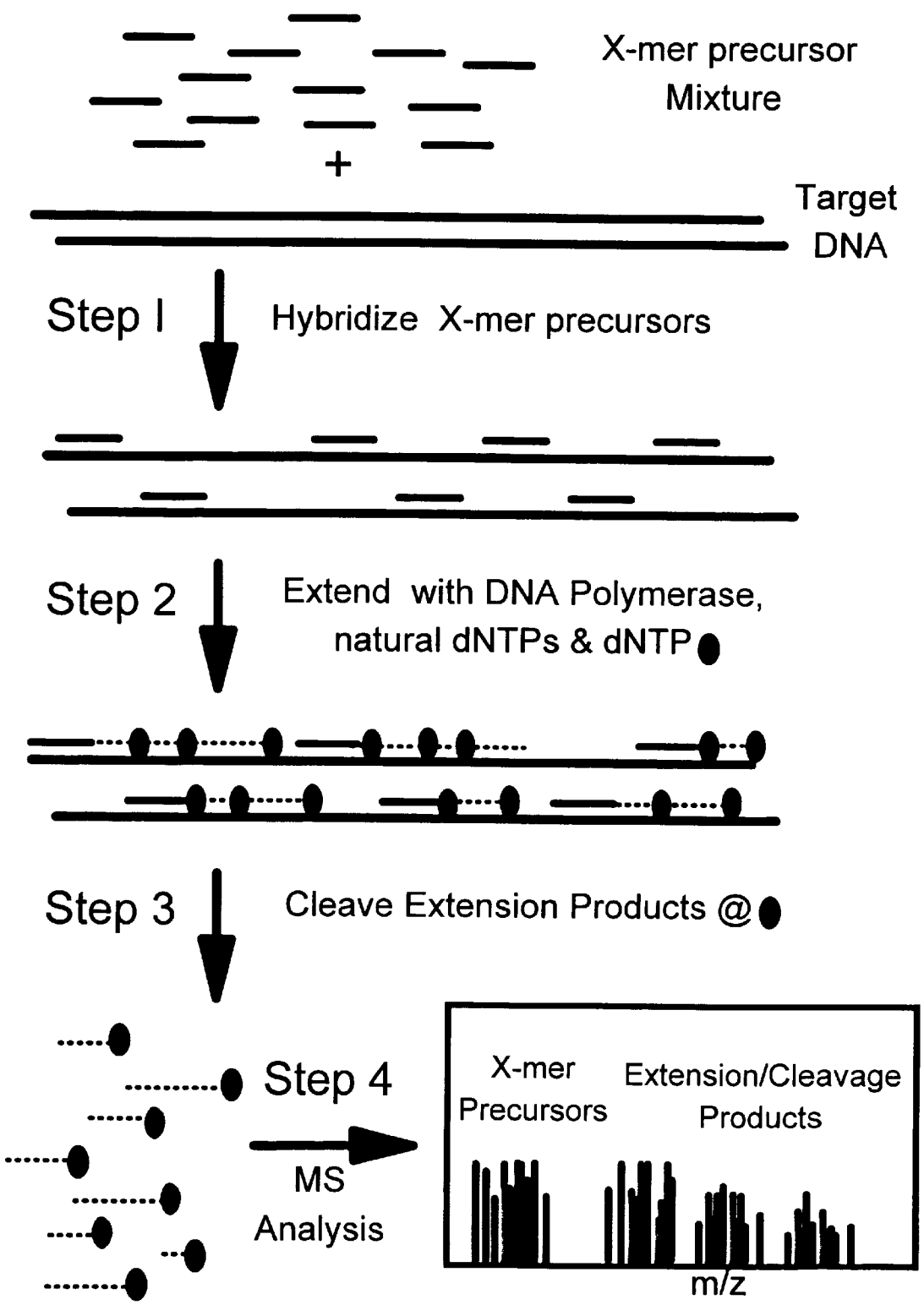
FIG. 4 is a diagram outlining the steps of the Polymerase Extension And Cleavage Assay II (PEACAII).

PEACA is another generic method for generating nested sets of overlapping and semi-overlapping X-mers. There are four basic steps for this method (FIG. 3). In step 1, a mixture of X-mers representing either all possible X-mer sequences or subsets thereof are allowed to hybridize at random positions along the target nucleic acid sequence according to Watson-Crick base-pairing rules. In step 2, the hybridized X-mers are extended using a nucleotide polymerase and a mixture of one or more natural nucleotide triphosphates (dNTPs) and natural or mass-tagged dideoxynucleotide-triphosphates (ddNTPs). In step 3, a portion of the 5' terminus of the X-mer extension products is removed by enzymatic or chemical cleavage. In step 4, the resulting X-mer extension products are analyzed by mass spectroscopy.

PEACA is designed to generate X-mer extension products where the product length is defined by the target sequence and the identity of the dNTPs and chain-terminating nucleotides (i.e. ddNTPs) that are present in the reaction mixture. The extent of potential overlap among the X-mer products depends not only the length but also upon the coverage complexity of the X-mer precursor mixture. Employing X-mer precursor mixtures having a greater coverage complexity result in greater overlap among the extension products. When all four dNTPs and a single chain-termination nucleotide (i.e. ddNTP) are present in the reaction mixture, then increasing the dNTP/ddNTP molar ratio not only increases the length of the extension products but also results in greater potential overlap among the extension products. Conversely, smaller dNTP/ddNTP ratios give shorter extension products and less potential overlap.

In PEACA (FIG. 3), cleavage of some portion of the 5' end is defined by a specified nucleotide within the X-mer precursor. PEACA has the added advantage of allowing for the removal of some portion of the 5' end of the X-mer products using an enzymatic or chemical process. Such a property could be exploited to generate PEACA products having the same length when starting with mixed length X-mer mixtures. This could allow the more A/T rich X-mer precursors to be longer than those that are C/G rich (to compensate for differences in thermostabilities), yet upon cleavage, generate PEACA products having identical or similar lengths. Moreover, the 5' terminus of the X-mer is prone to mis-hybridization with the target and less susceptible to inspection by the polymerase. Thus the PEACA cleavage reaction could be used to remove erroneous information prior to mass analysis.

In the second version of PEACA (PEACA II, FIG. 4), cleavage is defined by a specified nucleotide that is incorporated during the extension process. In this version, no portion of the X-mer precursor is retained in the final X-mer product. In addition to depending upon which dNTPs and ddNTPs are present in the reaction mixture, the product length can also be defined by varying the molar ratio of dNTP/ddNTP when both forms of a given nucleotide are present in a reaction mixture. For example, greater dNTP/ddNTP ratio values will give longer extension products on average. Conversely, smaller dNTP/ddNTP ratios will give shorter extension products.

The conditions for carrying out the PEACA extension reactions are similar to those described above for PEA. The buffer pH, ionic strength, addition of surfactants, temperature (and cycling thereof), polymerase concentration, X-mer concentration, target concentration and dNTP/ddNTP concentrations and ratios are all optimized to reach maximum specificity, extension efficiency and information content.

The following examples of bringing about cleavage of some portion of the 5' end are described next by way of illustration and not limitation. In one approach a cleavage defining nucleotide may be used. The cleavage defining nucleotide can be a ribonucleotide that is susceptible to cleavage by an endoribonuclease such as, for example, ribonuclease A, or by a chemical base such as ammonia or hydroxide and the like. The cleavage defining nucleotide can be a nucleotide that forms a 5'-N-phosphoamidite internucleotide linkage, which can be cleaved by acid such as, for example, trichloroacetic acid or dilute HCl. If the X-mer is composed exclusively of ribonucleotides a deoxyribonuclease can be used such as, for example, DNase I.

The point of cleavage can also be defined by a nucleotide or set of nucleotides that block cleavage by a defined reagent or enzyme. For example, the X-mer can be composed of thiophosphate linkages at the 3' terminus and natural phosphodiester linkages at the 5' terminus. Cleavage of the X-mer with a 5' to 3' exonuclease that is sensitive to thiophosphates, such as T7 gene 6 protein, will degrade the X-mer up to the point of the thiophosphate linkage.

The conditions for conducting the cleavage are those generally known in the art for the above enzymes. Briefly, these conditions are incubation of the enzyme in an appropriate buffer, which may contain a divalent metal ion (if required). Suitable 5' to 3'-exonucleases, that is those enzymes that cleave nucleotides one at a time from the end of a polynucleotide from the 5' to the 3'-end, include, for example, DNA polymerase and T7 Gene 6. Suitable endonucleases, i.e., those enzymes that cleave bonds within a nucleic acid, include, for example, deoxyribonuclease I, ribonuclease A or the like. Suitable chemical reactions for chemical digestion include, for example, those reagents for conducting base or acid catalyzed hydrolysis of phosphate esters and the like such as, for example, hydrochloric acid, trifluoroacetic acid, and the like. The conditions for conducting the above enzymatic or chemical reactions are well known to those skilled in the art and will not be repeated here.

XLA is another generic method for generating nested sets of overlapping and semi-overlapping X-mers. There are three basic steps for this method (FIG. 5). In step 1, a mixture of X-mers representing either all possible X-mer sequences or subsets thereof are allowed to hybridize at random positions along the target nucleic acid sequence according to Watson-Crick base-pairing rules. In step 2, the X-mers that hybridize adjacent to one another are ligated together enzymatically using a ligase such as DNA ligase that assists in the formation of a phosphodiester bond to link two adjacent bases in separate oligonucleotides. Such ligases include, for example, T4 DNA ligase, Taq DNA Ligase, E. coli DNA Ligase and the like. Alternatively, adjacent X-mer 10 precursors may be ligated chemically using a condensing agent. Suitable condensing agents include, for example, carbodiimides, cyanogen bromide derivatives, and the like. In step 3, the resulting ligated nX-mer products are analyzed by mass spectroscopy.

The extent of overlap among the nX-mer products depends upon the sequence completeness of the interrogating X-mer mixture. For example, if all 4,096 6-mers are present in the interrogating mixture, then the maximal overlap among the resulting nX-mer products is possible. Providing a subset of the 4,096 possible 6-mers will result in less overlap among the nX-mer products.

The conditions for carrying out the reactions in this approach are similar to those described above. The pH for the medium is usually in the range of about 4.5 to 9.5, more usually in the range of about 5.5 to 8.5, and preferably in the range of about 6 to 8.

The reaction is conducted for a time sufficient to produce the desired ligated product. Generally, the time period for conducting the entire method will be from about 10 to 200 minutes. It is usually desirable to minimize the time period.

The reaction temperature can vary from 0° C. to 95° C. depending upon the type of ligase used, the concentrations of target and X-mers and the thermodynamic properties of the X-mers in the mixture. As in the case of PEA and PEACA, it may be beneficial to cycle the incubation temperature to help expose structured region of the target for X-mer binding and subsequent ligation as well as to facilitate turnover of the ligated products.

The concentration of the ligase is usually determined empirically. Preferably, a concentration is used that is sufficient to ligate most if not all of the precursor X-mers that specifically hybridize to the target nucleic acid. The primary limiting factors are generally react ion time and cost of the reagent.

The concentration of each X-mer precursor is generally as described above for PEA and may be adjusted according to its thermostability as discussed above. The absolute ratio of target to X-mer precursor is to be determined empirically.

The level of phosphorylation of the 5' terminus of the X-mer mixture can affect the extent of ligation (overall number of ligated products) and the length of ligation products (value of n). The extent and length of ligation can also be controlled by introducing a modification at the 3' terminus of the X-mer mixture that blocks ligation. In one approach two sets of X-mer mixtures are used together in a single ligation reaction mixture. The X-mers in the first X-mer mixture possess a 5' phosphorylated terminus and a 3' blocked terminus (p—y) whereas the X-mers in the second X-mer mixture have both 5' and 3' hydroxyl termini (o—o). This results in only 2X-mer ligation products having the form o—o/p—y. Blocking of the 3' terminus may be accomplished, for example, by employing a group that cannot undergo condensation, such as, for example, an unnatural group such as a 3'-phosphate, a 3'-terminal dideoxy, a polymer or surface, or other means for inhibiting ligation. This approach has great informational advantages because the two sets can be jointly optimized.

The use of modified X-mers to control the extent and length of ligation can be combined with the incorporation of an ionization tag for increased ionization efficiency. The X-mers in the first X-mer mixture possess a 5' phosphorylated terminus and a 3' blocked and tagged terminus (p—z). The X-mers in the second X-mer mixture have both 5' and 3' hydroxyl termini (o—o). This results in only 2X-mer ligation products having the form o—o/p—z. The group represented by z can consist of a single functionality that is serving the dual purpose of both blocking and ionization tagging, such as a quaternary ammonium group connected via the 3'-hydroxyl, or it can represent separate functionalities, such as a 3'-terminal dideoxy for blocking with a separate ionization tag attached to the nucleoside base.

PEA, PEACA and XLA possess a number of desirable attributes. First, all are solution-based systems and are governed by standard solution mass-action and diffusion processes. This stands in contrast to unassisted surface-based array hybridization systems, where the probe is physically attached to the surface and unable to diffuse, thus slowing the kinetics of hybridization. In contrast to surface-bound arrays, it is a characteristic of the present invention that a high multiplicity of oligonucleotides binds along the target sequence. This is likely to increase the overall efficiency of X-mer binding and the subsequent enzymatic reaction. Moreover, because the X-mer precursors are short, they are less likely to form intramolecular structures.

Second, PEA, PEACA and XLA take advantage of highly specific enzymatic processes. In the case of PEA and PEACA, the high degree of specificity of the polymerase for perfect duplexes essentially serves to "proof-read" the hybridization process by extending (and therefore marking for detection) only those primers that have hybridized to the correct target sequence. This "proof-reading" is likely to increase the overall specificity of the assay over that which can be obtained by unassisted hybridization methods. Both the efficiency and specificity of hybridization is likely to be increased by the ligase enzyme in XLA as well.

Third, unlike surface-base array hybridization systems that rely on the detection of the hybridization event itself, PEA, PEACA and XLA can mark for detection even transiently stable primer-target interactions. The lifetime of the interaction between the X-mer precursors and the target only needs to be long enough to be recognized and acted upon by the polymerase or ligase. This allows a given target sequence to act as a template for multiple precursor binding and subsequent extension or ligation reactions. This cycling, and the ability to detect transient events, can increase the overall detection sensitivity of the methods over that which can be obtained using unassisted surface-based hybridization assays. As discussed above, this type of reaction cycling could be externally facilitated by artificially cycling the temperature during the extension or ligation reaction.

Finally, the extension or ligation products resulting from methods have a mass range that is greater than that of the precursor X-mers. Thus, the spectral peaks resulting from unreacted precursors should not interfere with the mass spectral signature of desired extension or ligated products. In the case of PEA and PEACA, it is also contemplated that mass-tagged ddNTP's may be utilized. This allows for greater assay flexibility and enables multiplexing of the mass analysis step. It is also contemplated that ionization tags will be incorporated into the X-mer precursors through a 5' or 3'-linker, directly into the base or sugar or into the chain-terminating nucleotides. These attributes should help to increase the overall sensitivity of the assays and help to simplify or possibly eliminate separation steps, which will facilitate assay automation and sample throughput.

The first three methods described herein are directed to interrogating targets free in solution. However, it is also contemplated that the XLA methodology can be used in conjunction with surface-bound oligonucleotides such as arrays of oligonucleotides to increase the overall resolving power of array systems. The arrays generally involve a surface containing a mosaic of different oligonucleotides that are individually localized to discrete, known areas of the surface. Such ordered arrays containing a large number of oligonucleotides have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations.

The present invention may be practiced using oligonucleotides attached to a support. Referring to FIG. 6, in the present invention arrays of oligonucleotides such as DNA arrays can be generated such that the DNA probes are attached to the surface at their 3' terminus through some type of photo- or chemically-cleavable linker. The linker may be cleavable by light, chemical, oxidation, reduction, acid-labile, base-labile, and enzymatic methods. These surface bound probes also have 5' terminal phosphate. Exemplary of photo cleavable linkers are those based on the o-nitrobenzyl group such as those described in WO 95/04160 and so forth. Exemplary of linkers that are cleavable by reduction are those having a dithioate functionality which can be cleaved by mild reducing agents such as dithiothreitol or β-mercaptoethanol. Exemplary of acid labile cleavable linkers are those containing a 5'-N-phosphoamidite internucleotide linkage or an abasic nucleotide as a component of the linker, and so forth. Exemplary of base labile cleavable linkers are those containing a ribonucleotide as component of the linker and so forth.

Referring to FIG. 6, the Array-based X-mer Ligation Assay (AXLA) involves four steps. In step 1, the target sample is hybridized to the surface-bound probes of the array under conditions that are compatible with the ligation reaction described above. The target nucleic acid can be either unlabeled or labeled with, for example, a fluorescent label and so forth. In step 2, the mixture X-mers (non-phosphorylated) is added to the array and allowed to randomly hybridize along the target according to Watson-Crick base-pairing rules. In step 3, those X-mers that hybridize adjacent to the surface bound oligonucleotides are ligated using a DNA ligase as described above. Since only the surface-bound oligonucleotides have 5'-terminal phosphates, ligation occurs only between those 6-mer X-mers that are hybridized adjacent to a DNA probe, and not between 6-mer X-mers that are hybridized adjacent to one another at other positions along the target. In step 4, the ligated X-mers are then cleaved from the surface and analyzed, feature by feature (or set of features) using mass spectroscopy. The conditions for carrying out the ligation reactions in this approach are similar to those described above.

The oligonucleotide cleavage step and the matrix assisted ionization step may be carried out simultaneously. Although this requires system compatibility between the conditions required for hybridization, oligonucleotide photo-cleavage, and matrix formation and ionization, it eliminates the need to transfer the cleaved product from one reaction vessel such as a microtiter dish to another. Moreover, it minimizes the potential of a ligated product diffusing from one feature into another after the photo-cleavage step but prior to analysis.

In the above mode, the mass number complexity (MNC, see discussion below) is given by the MNC of the X-mer precursor mixture (see discussion below), multiplied by the actual feature count of the array. In this situation, arraying all 6-mer oligonucleotides (4,096 features) and performing XLA with an X-mer mixture results in a total effective feature count of sufficient magnitude to de novo sequence greater than 1 kB DNA fragments. This method can also be combined with non-uniform array architectures to further enhance the information content of the assay. Such non-uniform array architectures include, by way of illustration and not limitation, the incorporation, at defined positions within the X-mers, of either universal bases that pair with all four natural bases or degenerate bases that pair with a defined subset of natural bases. The attributes of these types of architectures, with respect to surface-based hybridization array systems, have been described (Pevzner P. A., et al., *J Biomolecular Structure Dynamics* 9, 399 (1991)).

Design of Precursor X-mer Mixtures

Figure 7A:
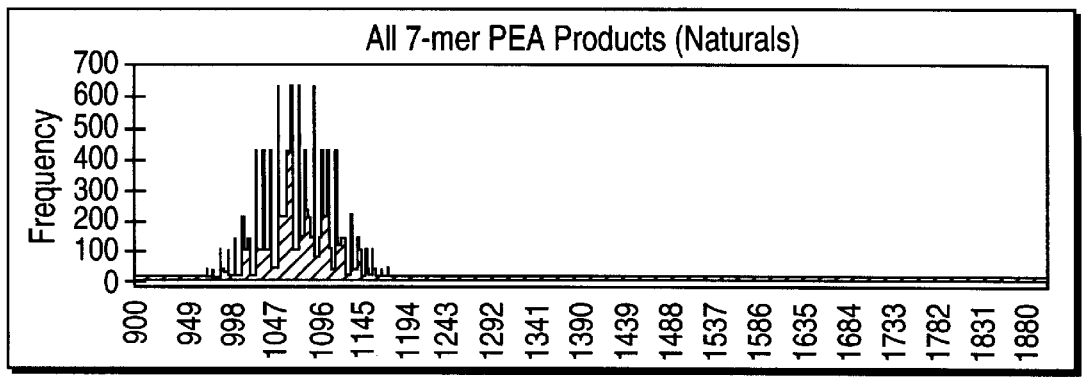
FIGS. 7a–7c is a histogram of all 16,384 7-mer PEA products generated from all natural and individually optimized mass-modified 6-mer precursors.

The power of each type of assay described above is dependent upon characteristics of the X-mer mixtures used to interrogate the target nucleic acid. As discussed above, a high degree of overlap of masses among X-mers having different sequence is an inescapable consequence of X-mers being composed of only four building blocks (see histogram of FIG. 7a). The reagents of the present invention are designed to reduce the ambiguities and, thus, to increase the power in all applications utilizing mass spectrometry to analyze the sequence of the target nucleic acid. This reduction is accomplished by employing a mixture ($\Omega$) of natural and mass-modified X-mer precursor X-mers having a high mass number complexity (MNC ($\Omega$)) and coverage complexity ($CC_M(\Omega)$). Moreover, the mixtures of the invention are generic or universal in the sense that they may be utilized in any application whose goal is to determine sequence information of a target nucleic acid. Furthermore, the mixtures may be designed without reference to any a priori information about the target nucleic acid sequence, including the presence, location or identity of a mutation, for example. However, this is not meant to imply that the mixtures would not be useful in analyzing target nucleic acid sequences wherein some information was known a priori about the sequence or that prior information will not assist in interpretation of the mass spectra.

For specific applications (e.g. mutation detection) the power of an assay can be measured in the length of target nucleic acid within which the problem can be solved (in this specific example, detection of a mutation) with a given success rate, say, 95%. As the power of the assay increases, the length that can be analyzed with a given success rate increases. The same holds true for the success rate with which given lengths can be analyzed. A good benchmark of usability is the length of DNA that can be analyzed on an automated DNA gel electrophoresis sequencer, typically 500 bases or so. A reasonable goal, then, is the analysis of 500 base targets with >95% success rate.

To determine the theoretical power of the assay, it suffices to simulate the X-mer mass spectrum for typical targets, either in a randomly drawn DNA sequence, or genomic DNA drawn from genomic databases, and test whether the desired information can be extracted from the result. This is, however, a time-consuming process, particularly when many alternate assay designs are being considered. Thus, a proxy is created as a measure of the assay power, which is described below. The assay is then optimized using this proxy. Final analysis is performed via assay simulations.

Figure 7B:
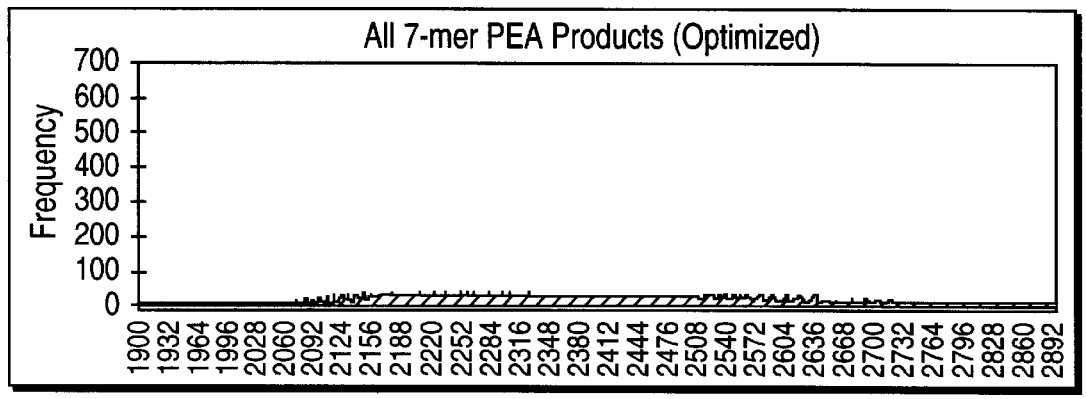
Figure 7C:
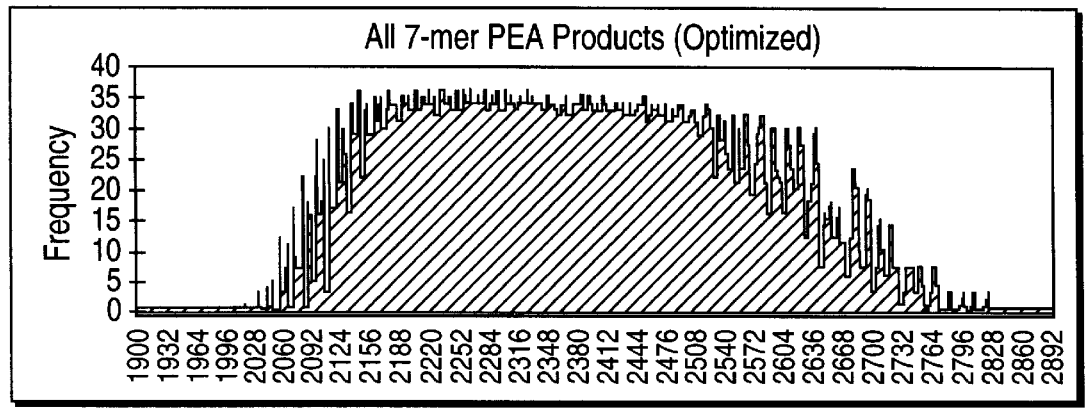

The measure used for optimization is the average ambiguity ($A(\Omega)$) defined above. ($A(\Omega)$) is given by calculating the histogram of the masses of the possible product X-mers in each of the reaction mixtures, then calculating the average number of products that can be confused with each individual product. If the products have length N, and the histogram for mixture i has $h_i(\Omega)$ counts at mass m (i.e. $h_i(\Omega)$) possible products in this mixture have mass m), then the average ambiguity is $sum_i(sum_{m(hi)}(m)^2/(4^N)))$. The optimization process can be seen as attempting to flatten and broaden the histograms as much as possible (see FIGS. 7b and 7c).

It should be noted here that, if complete determination of the short-word content is desired, then the histograms must have no peaks larger than one. In this case, the optimization protocol should be directed at reducing the maximum peak height of the histogram, rather than at reducing ($A(\Omega)$). The mixtures needed for complete short-word resolution are then generated by choosing a single oligonucleotide from each mass and placing them is separate mixtures. This allows the detection of a particular mass in the analysis of a mixture to be unambiguously associated with the chosen X-mer. The number of mixtures is thus given by the maximum peak height of that final histogram.

The mass number complexity (MNC), which is an indication of the power of the assay, is determined by dividing ($A(\Omega)$) into the total number of possible products. This is a useful measure when comparing assays wherein the number of products differs. Our simulations have shown that MNC calculated in this way is monotonically related to the theoretical power to detect mutations, to identify both the type and location of mutations, and to perform genotyping of single nucleotide polymorphisms. It is, thus, appropriate to optimize with this proxy. For reference, surface-bound probe arrays of all n-mer oligonucleotides always have ambiguity of 1, and an effective feature count equal to the number of oligonucleotide probes.

As stated above, the primary goal of the design process is to decrease the average ambiguity ($A(\Omega)$) defined above. If only natural bases are used in a single reaction mixture of 6-mers, then the ambiguity and MNC are fixed (MNC=53) using the formula given above, and are equivalent to the information that could be obtained by uniform fragmentation of the target. Modified bases, such as 5-iodocytidine, 5-fluorouridine and 2'-O-methyl-guanosine can be used to disambiguate oligonucleotides by selectively replacing certain bases with their modifications. For example, if we denote natural bases by ACGT, and a set of modifications by A*G*C*T*, then the oligonucleotide A*TATATT can be distinguished by mass from the oligonucleotide TATATAT. Optimization is thus a process of choosing the appropriate substitutions, given the constraints of the available phosphoramidite bases, the synthetic strategy, the degree of ligation or polymerase extension, the length of the precursor oligonucleotides, and the number of reaction mixtures.

Figure 8:
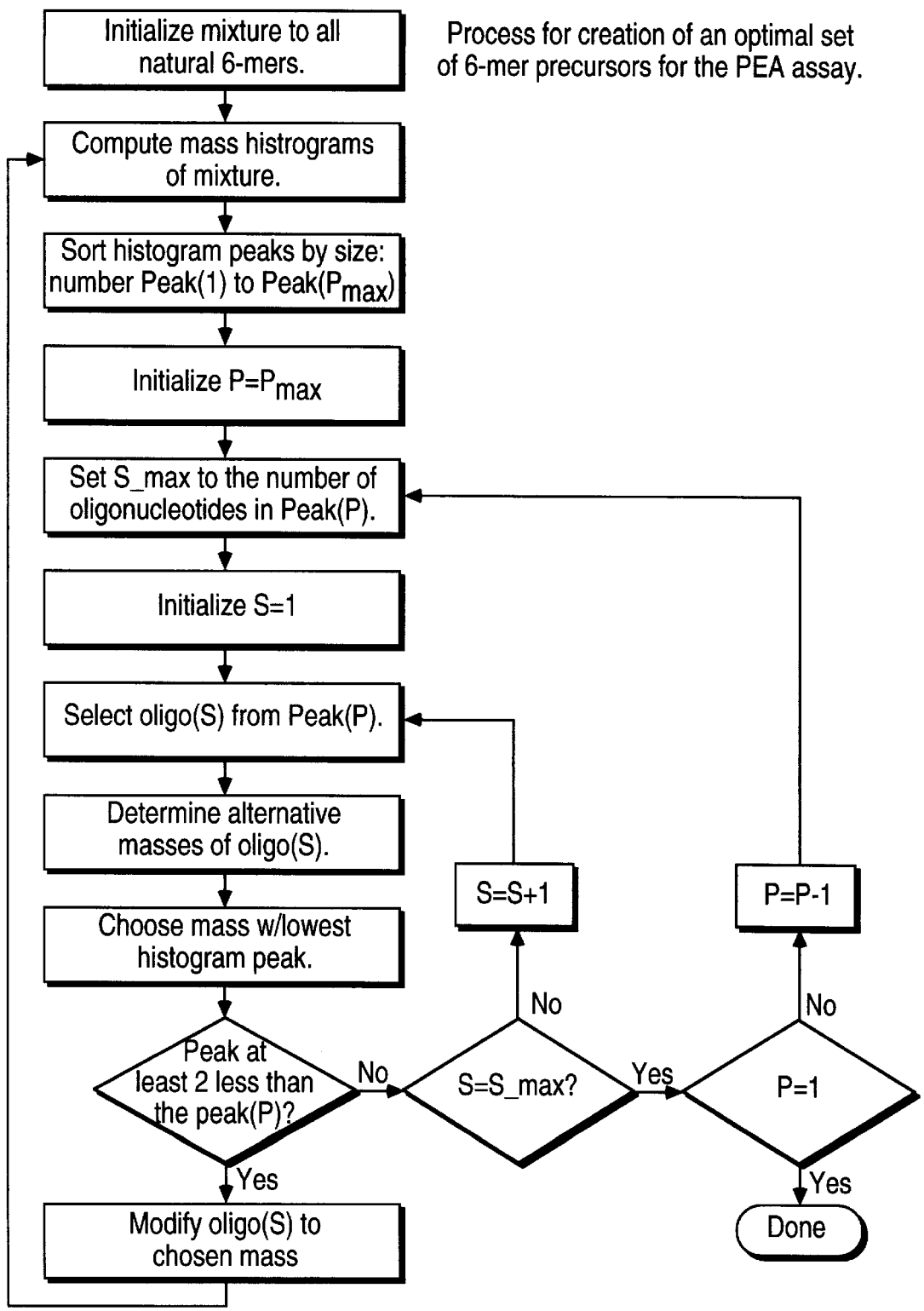
FIG. 8 is a flow chart for optimization of mass-modified X-mer precursors.

FIG. 8 depicts a diagram of an optimization process for PEA wherein the X-mer precursor X-mers are individually synthesized 6-mers. In the process the X-mers are extended by a single nucleotide using a chain-terminating nucleoside triphosphate that is a natural dideoxynucleotide to recapitulate the 7-mer short word content of the target using a single reaction mixture. The optimization process is directed to creating a complete set of 6-mer precursors so as to broaden and flatten the mass histogram of the resulting 7-mer products.

For purposes of illustration the algorithm of FIG. 8 is followed using two adenylate derivatives (A), namely, 2'-deoxyadenosine and 2'-O-methyl-2,6-diaminopurine having masses 330 and 375 respectively, two cytidylate derivatives (C), namely, 2'-deoxycytidine and 2-deoxy-5-iodocytidine having masses 306 and 434 respectively, two guanylate derivatives (G), namely, 2'-deoxyguaosine and 2'-O-methylguanosine having masses 346 and 376 respectively, and two thymidylate (T) derivatives 2'-deoxythymidine and 2'-deoxy-5-iodouridine having mass 321 and 433 respectively.

Begin by considering a mixture of all natural 6-mers. The mass histogram of the mixture is then calculated and the masses are sorted by peak size (frequency). From the peak having the highest frequency (largest number of 6-mers at a given mass), an X-mer is selected and alternative masses are calculated for such X-mer using the set of reagents described above. The X-mer is then reassigned to the alternative mass having the lowest frequency in the mass histogram providing that this reassignment results in a flatter histogram. If no X-mer from highest peak can be reassigned, then X-mers from successively smaller peaks are selected and tested. Once an X-mer has been successfully located and reassigned, the complete mass histogram is recomputed and the process is repeated until no more X-mers can be reassigned according to the criteria described.

As a result of the above optimization process, an average ambiguity of less than 30 is observed with the molecules employed. This is calculated by applying the formula for the average ambiguity described above to the final mass histogram given in FIG. 7b and c. In this case, each peak in the mass histogram contains approximately 30 out of the total possible 16,384 7-mers (see FIG. 7b and c). This results in an MNC of about 559 (see Table I), which is calculated using the equations given and described above.

The value for MNC corresponds, according to simulations, to the ability to detect a single point mutation in about 0.9 kB of single strand DNA target with 95% success rate (see Table I). In this sense, such a mixture can be said to provide information equivalent to a surface-bound hybridization array having 559 features. The advantage of the present invention is that the PEA assay is generic, whereas arrays, in their practical use, are not. This is to say that any 0.9 kB target sequence can be interrogated for point mutations, with an average success rate of 95%, using PEA and the 6-mer precursor mixture described above.

Figure 9:
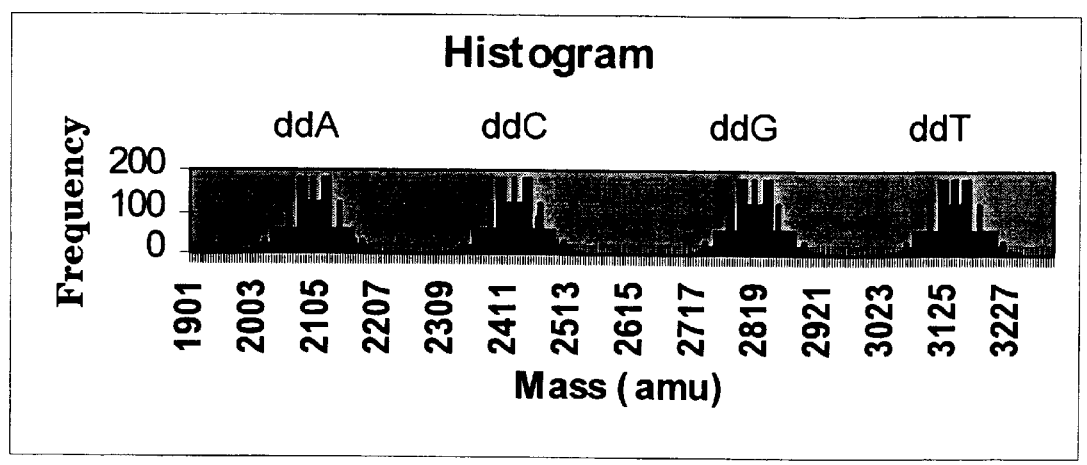
FIG. 9 is a histogram for all 16,384 7-mer PEA products generated from mass-tagged ddNTP's.

For PEA, any division of products into different reaction mixtures also results in a decrease in the ambiguity by approximately the number of mixtures employed. One particularly simple approach is the following: 4 different reaction mixtures are made, each containing all the X-mer precursors and only one of the 4 natural dideoxynucleotide terminators. The peaks in the four mass spectra can then be absolutely assigned to 7-mers ending in the particular extender. In this approach the MNC is increased by a factor of 4 to a value of 2,075. An MNC of this value allows mutation detection in 1.6 kB of double stranded heterozygous PCR product (see Table I). The same effect can be obtained by using four mass-tagged dideoxynucleotide terminators in a single reaction (see FIG. 9). In this case, the mass tags are designed so as to separate mass spectra of the extended 7-mer products according to the identity of the 3' terminal dideoxynucleotide incorporated.

The mass ambiguity may be further reduced by "binning", i.e. interrogating the target with individual subsets of the mixtures and then combining the result of each interrogation during analysis. The mixture may be binned by partitioning so that each individual X-mer is present in a single sub-mixture. Alternatively, the mixture may be binned such that a given X-mer may be present in more than one subset mixture.

The mixtures or subset mixtures of the invention may be designed to reduce the ambiguity of the mass spectrum of the target nucleic sequence to any desired level. The level of ambiguity may be reduced to a minimum level such that the complete short word content of any target nucleic acid sequence may be determined.

Figure 10:
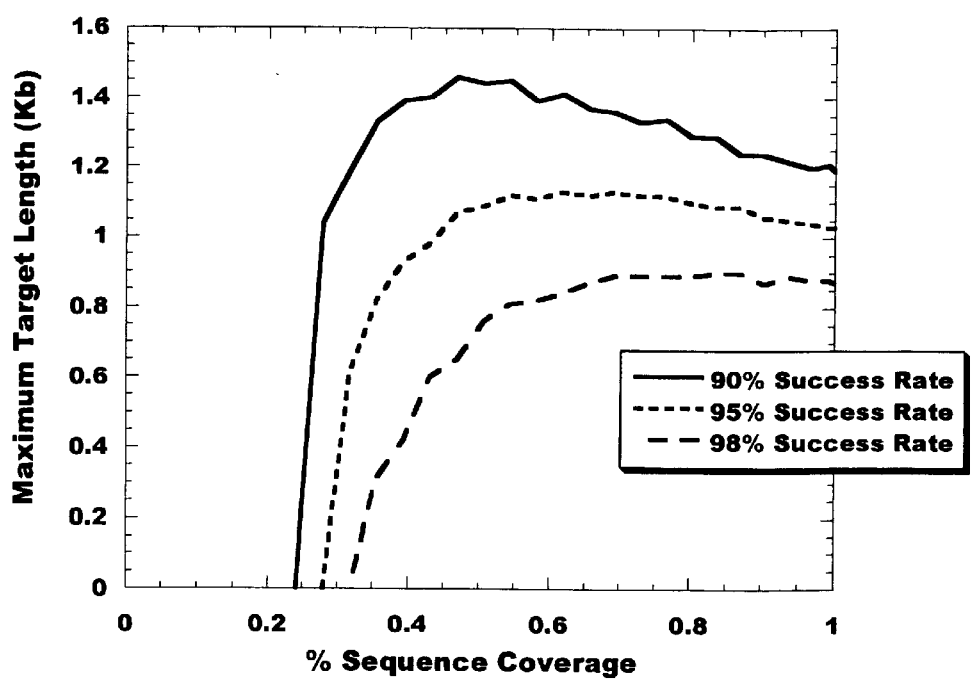
FIG. 10 shows the effect of percent sequence coverage of a 6-mer precursor mixture on the resolving power of PEA at defined success rates.

In addition to the mass number complexity, the resolving power and genericity of PEA depends upon the coverage complexity ($CC_M$ ($\Omega$)) of the X-mer mixture. The simulations show that X-mer mixtures having considerably less than the theoretical maximum $CC_M$ ($\Omega$) retain significant resolving power and genericity. As shown in FIG. 10, up to 50% of total 4,096 6-mers can be removed from the optimized 6-mer mixture without having any significant impact on the length of target in which a single mutation can be detected at a given success rate. As additional X-mers are removed from the mixture, the power of the assay drops off sharply. This effect is due to the balance that must be achieved between having a sufficiently large number of the total X-mers present to maintain genericity of coverage, yet keeping the total number of X-mers present sufficiently small to reduce mass overlap. As expected, a greater percentage of the total X-mers is required for higher success rates. It is anticipated that very high success rates (>99%) can be achieved by interrogating the target with two separate mixtures that have been co-optimized to give orthogonal information.

For XLA, the power of the assay also depends upon the MNC and $CC_M$ ($\Omega$) of the X-mer precursor mixture. As shown in Table I, XLA using a sequence complete 6-mer mixture composed of natural nucleotides gives an MNC of about 200. If, however, XLA is performed using the modified 6-mer mixture, which was optimized for PEA, the MNC is increased about 2 fold to about 400. It should be noted that the optimal (MNC) histogram characteristics of the X-mer precursors for PEA and XLA are different. In general, the optimal histogram of the X-mer precursor for PEA is flat whereas the optimal X-mer histogram for XLA is more bimodal having a bias towards the ends of the mass range. This is because the effect of ligation of the X-mer precursors is to make the histogram of the products concentrate towards the middle of the mass range and thus lower the MNC. To counter this tendency and therefore increase the MNC, it helps to make the X-mer precursor histogram biased towards the lower and upper mass boundaries.

As in the case of PEA, the composite MNC for XLA can be increased by interrogating the target with a multiplicity of defined subsets of X-mer mixtures. However, for XLA, the optimal binning of X-mer precursors is more problematic, as each precursor must have the opportunity to ligate with every other precursor in order to maintain the genericity of the assay. Thus, if S sets of X-mer precursors are made, and the assay reaction ligates X-mer pairs, then S(S-1)/2 reaction mixtures must be created.

As is apparent from the above discussion, the exact optimization process will vary depending upon the type of assay and the details of the information sought. In certain instances, an exhaustive list of all X-mer precursor sets can be made, and the best ones chosen. For example, this strategy may be realistically employed when using the combinatorial synthesis strategy described below for 6-mer precursors, since the total number of possible precursor sets is $2^{24}/6!$ which is a number that can be exhaustively analyzed in reasonable time. In more complicated cases, an optimization algorithm like the one described for PEA is used.

A potential difficulty that may arise is the presence of isotope peaks in the spectrum arising from the isotopic composition of the molecule, which means the amount of particular isotopes for individual atoms in the molecule. For example, natural carbon consists of 99% carbon-12, and 1% carbon-13. A typical 7-mer oligonucleotide has approximately 70 carbon atoms, and thus will produce two nearly equally strong peaks one atomic mass unit apart. One way to address this problem is to rely on sophisticated data analysis methods to deconvolve the isotope peaks. This would involve calculating and/or empirically determining the true mass distribution of possible X-mer extension products using the natural isotope abundance. This information is then used to deconvolve the overlap among differing X-mer isotope peaks. An additional way to address this problem is to partition the X-mer precursors into subset mixtures such that in one subset only even pure extension or ligation primary masses can result and in the other subset only odd primary masses can result. Thus, the predominant N+1 isotope peaks (due primarily to carbon-13) can not interfere with another primary peak because a primary mass can not be generated within the given subset mixture. Alternatively, the X-mer precursors may be manufactured using purified carbon-12. In this approach, the fundamental nucleoside building blocks could be isolated from bacteria or yeast cultured in media containing an enriched or pure C-12 containing nucleoside precursor or carbon source (see for example; Crain, P. F., *Methods Enzymol.* 193, 782 (1990), Nikonowica, D. P et al., *Nucleic Acids Res.* 20, 4501 (1992), Hall, K. B., *Methods Enzymol.* 261, 542 (1995), Macallan et al., *Proc. Natl. Acad. Sci USA*, 95 708 (1998)). The nucleoside could then be converted to suitable phosphoramidites for automated synthesis using standard protocols (see for example; *Oligonucleotides and Analogues, A Practical Approach*, F. Eckstein (editor), IRL Press, Oxford, (1991)). A similar approach may be used with the isotopic peaks introduced by the use of mass modified or ionization tagged nucleotides. The mass or ionization tags could be prepared from isotopically enriched precursors, or alternatively could consist partially or completely of elements that naturally occur largely as one isotope, such as fluorine, phosphorus, or iodine.

Analysis Step

The reaction mixtures, or purified X-mer products, are subsequently analyzed by means of mass spectrometry. The details of the analysis are known in the art and will not be repeated here. Suitable mass spectrometers are described in *Methods in Enzymology*, B. Karger & W. Hancock (editors), Academic Press, San Diego, V270 (1996) and *Methods in Enzymology*, J. McCloskey (editor), Academic Press, San Diego, V193 (1990). These include matrix assisted laser desorption/ionization ("MALDI"), electrospray ("ESI"), ion cyclotron resonance ("ICR"), fourier transform types and delayed ion extraction and combinations or variations of the above. Suitable mass analyzers include magnetic sector/ magnetic deflection instruments in single quadrupole, triple ("MS/MS") quadrupole, Fourier transform and time-of-flight ("TOF") configurations and the like.

It is contemplated that the reaction products may be purified prior to mass spectral analysis using techniques, such as, for example, high performance liquid chromatography (HPLC), capillary electrophoresis and the like (see FIG. 5). Reverse phase HPLC may be employed to separate the extended or ligated X-mer products according to hydrophobicity. The resulting HPLC fractions may then be analyzed via mass spectrometry. Such techniques may significantly increase the resolving power of the claimed methods.

For analysis by MALDI or the like, it is sometimes desirable to modify the X-mer precursors or X-mers to impart desirable characteristics to the analysis. Examples of such modifications include those made to decrease the laser energy required to volatilize the X-mer, minimize the fragmentation, create predominantly singly charged ions, normalize the response of the desired oligonucleotides regardless of composition or sequence reduce the peak width, and increase the sensitivity and/or selectivity of the desired analysis product. For example, modifying the phosphodiester backbone of the X-mers via cation exchange may be useful for eliminating peak broadening due to a heterogeneity in the cations bound per nucleotide unit. Alternatively, the charged phosphodiester backbone of the X-mers can be neutralized by introducing phosphorothioate internucleotide bridges and alkylating the phosphorothioate with alkyliodide, iodoacetamide, β-iodoethanol, or 2,3-epoxy-1-propanol to form a neutral alkylated phosphorothioate backbone. Such alkylation procedures can be used in combination with an ionization tagging scheme as is described in detail in WO 96/27681.

It may also be useful to incorporate nucleotide bases which reduce sensitivity to depurination (fragmentation during mass spectrometry), such as N7- or N9-deazapurine nucleotides, RNA building blocks, oligonucleotide triesters, and nucleotide bases having phosphorothioate functions which can be alkylated as described above and the like.

Data Analysis

After a mass spectrum is obtained, an analysis is performed to yield the information defined by the particular application. For example, mutation detection requires only a qualitative analysis of the data since these types of applications generally involve comparing the mass spectra between a reference sequence and an unknown variant thereof. If mass peak differences exists, then some type of mutation (or sequence difference) is present in the unknown variant.

Mutation identification requires more sophisticated analysis. As is the case in mutation detection, mutation identification generally involves a comparison between a reference sequence and an unknown variant. However, to identify the exact position and identity of a heterozygous mutation within the variant sequence, the following process is applied. First, identify peaks that appear in the sample mass spectrum that do not appear in the wild-type spectrum. Next, from the list of all possible product mixture X-mers, identify those that have masses consistent with the new peaks. Then, identify possible mutation sites that would lead to each of the product mixture X-mers identified being present. If the type of mutation is known (e.g. substitution), then many possible mutation sites may be rejected, and thus many X-mers may be rejected. Finally, test the theoretical spectrum of each mutation for consistency with the observed spectrum.

More sophisticated process can be employed to resolve ambiguities due to differences in extension or ligation efficiencies, ionization efficiencies and isotope effects. Moreover, depending upon the $CC_M$ and MNC of the X-mer precursor mixture, de novo sequence information can also be obtained using algorithms similar to those developed for the sequencing using oligonucleotide arrays (see for example; Pevzner, P. A., *J Biomolecular Structure Dynamics* 7, 63 (1989), Pevzner P. A., et al., *J Biomolecular Structure Dynamics* 9, 399 (1991), Ukkonen, E., *Theoretical Computer Science* 92, 191 (1992)).

KITS OF THE INVENTION

Another aspect of the present invention relates to kits useful for conveniently performing a method in accordance with the invention. To enhance the versatility of the subject invention, the reagents can be provided in packaged combination, in the same or separate containers, so that the ratio of the reagents provides for substantial optimization of the method. The reagents may each be in separate containers or various reagents can be combined in one or more containers depending on the cross-reactivity and stability of the reagents.

In one embodiment a kit comprises a mixture of natural and mass-modified X-mer precursors having a minimum length of 3 nucleotides and a minimum mixture coverage complexity of 56 divided by the number of distinct X-mers in the mixture. The length of the X-mer precursors can be selected independently for each X-mer precursor. Each of the X-mer precursors in the mixture is represented by a single chemical species. The mixture has a mixture has a mass number complexity (MNC) greater than that of any natural equivalent.

In another embodiment a kit comprises a mixture as described above, an enzyme having a nucleotide polymerase activity, and a multiplicity of nucleotides selected from the group consisting of natural chain-terminating triphosphates.

In another embodiment a kit comprises a mixture as described above, an enzyme having a nucleotide polymerase activity, and a multiplicity of nucleotides selected from the group consisting of mass-modified chain-terminating triphosphates.

In another embodiment a kit comprises a mixture as described above, an enzyme having a nucleotide polymerase activity, a multiplicity of nucleotides selected from the group consisting of natural chain-terminating triphosphates and extension nucleotide triphosphates.

In another embodiment a kit comprises a mixture as described above, an enzyme having a nucleotide polymerase activity, a multiplicity of nucleotides selected from the group consisting of mass-modified chain-terminating triphosphates and extension nucleotide triphosphates.

In another embodiment a kit comprises a mixture as described above, an enzyme having a nucleotide polymerase activity, a multiplicity of nucleotides selected from the group consisting of natural chain-terminating triphosphates, extension nucleotide triphosphates and a nuclease.

In another embodiment a kit comprises a mixture as described above, an enzyme having a nucleotide polymerase activity, a multiplicity of nucleotides selected from the group consisting of mass-modified chain-terminating triphosphates, extension nucleotide triphosphates and a nuclease.

In another embodiment a kit comprises a mixture as described above, an enzyme having a nucleotide polymerase activity, a multiplicity of nucleotides selected from the group consisting of natural chain-terminating triphosphates, alpha-thiophosphate nucleotide triphosphates and a 5'-exonuclease.

In another embodiment a kit comprises a mixture as described above, an enzyme having a nucleotide polymerase activity, a multiplicity of nucleotides selected from the group consisting of mass-modified chain-terminating triphosphates, alpha-thiophosphate nucleotide triphosphates and a 5'-exonuclease.

In another embodiment a kit comprises a mixture as described above and a DNA ligase.

In another embodiment a kit comprises a mixture as described above and a condensing agent.

Another embodiment of the present invention is a kit for carrying out a method as described above. The kit comprises a mixture as described above, a DNA ligase and an array comprising a surface and a multiplicity of nucleic acid sequence probes comprising a cleavable linker attached to the surface and a nucleic acid sequence having a 3'-end and a terminal 5'-phosphate wherein the 3'-end of the nucleic acid sequence is attached to the cleavable linker.

In one aspect a kit comprises a condensing agent, an array comprising a surface and a multiplicity of nucleic acid sequence probes comprising a cleavable linker attached to the surface and a nucleic acid sequence having a 3'-end and a terminal 5'-phosphate wherein the 3'-end of the nucleic acid sequence is attached to the cleavable linker.

The kit can further include other separately packaged reagents for conducting the method as well as ancillary reagents and so forth. The relative amounts of the various reagents in the kits can be varied widely to provide for concentrations of the reagents that substantially optimize the reactions that need to occur during the present method. Under appropriate circumstances one or more of the reagents in the kit can be provided as a dry powder, usually lyophilized, including excipients, which on dissolution will provide for a reagent solution having the appropriate concentrations for performing a method in accordance with the present invention. The kit can further include a written description of a method in accordance with the present invention as described above.

The reagents, methods and kits of the invention are useful for, among others, mutation detection, mutation identification, polymorphism analysis, genotyping, de novo sequencing, re-sequencing, gene expression profiling, cDNA clustering and the like.

It should be understood that the above description is intended to illustrate and not limit the scope of the invention. Other aspects, advantages and modifications within the scope of the invention will be apparent to those skilled in the art to which the invention pertains. The following examples are put forth so as to provide those of ordinary skill in the art with examples of how to make and use the method and products of the invention, and are not intended to limit the scope of what the inventors regard as their invention.

EXAMPLES

The following three examples relate to the methods described above using a region of the human p53 gene sequence as the target nucleic acid. FIG. 11 shows a 62 and 378 nucleotide region of the p53 gene with known mutation sites indicated in bold face. For all analyses, the complement of the sequences given in FIG. 11 is used. All of the examples are simulations. Therefore, the specifics with regard to the reaction conditions (i.e. buffer, X-mer and target concentrations, polymerase or ligase type etc.) are not relevant here. Interpretation of these examples depends only upon the mass complexity and coverage complexity of the X-mer precursors, the target length and sequence and the type of assay employed. All examples assume that the reactions proceed as they are described throughout the text and indicated in the figures. Importantly, it is assumed that only those X-mers that are exact complements of the target sequence are actually extended (in the cases of PEA & PEACA) or ligated (in the case of XLA). The main purpose of all of the examples is to illustrate the theoretical power of each assay in terms of the type of mass spectra and information content that each assay would generate.

Example 1 (PEA)

Figure 13:
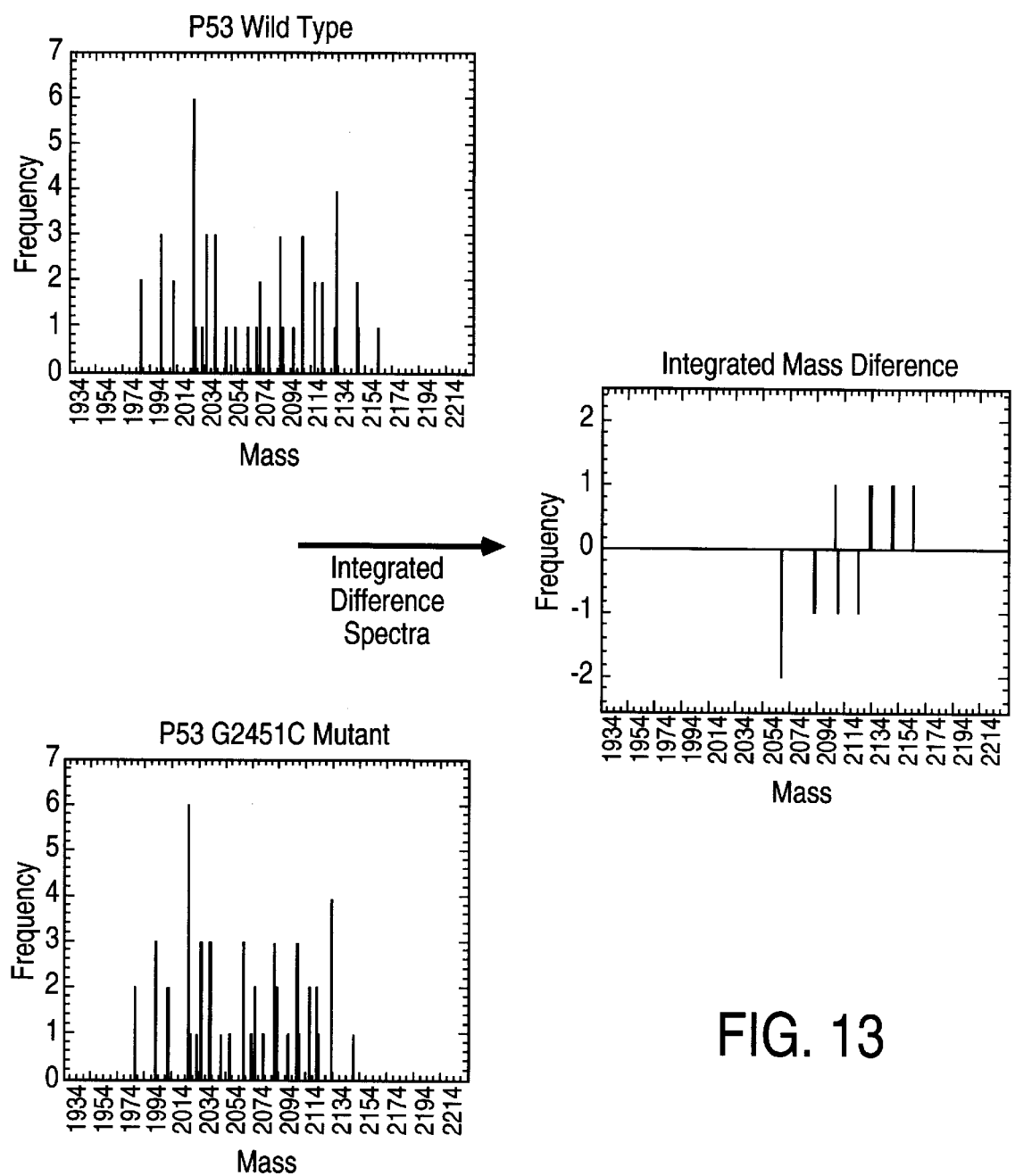
FIG. 13 depicts a mass spectra for a PEA analysis of the wild type and G2451C p53 mutant within the 62 nucleotide fragment using natural 6-mer precursors.

PEA is performed using the 62 nucleotide p53 fragment as the target, all four of the natural ddNTP's, and a sequence-complete set (4,096) of 6-mers composed of the four natural nucleotides. FIG. 12 gives the set of 56 overlapping 7-mer extension products that are expected for the wild type p53 target sequence. The mass spectra of the 7-mer products corresponding to the wild type and the single G2481C mutant is given in FIG. 13. The integrated difference spectra in FIG. 13 reveals which masses differ between the wild type and mutant. Positive difference peaks correspond to masses present in the wild type but not in the mutant whereas negative difference peaks correspond to masses in the mutant but not the wild type. This spectral data would then be interpreted as described above.

Figure 14:
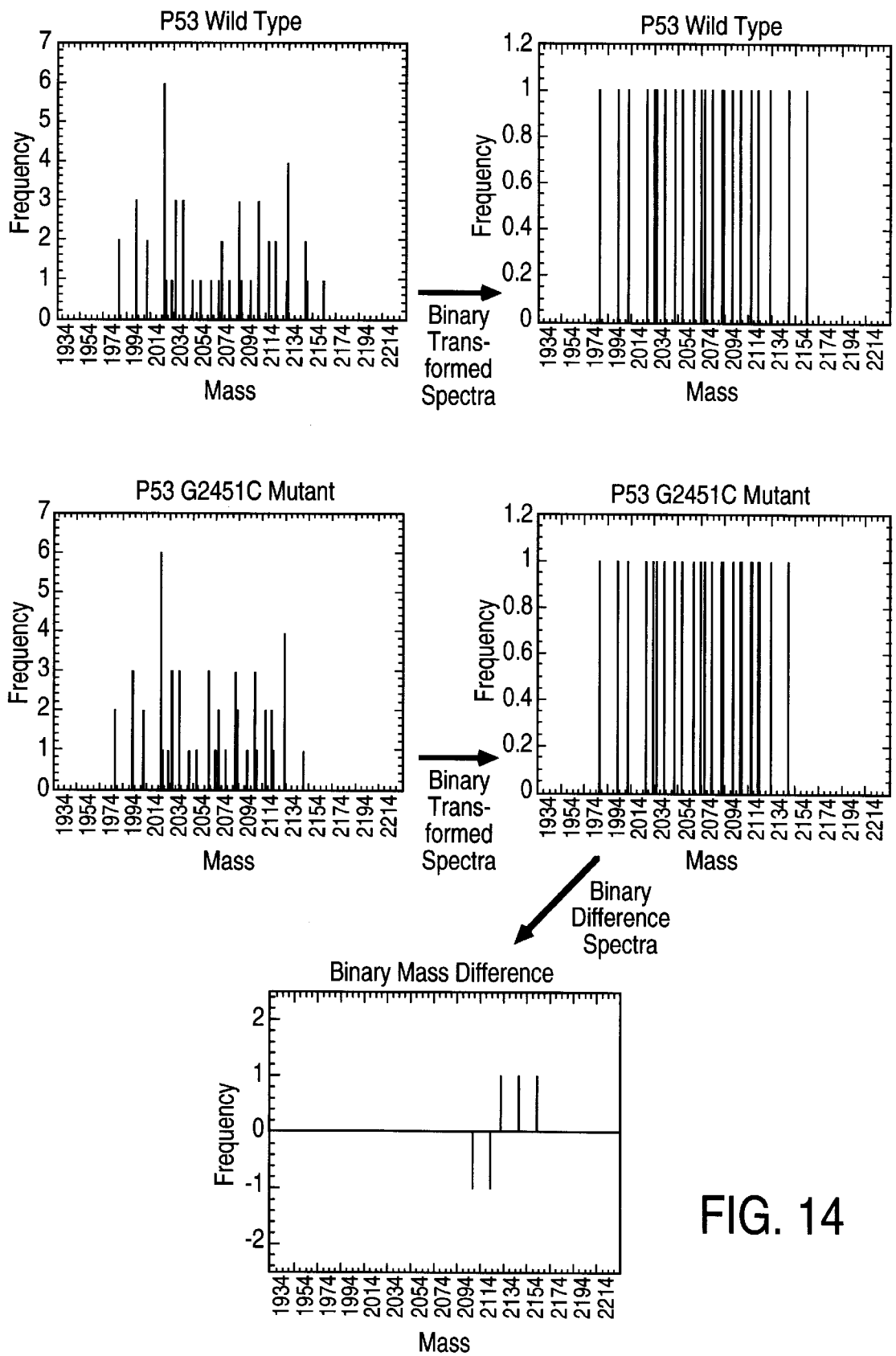
FIG. 14 depicts a binary transformed and difference spectra for a PEA analysis of the wild type and G2451C p53 mutant using natural 6-mer precursors.
Figure 15:
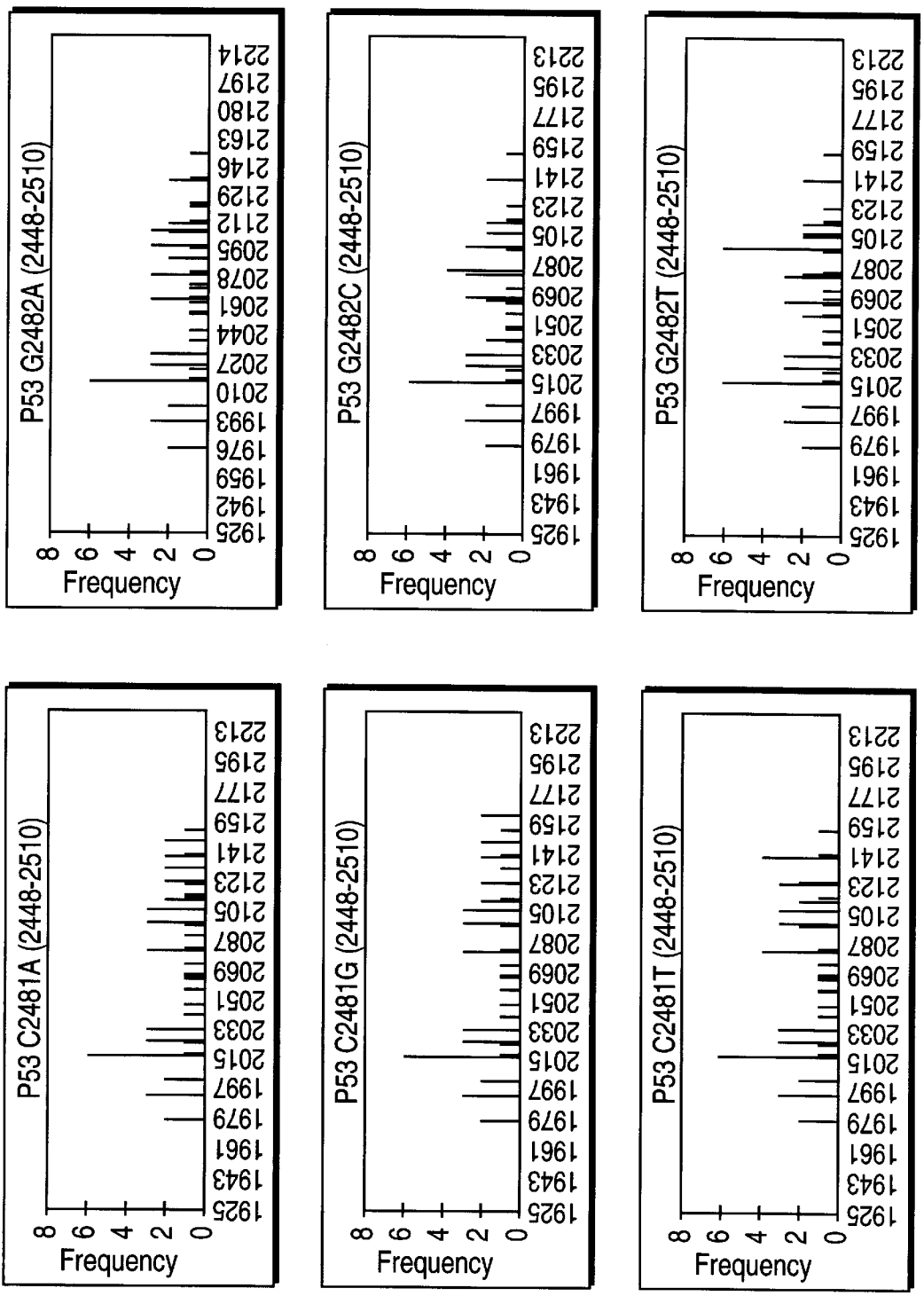
FIG. 15 depicts a mass spectra for a PEA analysis of six p53 mutations using natural 6-mer precursors.
Figure 16:
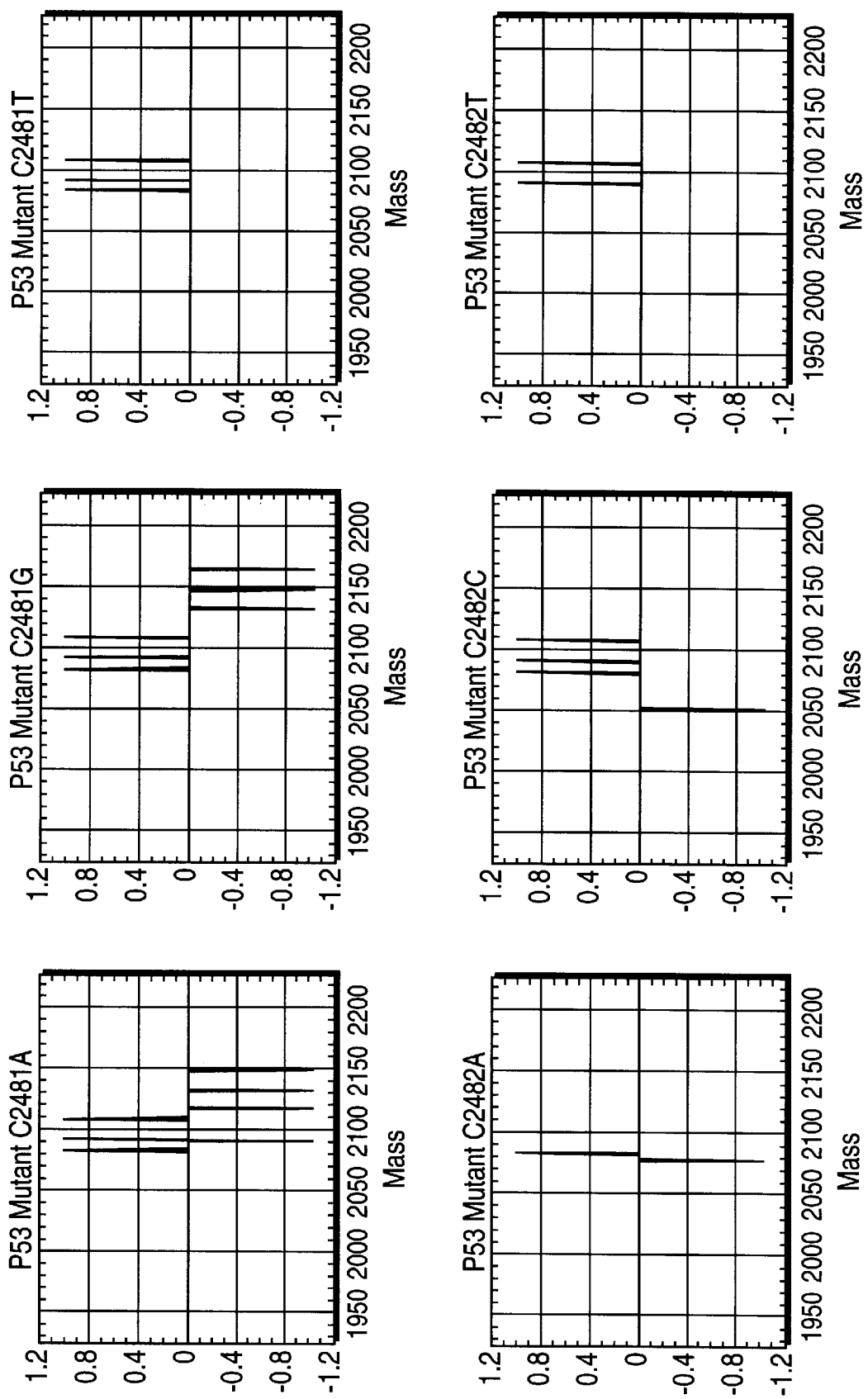
FIG. 16 depicts a binary difference spectra for a PEA analysis of six p53 mutations using natural 6-mer precursors.

It is important to emphasize however, that the information revealed in the integrated difference spectra assumes that the hybridization, extension, ionization, and detection steps for all X-mers occur with equal efficiencies. Because this level of quantitation is unlikely to be the case, even with good optimization, the individual spectral data is reduced to a binary form (FIG. 14). This type of transformation then requires only that the above steps meet a defined threshold level. Although this elimination of the quantitative nature of the data reduces the overall power the assay, the resulting binary difference spectra still reveals differences between the wild type and mutant (FIG. 14). FIG. 15 gives the mass spectra resulting from PEA for all three possible mutations at positions 2481 and 2482 within the 62-nucleotide p53 fragment. As shown in FIG. 16, the binary difference spectra is sufficiently powerful to reveal all six mutations.

When the C2481A mutation is interrogated by PEA within the 378-nucleotide p53 fragment, the resulting binary difference spectra reveals only a single mass difference (FIG. 17). However, when the same interrogation is performed using the individually optimized mass-modified 6-mer mixture described above, the resulting difference spectra reveals six mass differences (FIG. 18). This illustrates the increased power available to this assay when mass-modifications are made to the precursors.

It should be emphasized that the above result is generic—the selection of X-mer precursors was made without using any information about the particular target to be analyzed. As indicated in Table 1, PEA analyses using the individually optimized 6-mer mixture reveals at least one binary mass difference for a single mutation within a 890 nucleotide long target with a success rate of 95%. If a higher success rate is desired, a shorter length of target that can be interrogated is used (see FIG. 10). Longer targets or higher success rates are accessible using PEA if the target is interrogated with either an orthogonal set of X-mer mixtures or with each ddNTP in a separate reaction (see Table 1).

Example 2 (PEACA)

The 62 nucleotide p53 fragment is interrogated by performing four separate PEACA analyses, each containing a defined set of X-mers, dNTP's and ddNTP's. Reaction (A) contains all 6-mers having the form $X_1X_2X_3rA_4X_5X_6$ (where rX is a ribonucleotide), dGTP, dCTP, dTTP and ddATP. Likewise the (G) reaction contains all 6-mers having the form $X_1X_2X_3rG_4X_5X_6$ (where rG is a ribonucleotide), dATP, dCTP, dTTP and ddGTP and so forth. The expected result of this process is a set of semi-overlapping X-mer products having variable lengths (FIG. 19). The resulting composite mass spectra (all four reactions mixed together) for both the wild type and single C2481A mutant are given in FIG. 20. The binary difference spectra reveals seven mass peak differences which are indicative of the given mutation.

It is important to note that the PEACA method results in 4-mer cleavage products ($X_1X_2X_3A_4$, $X_1X_2X_3G_4$, $X_1X_2X_3C_4$, and $X_1X_2X_3T_4$) that are not indicative of the target sequence. Thus, all informative information in the binary difference spectra is constrained to those masses corresponding to 5-mers and larger (>1,550 amu.). Even with this caveat, there are sufficient mass differences to identify the mutation.

All three mutations at position 2481 within the 378-nucleotide p53 fragment are also revealed using this particular version of the analysis (FIG. 21). These results are generic; PEACA can detect a single mutation in a 380 nucleotide long target with a success rate of 95% using natural X-mer precursors (see Table I). The resolving power of PEACA can be increased by incorporating specific mass-modifications at positions $X_5$ and $X_6$. More power can be obtained by placing the defined rX further towards the 5' terminus, say at $X_3$, and incorporating defined mass-modifications at positions $X_4$, $X_5$, and $X_6$.

Example 3 (XLA)

The 62-nucleotide p53 fragment is interrogated by performing XLA using a 6-mer mixture composed of natural nucleotides. FIG. 22 gives the individual mass spectra for the wild type sequence and C2481A mutant. The binary difference spectra reveals five mass peak differences, which are indicative of the given mutation. The same mutation can be detected by XLA in the 378 nucleotide fragment, yet the resulting binary difference spectra reveals only three mass differences (FIG. 23). As discussed above and shown in Table 1, the power of XLA can be increased by using mass-modified X-mer mixtures.

All publications and patent applications cited in this specification are herein incorporated by reference as if each individual publication or patent application where specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE I

Effect of X-mer composition on information content for various assays

| Assay | X-mer Length | Method of X-mer Synthesis | X-mer Comp. | Number of Rxns per Target | MNC | Single Stranded Mutation Detection (length in nucleotides) | Double Stranded Mutation Detection (length in nucleotides) | Single Stranded Mutation Ident. (length in nucleotides) |
|---|---|---|---|---|---|---|---|---|
| PEA | 6-mers | Combinatorial | Natural | 1 | 53 | 100* | 40* | 70* |
| PEA | 6-mers | Combinatorial | Natural | 4 (1 for each ddNTP)‡ | 173 | 300* | 130* | 190* |
| PEA | 6-mers | Individual | Natural | 10 (subsets of precursor mixtures) | 530 | 850* | 400* | 600* |
| PEA | 5-mers | Combinatorial | Mass-modified† | 1 | 275 | 520 | 212 | 360 |
| PEA | 5-mers | Combinatorial | Mass-modified† | 4 (1 for each ddNTP)‡ | 835 | 1,450 | 540 | 1,040 |
| PEA | 6-mers | Combinatorial | Mass-modified† | 1 | 348 | 700 | 320 | 500 |
| PEA | 6-mers | Combinatorial | Mass-modified† | 4 (1 for each ddNTP)‡ | 1,198 | 2,650 | 950 | 1,750 |
| PEA | 6-mers | Individual with mass optimization | Mass-modified† | 1 | 559 | 890 | 440 | 630 |
| PEA | 6-mers | Individual with mass optimization | Mass-modified† | 4 (1 for each ddNTP)‡ | 2,075 | 3,600 | 1,600 | 2,400 |
| PEA | 6-mers | Individual with mass optimization | Mass-modified† | 10 (subsets of precursor mixtures) | 5,590 | 8,900* | 4,400* | 6,300* |
| XLA | 6-mers | Combinatorial | Natural | 1 | nd | ~400 | ~200 | 300 |
| XLA | 6-mers | Combinatorial | Mass-modified† | 1 | nd | ~900 | ~450 | 700 |
| PEACA | 6-mers | Combinatorial | Natural | 4 (mixed for MS analysis) | nd | ~380 | ~170 | -nd- |

Reported values are derived from calculations or simulations described in the text. The values in the last three columns refer to the nucleotide lengths within which the problem can be solved with a 95% success rate. The MNC is defined in the text. Mutation identification refers to the ability to determine both the identity and location of the mutation in an otherwise knownsequence.
*The reported values for these assay conditions are only estimations since complete simulations have yet to be performed.
†The sets of precursors which contain mass-modified nucleotides were composed of the four natural nucleotides and the following derivatives; 2'-O-methyl-2,6-diaminopurine, 5-iodocytidine, 2'-O-methylguanosine, and 5-iodouridine.
Mutation detection refers to the ability to detect differences in mass signatures between a wild type and single mutant thereof.
‡It should be noted that alternative to running four separate reactions (1 for each ddNTP), a single reaction could be performed if mass-tagged ddNTPs were designed such that they segregate all of the 7-mer extension products into four discrete regions of the mass spectra depending upon the terminal ddNTP added as described above and in FIG. 9.

What is claimed:

1. A mixture or set of sub-mixtures comprising natural and mass-modified X-mer precursors, wherein said X-mer precursors have a minimum length of 3 nucleotides, wherein said mixture has a minimum mixture coverage complexity of at least 56/N or wherein said set of sub-mixtures has a composite mixture coverage complexity of at least 56/N, wherein N represents the number of distinct X-mer precursors in the mixture, wherein mass number complexity of said mixture is greater than the mass number complexity of any natural equivalent of said mixture or wherein mass number complexity of said set of sub-mixtures is greater than the mass number complexity of any natural equivalent of said set of sub-mixtures, wherein each sub-mixture in said set has a reduced mixture coverage complexity as compared with the composite mixture coverage complexity and wherein each sub-mixture further comprises a plurality of X-mer precursors, wherein said length is selected independently for each X-mer precursor, and wherein each of said X-mer precursors in said mixture is represented by a single chemical species.

2. A mixture or set of sub-mixtures comprising natural and mass-modified X-mer precursors, wherein said X-mer precursors have a minimum length of 3 nucleotides, wherein said mixture has a minimum mixture coverage complexity of at least 56/N or wherein said set of sub-mixtures has a composite mixture coverage complexity of at least 56/N, wherein N represents the number of distinct X-mer precursors in the mixture, wherein mass number complexity of said mixture is greater than the mass number complexity of any natural equivalent of said mixture or wherein mass number complexity of said set of sub-mixtures is greater than the mass number complexity of any natural equivalent of said set of sub-mixtures, wherein each sub-mixture in said set has a reduced mixture coverage complexity as compared with the composite mixture coverage complexity and wherein each sub-mixture further comprises a plurality of X-mer precursors, wherein said length is selected independently for each X-mer precursor, wherein each of said X-mer precursors in said mixture is represented by a single chemical species, and wherein said X-mer precursors have a determined isotopic composition.

3. The mixture or set of sub-mixtures of claim 1 or 2 wherein said mixture has a mixture coverage complexity of at least about ½ when said mixture contains at least 128 discrete X-mers, or wherein said set of sub-mixtures has a composite mixture coverage complexity of at least about ½ when said set of sub-mixtures contains at least 128 discrete X-mers.

4. The mixture or set of sub-mixtures of claim 1 or 2, wherein said mixture has a mixture coverage complexity of at least about ¼ when said mixture contains at least 256 discrete X-mers, or wherein in said set of sub-mixtures has a composite mixture coverge complexity of at least about ¼ when said set of sub-mixtures contains at least 256 discrete X-mers.

5. The mixture or set of sub-mixtures of claim 1 or 2, wherein said mixture has a mixture coverage complexity of at least about 1/8 when said mixture contains at least 512 discrete X-mers, or wherein said set of sub-mixtures has a composite mixture coverage complexity of at least about 1/8 when said set of sub-mixtures contains at least 512 discrete X-mers.

6. The mixture or set of sub-mixtures of claim 1 or 2 wherein said X-mer precursors have an ionization tag.

7. The mixture or set of sub-mixtures of claim 1 or 2 wherein nucleotide sequences of the precursors of said mixture or set of sub-mixtures are known.

8. The mixture or set of sub-mixtures of claim 1 or 2 wherein at least some of said mass-modified X-mer precursors comprises at least one mass tag or at least one chemical modification of an internucleoside linkage, a sugar backbone, or a nucleoside base.

9. A method of analyzing a target nucleic acid sequence, comprising the steps of:
   (1) hybridizing a mixture or set of sub-mixtures comprising natural and mass-modified X-mer precursors to the target nucleic acid sequence,
      wherein said mixture has a minimum mixture coverage complexity of at least 56/N or wherein said set of sub-mixtures has a composite mixture coverage complexity of at least 56/N, wherein N represents the number of distinct X-mer precursors in the mixture,
      wherein each sub-mixture in said set has a reduced mixture coverage complexity as compared with the composite mixture coverage complexity and further comprises a plurality of X-mer precursors,
      wherein said length is selected independently for each X-mer precursor,
      wherein each of said X-mer precursors in said mixture is represented by a single chemical species, and
      wherein said X-mer precursors comprise a 3'-end and a 5'-end,
   (2) processing said hybrids to alter the mass of said X-mer precursor portions of said hybrids in a target sequence-mediated reaction; and
   (3) analyzing the product of step (2) via mass spectrometry.

10. The method of claim 9 wherein said X-mer precursors have a determined isotopic composition.

11. The method of claim 9 wherein said mass number complexity (MNC) of said mixture is greater than the mass number complexity of any natural equivalent of said mixture or wherein said mass number complexity (MNC) of said set of sub-mixtures is greater than the mass number complexity of any natural equivalent of said set of sub-mixtures.

12. The method of claim 9 wherein said mixture has a mixture coverage complexity of at least about 1/2 when said mixture contains at least 128 discrete X-mers, and wherein said set of sub-mixtures has a composite mixture coverage complexity of at least about 1/2 when said set of sub-mixtures contains at least 128 discrete X-mers.

13. The method of claim 9 wherein said mixture has a mixture coverage complexity of at least about 1/4 when said mixture contains at least 256 discrete X-mers, or wherein said set of sub-mixtures has a composite mixture coverage complexity of at least about 1/4 when said set of sub-mixtures contains at least 256 discrete X-mers.

14. The method of claim 9 wherein said mixture has a mixture coverage complexity of at least about 1/8 when said mixture contains at least 512 discrete X-mers, or wherein said set of sub-mixtures has a composite mixture coverage complexity of at least about 1/8 when said set of sub-mixtures contains at least 512 discrete X-mers.

15. The method of claim 9 wherein said mixture is provided in at least two reaction mixtures.

16. The method of claim 9 wherein at least some of said mass-modified X-mer precursors comprise at least one mass tag or at least one chemical modification of a internucleoside linkage, a sugar backbone, or a nucleoside base.

17. The method of claim 9 wherein said processing step comprises altering the mass of said X-mer precursor portions of said hybrids by an amount greater than that defined by the mass difference between the lightest and heaviest X-mer in the mixture.

18. The method of claim 9 further comprising the step of:
   purifying the products of step (2) prior to analysis via mass spectrometry.

19. The method of claim 9 further comprising the step of:
   separating the products of step (2) prior to analysis via mass spectrometry.

20. The method of claim 9 wherein steps (1)–(2) are conducted in solution.

21. The method of claim 9 wherein steps (1)–(2) are conducted with a surface-bound mixture.

22. The method of claim 9 wherein said products are analyzed via MALDI-TOF mass spectrometry.

23. The method of claim 9 wherein said processing step comprises a target sequence mediated enzymatic assay.

24. The method of claim 23 wherein said enzymatic assay is an assay selected from a polymerase extension assay and a ligase assay.

25. The method of claim 9 wherein said processing step comprises extending said hybridized X-mer precursors by polymerizing at least one nucleotide at said 3'-end of said hybridized X-mer precursors.

26. The method of claim 9 wherein said processing step comprises extending said hybridized X-mer precursors by polymerizing a single nucleotide at said 3'-end of said hybridized X-mer precursors.

27. The method of claim 25 wherein hybridized X-mer precursors are extended using an enzyme having a nucleotide polymerase activity.

28. The method of claim 25 wherein said nucleotide is a chain-terminating nucleotide triphosphate.

29. The method of claim 28 wherein said chain-terminating nucleotide triphosphate is a nucleotide selected from the group consisting of natural dideoxynucleotide triphosphates and mass-modified dideoxynucleotide triphosphates.

30. The method of claim 29 wherein the mass of said mass-modified dideoxynucleotide triphosphate is greater than that defined by the mass difference between the lightest and heaviest X-mer in the mixture.

31. The method of claim 25 further comprising the step of:
   digesting the products of step (2) prior to analysis via mass spectrometry.

32. The method of claim 31, wherein said nucleotide is a nucleotide selected from the group consisting of: extension nucleotide triphosphates, natural dideoxynucleotide triphosphates, and mass-modified dideoxynucleotide triphosphates.

33. The method of claim 32, wherein said extension nucleotide triphosphates are nucleotides selected from the group consisting of: deoxynucleotides, 5'-($\alpha$)-phosphothioate analogues, 5'-N-($\alpha$)-phosphoramidate analogues and ribonucleotides.

34. The method of claim 31 wherein said digestion step is carried out with a nuclease.

35. The method of claim 34 wherein said nuclease is 5'-exonuclease.

36. The method of claim 35 wherein said 5'-exonuclease is an enzyme selected from the group consisting of DNA polymerase and T7 Gene 6.

37. The method of claim 31 wherein said digestion step is carried out via a chemical reaction.

38. The method of claim 9 wherein said processing step comprises ligating adjacent X-mer precursors using a DNA ligase.

39. The method of claim 9 wherein said processing step comprises ligating adjacent X-mer precursors using a condensing agent.

40. The method of claim 39 wherein said condensing agent is selected from the group consisting of carbodiimides and cyanogen bromide derivatives.

41. The method of claim 9 wherein said processing step comprises a chemical assay.

42. A method of analyzing a target nucleic acid sequence having a 3'-end and a 5'-end, comprising the steps of:
  (1) hybridizing said target nucleic acid sequence to a multiplicity of nucleic acid probes in an array comprising:
    (a) a surface; and
    (b) said multiplicity of nucleic acid sequence probes comprising:
      (i) a cleavable linker attached to said surface; and
      (ii) a nucleic acid sequence having a 3'-end and a terminal 5'-phosphate wherein said 3'-end of said nucleic acid sequence is attached to said cleavable linker;
  (2) hybridizing a mixture or sat of sub-mixtures comprising natural and mass-modified X-mer precursors to the target nucleic acid sequence,
    wherein said mixture has a minimum mixture coverage complexity of at least 56/N or wherein said set of sub-mixtures has a composite mixture coverage complexity of at least 56/N, wherein N represents the number of distinct X-mer precursors in the mixture,
    wherein each sub-mixture in said set has a reduced mixture coverage complexity as compared with the composite mixture coverage complexity and wherein each sub-mixture further comprises a plurality of X-mer precursors,
    wherein said length is selected independently for each X-mer precursor,
    wherein each of said X-mer precursors in said mixture or said sub-mixture is represented by a single chemical species, and
    wherein said X-mer precursors comprise a 3'-end and a 5'-end,
  (3) ligating said hybridized X-mer precursors located adjacent to said terminal 5'-phosphate with said surface-bound probe to form a hybridized precursor/probe complex with said target nucleic acid sequence attached thereto; and
  (4) cleaving said complex at said cleavable linker; and
  (5) analyzing said complex via mass spectrometry.

43. The method of claim 42, wherein said mass number complexity (MNC) of said mixture is greater than the mass number complexity of any natural equivalent of said mixture or wherein said mass number complexity (MNC) of said set of sub-mixtures is greater than the mass number complexity of any natural equivalent of said set of sub-mixtures.

44. The method of claim 42, wherein said mixture has a mixture coverage complexity of at least about ½ when said mixture contains at least 128 discrete X-mers, and wherein said set of sub-mixtures has a composite mixture coverage complexity of at least about ½ when said set of sub-mixtures contains at least 128 discrete X-mers.

45. The method of claim 42, wherein said mixture has a mixture coverage complexity of at least about ¼ when said mixture contains at least 256 discrete X-mers, or wherein said set of sub-mixtures has a composite mixture coverage complexity of at least about ¼ when said set of sub-mixtures contains at least 256 discrete X-mers.

46. The method of claim 42, wherein said mixture has a mixture coverage complexity of at least about ⅛ when said mixture contains at least 512 discrete X-mers, or wherein said set of sub-mixtures has a composite mixture coverage complexity of at least about ⅛ when said set of sub-mixtures contains at least 512 discrete X-mers.

47. The method of claim 42, wherein nucleotide sequences of the X-mer precursors of said mixture or said set of sub-mixtures are known.

48. The method of claim 42, wherein said mixture is provided in at least two reaction mixtures.

49. The method of claim 42, wherein at least some of said mass-modified X-mer precursors comprise at least one mass tag or at least one chemical modification of a internucleoside linkage, a sugar backbone, or a nucleoside base.

50. The method of claim 42 wherein said hybridized X-mer precursor ligated with said probe using a DNA ligase.

51. The method of claim 42, wherein said hybridized X-mer precursor ligated with said probe using a condensing agent.

52. The method of claim 51, wherein condensing agent is selected from the group consisting of carbodiimides and cyanogen bromide derivatives.

53. The method of claim 42 wherein said cleavable linker is a photocleavable linker.

54. The method of claim 42 wherein said cleavable linker is a chemical cleavable linker.

55. The method of claim 42 wherein said complexes are analyzed via MALDI-TOF mass spectrometry.

56. A kit for carrying out a method of analyzing a target nucleic acid sequence, comprising:
  a. the mixture or the set of sub-mixtures of claim 1;
  b. an enzyme having a nuclcotide polymerase activity; and
  c. a multiplicity of nucleotides selected from the group consisting of natural chain-terninating triphosphates and mass-modified chain-terminating triphosphates.

57. A kit for carrying out a method of analyzing a target nucleic acid sequence, comprising:
  a. the mixture or the set of sub-mixtures of claim 1;
  b. an enzyme having DNA polymerase activity;
  c. a multiplicity of nucleotides selected from the group consisting of natural chain-terminating triphosphates and mass-modified chain-terminating triphosphates; and
  d. a multiplicity of extension nucleotide triphosphates.

58. A kit for carrying out a method of analyzing a target nucleic acid sequence, comprising:
  a. the mixture or the set of sub-mixtures of claim 1;
  b. an enzyme having DNA polymerase activity;
  c. a multiplicity of nucleotides selected from the group consisting of natural chain-terminating triphosphates and mass-modified chain-terminating triphosphates; and
  d. a nuclease.

59. A kit for carrying out a method of analyzing a target nucleic acid sequence, comprising:

a. the mixture or the set of sub-mixtures of claim 1;
b. an enzyme having DNA polymerase activity;
c. a multiplicity of nucleotides selected from the group consisting of natural chain-terminating triphosphates and mass-modified chain-terminating triphosphates;
d. a nuclease; and
e. a multiplicity of extension nucleotide triphosphates.

60. A kit for carrying out a method of analyzing a target nucleic acid sequence, comprising:
a. the mixture or the set of sub-mixtures of claim 1;
b. a DNA polymerase;
c. a multiplicity of nucleotides selected from the group consisting of natural chain-terminating triphosphates and mass-modified chain-terminating triphosphates;
d. a 5'-exonuclease; and
e. a multiplicity of extension nucleotide triphosphates and 5'-(α)-phosphothioate analogues.

61. A kit for carrying out a method of analyzing a target nucleic acid sequence, comprising:
a. the mixture or the set of sub-mixtures of claim 1; and
b. a DNA ligase.

62. A kit for carrying out a method of analyzing a target nucleic acid sequence, comprising:
a. the mixture or the set of sub-mixtures of claim 1;
b. a DNA ligase; and
c. a nuclease.

63. A kit for carrying a method of analyzing a target nucleic acid sequence, comprising:
a the mixture or the set of sub-mixtures of claim 1; and
b. a condensing agent.

64. A kit for carrying out a method of analyzing a target nucleic acid sequence having a 3'-end and a 5'-end, comprising:
a. the mixture or the set of sub-mixtures of claim 1;
b. a DNA ligase; and
c. a n array comprising:
   (a) a surface; and
   (b) a multiplicity of nucleic acid sequence probes comprising:
      (i) a cleavable linker attached to said surface; and
      (ii) a nucleic acid sequence having a 3'-end and a terminal 5'-phosphate wherein said 3'-end of said nucleic acid sequence is attached to said cleavable linker.

65. A kit for carrying out a method of analyzing a target nucleic acid sequence having a 3'-end and a 5'-end, comprising:
a. the mixture or the set of sub-mixtures of claim 1;
b. a condensing agent; and
c. an array comprising:
   (a) a surface; and
   (b) a multiplicity of nucleic acid sequence probes comprising:
      (i) a cleavable linker attached to said surface; and
      (ii) a nucleic acid sequence having a 3'-end and a terminal 5'-phosphate wherein said 3'-end of said nucleic acid sequence is attached to said cleavable linker.

66. The method of claim 9, 10 or 11, wherein said X-mer precursors have an ionization tag.

67. The method of claim 28 wherein said chain-terminating nucleotides have an ionization tag.

68. A mixture or set of sub-mixtures comprising mass-modified X-mer precursors,
wherein said X-mer precursors have a minimum length of 3 nucleotides,
wherein said mixture has a minimum mixture coverage complexity of at least 56/N or wherein said set of sub-mixtures has a composite mixture coverage complexity of at least 56/N, wherein N represents the number of distinct X-mer precursors in the mixture,
wherein mass number complexity of said mixture or said set of sub-mixtures is greater than the mass number complexity of any natural equivalent of said mixture or said set of sub-mixtures,
wherein each sub-mixture in said set has a reduced mixture coverage complexity as compared with the composite mixture coverage complexity and wherein each sub-mixture further comprises a plurality of X-mer precursors,
wherein said length is selected independently for each X-mer precursor, and
wherein each of said X-mer precursors in said mixture is represented by a single chemical species.

69. The method of claim 9, wherein the step (1) of hybridizing, the mixture or set of sub-mixtures comprises mass-modified X-mer precursors.

70. The method of claim 42, wherein the step (2) of hybridizing a mixture or set of sub-mixtures to the target nucleic acid sequence, the mixture or set of sub-mixtures comprises mass-modified X-mer precursors.

* * * * *

SEQUENCE LISTING

<160> NUMBER OF SEQ ID NOS: 13

<210> SEQ ID NO 1
<211> LENGTH: 63
<212> TYPE: DNA
<213> ORGANISM: Homo sapiens
<220> FEATURE:
<223> OTHER INFORMATION: P53-wt

<400> SEQUENCE: 1
atgtgtaaca gttcctgcat gggcggcatg aaccggaggc ccatcctcac catcatcaca    60
ctg                                                            63

<210> SEQ ID NO 2
<211> LENGTH: 63
<212> TYPE: DNA
<213> ORGANISM: Homo sapiens
<220> FEATURE:
<223> OTHER INFORMATION: P53-2451-6

<400> SEQUENCE: 2
atgtgtaaca gttcctgcat gggccgcatg aaccggaggc ccatcctcac catcatcaca      60
ctg                                                            63

<210> SEQ ID NO 3
<211> LENGTH: 63
<212> TYPE: DNA
<213> ORGANISM: Homo sapiens
<220> FEATURE:
<223> OTHER INFORMATION: P53_2481-1

<400> SEQUENCE: 3
atgtgtaaca gttcctgcat gggcggcatg aactggaggc ccatcctcac catcatcaca      60
ctg                                                            63

<210> SEQ ID NO 4
<211> LENGTH: 63
<212> TYPE: DNA
<213> ORGANISM: Homo sapiens
<220> FEATURE:
<223> OTHER INFORMATION: P53-2481-2

<400> SEQUENCE: 4
atgtgtaaca gttcctgcat gggcggcatg aacgggaggc ccatcctcac catcatcaca      60
ctg                                                            63

<210> SEQ ID NO 5
<211> LENGTH: 63
<212> TYPE: DNA
<213> ORGANISM: Homo sapiens
<220> FEATURE:
<223> OTHER INFORMATION: P53-2481-5

<400> SEQUENCE: 5
atgtgtaaca gttcctgcat gggcggcatg aacaggaggc ccatcctcac catcatcaca      60
ctg                                                            63

<210> SEQ ID NO 6
<211> LENGTH: 63
<212> TYPE: DNA
<213> ORGANISM: Homo sapiens
<220> FEATURE:
<223> OTHER INFORMATION: P53-2482-3

<400> SEQUENCE: 6
atgtgtaaca gttcctgcat gggcggcatg aaccagaggc ccatcctcac catcatcaca      60
ctg                                                            63

<210> SEQ ID NO 7
<211> LENGTH: 63
<212> TYPE: DNA
<213> ORGANISM: Homo sapiens
<220> FEATURE:
<223> OTHER INFORMATION: P53-2482-5

<400> SEQUENCE: 7

```
atgtgtaaca gttcctgcat gggcggcatg aacctgaggc ccatcctcac catcatcaca    60
ctg                                                                  63
```

<210> SEQ ID NO 8
<211> LENGTH: 63
<212> TYPE: DNA
<213> ORGANISM: Homo sapiens
<220> FEATURE:
<223> OTHER INFORMATION: P53-2482-6

<400> SEQUENCE: 8

```
atgtgtaaca gttcctgcat gggcggcatg aacccgaggc ccatcctcac catcatcaca    60
ctg                                                                  63
```

<210> SEQ ID NO 9
<211> LENGTH: 378
<212> TYPE: DNA
<213> ORGANISM: Homo sapiens
<220> FEATURE:
<223> OTHER INFORMATION: Nucleotide Fragment of the Wild-Type P53 Gene

<400> SEQUENCE: 9

```
cagtcacagc acatgacgga ggttgtgagg cgctgccccc accatgagcg ctgctcagat    60
agcgatggtc tggcccctcc tcagcatctt atccgagtgg aaggaaattt gcgtgtggag   120
tatttggatg acagaaacac ttttcgacat agtgtggtgg tgccctatga gccgcctgag   180
gttggctctg actgtaccac catccactac aactacatgt gtaacagttc ctgcatgggc   240
ggcatgaacc ggaggcccat cctcaccatc atcacactgg aagactccag tggtaatcta   300
ctgggacgga acagctttga ggtgcgtgtt tgtgcctgtc ctgggagaga ccggcgcaca   360
gaggaagaga atctccgc                                                378
```

<210> SEQ ID NO 10
<211> LENGTH: 740
<212> TYPE: DNA
<213> ORGANISM: Homo sapiens
<220> FEATURE:
<223> OTHER INFORMATION: Nucleotide Fragment of the Wild Type P53 Gene

<400> SEQUENCE: 10

```
cagggcagct acggtttccg tctgggcttc ttgcattctg ggacagccaa gtctgtgact    60
tgcacgtact cccctgccct caacaagatg ttttgccaac tggccaagac ctgccctgtg   120
cagctgtggg ttgattccac accccgccc ggcaccgcg tccgcgccat ggccatctac   180
aagcagtcac agcacatgac ggaggttgtg aggcgctgcc ccaccatga gcgctgctca   240
gatagcgatg gtctggcccc tcctcagcat cttatccgag tggaaggaaa tttgcgtgtg   300
gagtatttgg atgacagaaa cacttttcga catagtgtgg tggtgcccta tgagccgcct   360
gaggttggct ctgactgtac caccatccac tacaactaca tgtgtaacag ttcctgcatg   420
ggcggcatga accggaggcc catcctcacc atcatcacac tggaagactc cagtggtaat   480
ctactgggac ggaacagctt tgaggtgcgt gtttgtgcct gtcctgggag agaccggcgc   540
acagaggaag agaatctccg caagaaaggg gagcctcacc acgagctgcc cccagggagc   600
actaagcgag cactgcccaa caacaccagc tcctctcccc agccaaagaa gaaaccactg   660
gatggagaat atttcaccct tcagatccgt gggcgtgagc gcttcgagat gttccgagag   720
```

```
ctgaatgagg ccttggaact                                                    740

<210> SEQ ID NO 11
<211> LENGTH: 63
<212> TYPE: DNA
<213> ORGANISM: Homo sapiens

<400> SEQUENCE: 11
tacacattgt caaggacgta cccgccgtac ttggcctccg ggtaggagtg gtagtagtgt         60
gac                                                                      63

<210> SEQ ID NO 12
<211> LENGTH: 63
<212> TYPE: DNA
<213> ORGANISM: Homo sapiens

<400> SEQUENCE: 12
atgtgtaaca gttcctgcat gggcggcatg aaccggaggc ccatcctcac catcatcaca        60
ctg                                                                      63

<210> SEQ ID NO 13
<211> LENGTH: 63
<212> TYPE: DNA
<213> ORGANISM: Homo sapiens

<400> SEQUENCE: 13
atgtgtaaca gttcctgcat gggcggcatg aaccggaggc ccatcctcac catcatcaca        60
ctg                                                                      63
```